(12) United States Patent
Muhammad et al.

(10) Patent No.: US 9,750,707 B2
(45) Date of Patent: Sep. 5, 2017

(54) METHODS AND COMPOSITIONS FOR ADMINISTRATION OF TRPV1 AGONISTS

(71) Applicant: Acorda Therapeutics, Inc., Ardsley, NY (US)

(72) Inventors: Naweed Muhammad, Fremont, CA (US); Gene Curtis Jamieson, Boulder Creek, CA (US); Keith R. Bley, Menlo Park, CA (US); Sanjay Chanda, South San Francisco, CA (US)

(73) Assignee: ACORDA THERAPEUTICS, INC., Ardsley, NY (US)

( * ) Notice: Subject to any disclaimer, the term of this patent is extended or adjusted under 35 U.S.C. 154(b) by 0 days.

(21) Appl. No.: 14/255,630

(22) Filed: Apr. 17, 2014

(65) Prior Publication Data

US 2015/0073056 A1    Mar. 12, 2015

Related U.S. Application Data

(63) Continuation of application No. 13/585,692, filed on Aug. 14, 2012, now Pat. No. 8,734,770, which is a continuation of application No. 13/083,306, filed on Apr. 8, 2011, now Pat. No. 8,263,093, which is a continuation of application No. 10/823,426, filed on Apr. 12, 2004, now Pat. No. 7,943,166.

(60) Provisional application No. 60/462,040, filed on Apr. 10, 2003, provisional application No. 60/499,062, filed on Aug. 29, 2003, provisional application No. 60/462,457, filed on Apr. 10, 2003.

(51) Int. Cl.
| | |
|---|---|
| *A61F 13/00* | (2006.01) |
| *A61K 31/165* | (2006.01) |
| *A61K 9/00* | (2006.01) |
| *A61K 9/08* | (2006.01) |
| *A61K 9/107* | (2006.01) |
| *A61K 9/127* | (2006.01) |
| *A61K 47/08* | (2006.01) |
| *A61K 47/10* | (2017.01) |
| *A61K 45/06* | (2006.01) |
| *A61K 47/12* | (2006.01) |

(52) U.S. Cl.
CPC .......... *A61K 31/165* (2013.01); *A61K 9/0014* (2013.01); *A61K 9/08* (2013.01); *A61K 9/1075* (2013.01); *A61K 9/127* (2013.01); *A61K 45/06* (2013.01); *A61K 47/08* (2013.01); *A61K 47/10* (2013.01); *A61K 47/12* (2013.01)

(58) Field of Classification Search
CPC ...... A61K 9/0002; A61K 9/0012; A61K 9/06; A61K 9/08; A61K 9/10; A61K 9/107; A61K 9/1075

USPC .......................................... 424/400, 465-489
See application file for complete search history.

(56) References Cited

U.S. PATENT DOCUMENTS

| | | |
|---|---|---|
| 4,313,958 A | 2/1982 | LaHann |
| 4,493,848 A | 1/1985 | LaHann et al. |
| 4,532,139 A | 7/1985 | Janusz et al. |
| 4,544,668 A | 10/1985 | Janusz et al. |
| 4,544,669 A | 10/1985 | LaHann et al. |
| 4,546,112 A | 10/1985 | LaHann et al. |
| 4,564,633 A | 1/1986 | LaHann et al. |
| 4,599,342 A | 7/1986 | LaHann |
| 4,863,970 A * | 9/1989 | Patel .................... A61K 9/0014 514/772 |
| 4,892,890 A | 1/1990 | Damani |
| 4,927,687 A | 5/1990 | Nuwayser |
| 4,952,402 A | 8/1990 | Sparks et al. |
| 5,028,535 A | 7/1991 | Buechler et al. |
| 5,221,692 A | 6/1993 | Chen |
| 5,505,958 A | 4/1996 | Bello et al. |
| 5,654,337 A | 8/1997 | Roentsch et al. |
| 5,665,378 A | 9/1997 | Davis et al. |
| 5,716,643 A | 2/1998 | Yen |
| 5,756,107 A | 5/1998 | Hahn et al. |
| 5,762,963 A | 6/1998 | Byas-Smith |
| 5,869,533 A | 2/1999 | Holt |
| 5,879,696 A | 3/1999 | Blumberg |
| 5,962,532 A | 10/1999 | Campbell et al. |
| 5,968,539 A | 10/1999 | Beerse et al. |
| 6,013,270 A | 1/2000 | Hargraves et al. |
| 6,103,266 A | 8/2000 | Tapolsky et al. |
| 6,239,180 B1 | 5/2001 | Robbins |
| 6,248,788 B1 | 6/2001 | Robbins et al. |
| 6,264,988 B1 | 7/2001 | Yen |

(Continued)

FOREIGN PATENT DOCUMENTS

| | | |
|---|---|---|
| CA | 2 497 771 A1 | 3/2004 |
| EP | 0 149 545 A2 | 7/1985 |

(Continued)

OTHER PUBLICATIONS

Magerl et al (Roles of capsaicin-insensitive nociceptors in cutaneous pain and secondary hyperalgesia; Brain, 124, 2001, 1754-1764).*

(Continued)

*Primary Examiner* — Micah-Paul Young
(74) *Attorney, Agent, or Firm* — Morrison and Foerster LLP

(57) ABSTRACT

Compositions are provided that contain a TRPV1 agonist, such as capsaicin, and a solvent system. Topical application of the composition results in rapid delivery of agonist to the dermis and epidermis. Method of using the compositions for reducing nociceptive nerve fiber function in subjects, and for treatment of capsaicin-responsive conditions are also provided.

84 Claims, 4 Drawing Sheets

(56) References Cited

U.S. PATENT DOCUMENTS

| | | |
|---|---|---|
| 6,277,398 B1 | 8/2001 | Caruso |
| 6,299,900 B1 | 10/2001 | Reed et al. |
| 6,299,902 B1 | 10/2001 | Jun et al. |
| 6,390,291 B1 | 5/2002 | Garrill et al. |
| 6,444,234 B1 | 9/2002 | Kirby et al. |
| RE37,934 E | 12/2002 | Hoffmann |
| 6,576,712 B2 | 6/2003 | Feldstein et al. |
| 6,638,981 B2 | 10/2003 | Williams et al. |
| 6,818,671 B1 | 11/2004 | Embil et al. |
| 7,335,379 B2 | 2/2008 | Carrara et al. |
| 7,943,166 B2 | 5/2011 | Muhammad et al. |
| 8,263,093 B2 | 9/2012 | Muhammad et al. |
| 8,273,390 B2 | 9/2012 | Muhammad et al. |
| 8,734,770 B2 | 5/2014 | Muhammad et al. |
| 2001/0002406 A1* | 5/2001 | Robbins ............... A61K 9/7023 514/627 |
| 2002/0058048 A1 | 5/2002 | Tamura et al. |
| 2003/0104040 A1 | 6/2003 | Kirby et al. |
| 2003/0104085 A1 | 6/2003 | Yeomans |
| 2004/0126415 A1 | 7/2004 | Lu et al. |
| 2004/0202707 A1 | 10/2004 | Muller |
| 2005/0084520 A1 | 4/2005 | Bernstein |
| 2006/0204561 A1 | 9/2006 | Muhammad et al. |
| 2006/0222690 A1 | 10/2006 | Bley |
| 2011/0182972 A1 | 7/2011 | Bley |
| 2011/0184069 A1 | 7/2011 | Muhammad et al. |
| 2011/0196043 A1 | 8/2011 | Muhammad et al. |

FOREIGN PATENT DOCUMENTS

| | | |
|---|---|---|
| EP | 0 149 545 A3 | 7/1985 |
| EP | 0 149 545 B1 | 7/1985 |
| EP | 0 225 848 A2 | 6/1987 |
| EP | 0 347 000 A2 | 12/1989 |
| EP | 0 612 525 A1 | 8/1994 |
| EP | 0 612 525 B1 | 8/1994 |
| EP | 1 568 365 A1 | 8/2005 |
| JP | 7-2670 A | 1/1995 |
| JP | 2000-143513 A | 5/2000 |
| JP | 2001-114677 A | 4/2001 |
| JP | 2001-213772 A | 8/2001 |
| JP | 2002-522488 A | 7/2002 |
| JP | 2003-95983 A | 4/2003 |
| JP | 2003-95985 A | 4/2003 |
| WO | WO-92-09285 A1 | 6/1992 |
| WO | WO-98-03641 A1 | 1/1998 |
| WO | WO-98-53825 A1 | 12/1998 |
| WO | WO-00-09117 A1 | 2/2000 |
| WO | WO-00-50007 A1 | 8/2000 |
| WO | WO-00-50387 A1 | 8/2000 |
| WO | WO-00-59475 A1 | 10/2000 |
| WO | WO-00-67730 A1 | 11/2000 |
| WO | WO-02-09763 A2 | 2/2002 |
| WO | WO-2004-021990 A2 | 3/2004 |
| WO | WO-2004-021990 A3 | 3/2004 |
| WO | WO-2004-089361 A1 | 10/2004 |
| WO | WO-2004-091521 A2 | 10/2004 |
| WO | WO-2004-091521 A3 | 10/2004 |
| WO | WO-2004-092122 A2 | 10/2004 |
| WO | WO-2004-092122 A3 | 10/2004 |
| WO | WO-2005-009510 A2 | 2/2005 |
| WO | WO-2005-009510 A3 | 2/2005 |
| WO | WO-2006/089012 A2 | 8/2006 |
| WO | WO-2006/089012 A3 | 8/2006 |
| WO | WO-2006-105481 A1 | 10/2006 |

OTHER PUBLICATIONS

Lynn, Capsaicin: actions on nociceptive C-fibers and therepeutic potential, Review Article, Pain, 41, 1990, 61-69.*
Anderson, W.S. et al. (2002). "Naloxone Increases Pain Induced by Topical Capsaicin in Healthy Human Volunteers," Pain 99:207-216.
Anonymous. (Jul. 2004). "Adding Value with ATD Technology," Antares Pharma AG.pp. 1-38.
Anonymous. (2004). "I Have Vulvodynia—What Do I Need to Know: A Self-Help Guide for Women Diagnosed with Vulvodynia," National Vulvodynia Association Pamphlet 12 pages.
Asbill, C.S. et al. (2000). "Enhancement of Transdermal Drug Delivery: Chemical and Physical Approaches," Crit. Rev. Ther. Drug Carrier Syst. 17(6):621-658.
Backonja, M-M. et al. (Jan. 2003). "A Single One Hour Application of High-Concentration Capsaicin Patches Leads to Four Weeks of Pain Relief in Posttherpetic Neuralgia Patients," American Academy of Neurology Abstract, two pages.
Balaban, C.D. et al. (2003). "Type I Vanilloid Receptor Expression by Mammalian Inner Ear Ganglion Cells," Hear Res.175:165-170.
Barry, B.W. (1993). "Vehicle Effect: What is an Enhancer?" Chapter 14 in Topical Drug Bioavailability, Bioequivalence, and Penetration Shah, V.P. et al. eds. Plenum Press: New York, NY pp. 261-276.
Baudoin, T. et al. (2000). "Capsaicin Significantly Reduces Sinonasal Polyps," Acta. Otolaryngol. 120:307-311.
Behrendt, H.-J. et al. (2004). "Characterization of the Mouse Cold-Menthol Receptor TRPM8 and Vanilloid Receptor Type-1 VR1 Using a Fluorometric Imaging Plate Reader (FLIPR) Assay," Br. J. Pharmacol. 141(4):737-745.
Bellocq, A.M. et al. (1984). "Microemulsions" In Advances in Colloid and Interface Science Elsevier Science Publishers B.V., Amsterdam 20:167-272.
Bennett, G.J. (Oct. 15, 1998). "Neuropathic Pain: New Insights, New Interventions," Hosp. Pract. 33(10):95-114.
Berger, A. et al. (Apr. 1995). "Oral Capsaicin Provides Temporary Relief for Oral Mucositis Pain Secondary to Chemotherapy-Radiation Therapy," J. Pain Symptom Manage. 10(3):243-248.
Bernstein, J.E. et al. (Sep. 1986). "Effects of Topically Applied Capsaicin on Moderate and Severe Psoriasis Vulgaris," J. Am. Acad. Dermatol. 15(3):504-507.
Bjerring, P. et al. (1989). "Use of a New Argon Laser Technique to Evaluate Changes in Sensory and Pain Thresholds in Human Skin Following Topical Capsaicin Treatment," Skin Pharmacol. 2:162-167.
Bley, K.R. (2003). "Advances in Localized Management of Neuropathic Pain," NeurogesX, Inc. pp. 1-6.
Bley, K.R. (2004). "Recent Developments in Transient Receptor Potential Vanilloid Receptor 1 Agonist-Based Therapies," Expert Opin. Investig. Drugs 13:1445-1456.
Bourrel, M. et al. (1988). Microemulsions and Related Systems, Marcel Dekker: New York, NY pp. ix-xi (Table of Contents Only.).
Brand, L.M. et al. (1990). "Anti-Inflammatory Pharmacology and Mechanism of the Orally Active Capsaicin Analogs, NE-19550 and NE-28345," Agents and Actions 31(3-4):329-340.
Caterina, M.J. et al. (2001). "The Vanilloid Receptor: A Molecular Gateway to the Pain Pathway," Annu. Rev. Neurosci. 24:487-517.
Chancellor, M.B. et al. (Jul. 1999). "Intravesical Capsaicin and Resiniferatoxin Therapy: Spicing up the Ways to Treat the Overactive Bladder," J. Urol. 162:3-11.
Chattaraj, S.C. et al. (1995). "Chemical Penetration Enhancers" Table 1 in "Penetration Enhancer Classification" Chapter 1.2 in Percutaneous Penetration Enhancers Smith, E.W. et al. eds. CRC Press: Boca Raton, Florida pp. 5-20.
Daniels, R. (Aug. 2004). "Strategies for Skin Penetration Enhancement," Skin Care Forum, Issue 37, located at <http:--www.scf-online.com-english-37_e-37_e_pr-skinpenetration37_e_pr. html>, last visited Jul. 28, 2006, 11 pages.
Dray, A. et al. (1990). "NE-19550 and NE-21610, Antinociceptive Capsaicin Analogues: Studies on Nociceptive Fibres of the Neonatal Rat Tail in vitro," Eur. J. Pharmacol. 181:289-293.
Dray, A. et al. (1991). "Systemic Capsaicin and Olvanil Reduce the Acute Algogenic and the Late Inflammatory Phase Following Formalin Injection Into Rodent Paw," Pain 47:79-83.
Drugs.com. (2006). Drug Information for Capsacin (Topical) located at <http:--www.drugs.com-cons-Zostrix.html>, last visited Jul. 27, 2006, five pages.
Durrheim, H. et al. (Jul. 1980). "Permeation of Hairless Mouse Skin I: Experimental Methods and Comparison with Human Epidermal Permeation by Alkanols," J. Pharm. Sci. 69(7):781-786.

(56) References Cited

OTHER PUBLICATIONS

Dworkin, R.H. (Nov.-Dec. 2002). "An Overview of Neuropathic Pain: Syndromes, Symptoms, Signs, and Several Mechanisms," Clin. J. Pain 18(6):343-349.
Ellis, C.N. et al. (1993). "A Double-Blind Evaluation of Topical Capsaicin in Pruritic Psoriasis," J. Am Acad. Dermatol. 29(3):438-442.
Exintaris, B. et al. (Jul. 2002). "Spontaneous Slow Wave and Contractile Activity of the Guinea Pig Prostate," J. Urol. 168:315-322.
Fang, J-Y. et al. (Sep. 2005). "Electrically-Assisted Skin Permeation of Two Synthetic Capsaicin Derivatives, Sodium Nonivamide Acetate and Sodium Nonivamide Propionate, via Rate-Controlling Polyethylene Membranes," Biological and Pharmaceutical Bulletin 28(9):1695-1701.
Final Office Action mailed on Aug. 28, 2009, for U.S. Appl. No. 10/823,426, filed Apr. 12, 2004, 10 pages.
Final Office Action mailed on Feb. 18, 2010, for U.S. Appl. No. 11/396,161, filed Mar. 30, 2006, 11 pages.
Final Office Action mailed on Nov. 3, 2010, for U.S. Appl. No. 11/396,161, filed Mar. 30, 2006, 10 pages.
Final Office Action mailed on Sep. 24, 2012, for U.S. Appl. No. 13/083,281, filed Apr. 8, 2011, 8 pages.
Final Office Action mailed on Sep. 13, 2013, for U.S. Appl. No. 13/585,692, filed Aug. 14, 2012, 7 pages.
Fowler, C.J. et al. (2002). "Voiding and the Sacral Reflex Arc: Lessons from Capsaicin Instillation," Scand. J. Urol. Nephro. Supple. 210:46-50.
Franz, T.J. et al. (Apr. 1990). "The Use of Water Permeability as a Means of Validation for Skin Integrity in in-vitro Percutaneous Absorption Studies," J. Invest. Dermatol. 94(4):525, Abstract only.
Franz, T.J. et al. (1992). "Transdermal Delivery" Chapter 8 in Treatise on Controlled Drug Delivery, Kydonieus, A. ed. Marcell Dekker, Inc.: New York, NY pp. 341-421.
Frerick, H. et al. (Nov. 2003). "Topical Treatment of Chronic Low Back Pain with a Capsicum Plaster," Pain 106(1-2):59-64.
Friedrich, E.G. Jr. (Jun. 1988). "Therapeutic Studies on Vulvar Vestibulitis," Journal of Reprod. Med. 33(6):514-518.
Frot, M. et al. (2004). "Sex Differences in Pain Perception and Anxiety. A Psychophysical Study with Topical Capsaicin," Pain 108:230-236.
Fuchs, P.N. et al. (2000). "Secondary Hyperalgesia Persists in Capsaicin Desensitized Skin," Pain 84:141-149.
Galer, B.S. et al. (Sep.-Oct. 2002). "The Lidocaine Patch 5% Effectively Treats All Neuropathic Pain Qualities: Results of a Randomized, Double-Blind, Vehicle-Controlled, 3-Week Efficacy Study With Use of the Neuropathic Pain Scale," Clin. J. Pain 18(5):297-301.
Ghafourian, T. et al. (Sep. 14, 2004). "The Effect of Penetration Enhancers on Drug Delivery Through Skin: A QSAR Study," Journal of Controlled Release 99(1):113-125.
Guyatt, G.H. et al. (1987). "A Comparison of Likert and Visual Analogue Scales for Measuring Change in Function." *J. Chronic Dis.* 40(12):1129-1133.
Harden, N. et al. (May 2003). "Unmet Needs in the Management of Neuropathic Pain," *J. Pain Symptom Management* 25(5S):S12-S17.
Hautkappe, M. et al. (Jun. 1998). "Review of the Effectiveness of Capsaicin for Painful Cutaneous Disorders and Neural Dysfunction," Clin. J. Pain 14(2):97-106.
Herrmann, D.N. et al. (Mar. 2004). "Epidermal Nerve Fiber Density, Axonal Swellings and QST as Predictors of HIV Distal Sensory Neuropathy," Muscle & Nerve. 29:420-427.
Hoskin, P.J. et al. (1991). "Opioid Agonist-Antagonist Drugs in Acute and Chronic Pain States," Drugs 41(3):326-344.
Hua, X.Y. et al. (1997). "Antinociception Induced by Civamide, an Orally Active Capsaicin Analogue," Pain 71:313-322.
International Search Report for PCT Application No. PCT-US04-11336 filed on Apr. 12, 2004, mailed on Dec. 20, 2004, three pages.
International Search Report for PCT Application No. PCT-US2006-005453 filed on Feb. 14, 2006, mailed on Feb. 20, 2007, five pages.

International Search Report for PCT Application No. PCT-US2006-012271 filed on Mar. 30, 2006, mailed on Jul. 25, 2006, five pages.
Jerman, J.C. et al. (Jun. 2000). "Characterization Using FLIPR of Rat Vanilloid Receptor (rVR1) Pharmacology," Br. J. Pharmacol. 130(4):916-922.
Kaiko, R.F. (1986). "Controversy in the Management of Chronic Cancer Pain: Therapeutic Equivalents of IM and PO Morphine," J. Pain Symptom Manage. 1:42-45.
Kanikkannan, N. et al. (Jun. 2000). "Structure-Activity Relationship of Chemical Penetration Enhancers in Transdermal Drug Delivery," Current Medicinal Chemistry 7(6):593-608.
Karande, P. et al. (May 2002). "High Throughput Screening of Transdermal Formulations," Pharm. Res. 19(5):655-660.
Karande, P. et al. (Feb. 2004). "Discovery of Transdermal Penetration Enhancers by High-Throughput Screening," Nature Biotechnology 22(2):192-197.
Kasting, G.B. et al. (Jan. 1997). "Percutaneous Absorption of Vanilloids: In Vivo and In Vitro Studies," J. Pharm. Sci. 86(1):142-146.
Keitel, W. et al. (2001). "Capsicum Pain Plaster in Chronic Non-Specific Low Back Pain," Arzneimittelforschung 51(11):896-903.
Kemppainen, B.W. et al. eds. (1990). Methods for Skin Absorption CRC Press, Inc. (Table of Contents Only.).
Kennedy, W.R. et al. (1996). "Quantitation of Epidermal Nerves in Diabetic Neuropathy," Neurology 47:1042-1048.
Kobayashi, Y. et al. (2000). "The Bronchoconstrictive Action of Evodiamine, an Indoloquinazoline Alkaloid Isolated From the Fruits of *Evodia rutaecarpa*, on Guinea-Pig Isolated Bronchus: Possible Involvement on Vanilloid Receptors," Planta Med 66:526-530.
Kobayashi, Y. (May 2003). "The Nociceptive and Anti-Nociceptive Effects of Evodiamine from Fruits of *Evodia rutaecarpa* in Mice," Planta Med 69:425-428.
Lawler, D.M. (1995). "Turbidimetry and Nephelometry" in Encyclopedia of Analytical Science, Townshend, A. ed. Academic Press, Inc. San Diego, CA, pp. 5289-5297. (see Townshend).
Levin, J. et al. (Mar. 21, 2005). "The Correlation Between Transepidermal Water Loss and Percutaneous Absorption: An Overview," J. Controlled Release 103(2):291-299.
Magnusson, B.M. et al. (2000). "In Vitro Percutaneous Penetration of Topically Applied Capsaicin in Relation to In Vivo Sensation Responses," International Journal of Pharmaceutics 195:55-62.
McArthur, J.C. et al. (Dec. 1998). "Epidermal Nerve Fiber Density: Normative Reference Range and Diagnostic Efficiency," Arch. Neurol. 55:1513-1520.
Moller, A.R. (2000). "Similarities Between Severe Tinnitus and Chronic Pain," J. Am. Acad. Audiol. 11 (3):115-124.
Montell, C. et al. (Feb. 2002). "A Unified Nomenclature for the Superfamily of TRP Cation Channels," Mol. Cell. 9:229-231.
Morré, D.J. et al. (Jun. 15, 1997). "NADH Oxidase Activity from Sera Altered by Capsaicin is Widely Distributed Among Cancer Patients," Arch. Biochem. Biophys. 342(2):224-230.
Nanji, A.A. et al. (1987). "Use of Skin Surface Sampling and Ion Mobility Spectrometry as a Preliminary Screening Method for Drug Detection in an Emergency Room." Clin. Toxicol. 25(6):501-515.
Nolano, M. et al. (1999). "Topical Capsaicin in Humans: Parallel Loss of Epidermal Nerve Fibers and Pain Sensation," Pain 81:135-145.
Non-Final Office Action mailed on Feb. 20, 2009, for U.S. Appl. No. 10/823,426, filed Apr. 12, 2004, 10 pages.
Non-Final Office Action mailed on Aug. 21, 2009, for U.S. Appl. No. 11/396,161, filed Mar. 30, 2006, 9 pages.
Non-Final Office Action mailed on Dec. 28, 2009, for U.S. Appl. No. 10/823,426, filed Apr. 12, 2004, 10 pages.
Non-Final Office Action mailed on Aug. 20, 2010, for U.S. Appl. No. 10/823,426, filed Apr. 12, 2004, 10 pages.
Non-Final Office Action mailed on Jul. 29, 2011, for U.S. Appl. No. 13/083,306, filed Apr. 8, 2011, 11 pages.
Non-Final Office Action mailed on Sep. 23, 2011, for U.S. Appl. No. 13/083,294, filed Apr. 8, 2011, 11 pages.
Non-Final Office Action mailed on Sep. 14, 2012, for U.S. Appl. No. 13/585,692, filed Aug. 14, 2012, 6 pages.

(56) References Cited

OTHER PUBLICATIONS

Non-Final Office Action mailed on Feb. 13, 2012, for U.S. Appl. No. 13/083,281, filed Apr. 8, 2011, 6 pages.
Notice of Allowance mailed on Mar. 28, 2011, for U.S. Appl. No. 10/823,426, filed Apr. 12, 2004, 8 pages.
Notice of Allowance mailed on Jun. 12, 2012, for U.S. Appl. No. 13/083,306, filed Apr. 8, 2011, 7 pages.
Pershing, L.K. et al. (2004). "Effects of Vehicle on the Uptake and Elimination Kinetics of Capsaicinoids in Human Skin In Vivo," Toxicology and Applied Pharmacology 200:73-81.
Pertovaara, A. (1988). "Collateral Sprouting of Nociceptive C-Fibers After Cut or Capsaicin Treatment of the Sciatic Nerve in Adult Rats," Neurosci. Lett. 90:248-253.
Prince, L.M. (Mar. 4, 1970). "Microemulsions" J. Soc. Cosmet. Chem. 21:193-204.
Prince, L.M. ed. (1977). "Schulman's Microemulsions" in Microemulsions—Theory and Practice Academic Press, Inc.: New York, NY pp. 1-20.
Rice, A.S. et al. (Nov. 2001). "Gabapentin in Postherpetic Neuralgia: A Randomised, Double Blind, Placebo Controlled Study," Pain 94(2):215-224.
Robbins, W.R. et al. (Mar. 1998). "Treatment of Intractable Pain with Topical Large-Dose Capsaicin: Preliminary Report," Anesth. Analg. 86(3):579-583.
Roberts, M.S. et al. (1993). "Water: The Most Natural Penetration Enhancer" Chapter 1 in Pharmaceutical Skin Penetration Enhancement Walter, K.A. et al. eds., Marcel Dekker: New York, NY, pp. 1-30.
Rowbotham, M.C. et al. (Apr. 1996). "Lidocaine Patch: Double-Blind Controlled Study of a New Treatment Method for Post-Herpetic Neuralgia," Pain 65(1):39-44.
Rowbotham, M. et al. (Dec. 2, 1998). "Gabapentin for the Treatment of Postherpetic Neuralgia: A Randomized Controlled Trial," JAMA 280(21):1837-1842.
Saper, J.R. et al. (Jun. 2002). "Intranasal Civamide for the treatment of Episodic Cluster Headaches," Arch. Neurol. 59:990-994.
Shifflet, M.J. et al. (2002). "Development of Analytical Methods to Accurately and Precisely Determine Residual Active Pharmaceutical Ingredients and Cleaning Agents on Pharmaceutical Surfaces," American Pharmaceutical Review pp. 35-40.
Siao, P. et al. (2003). "Quantitative Sensory Testing," Phys. Med. Rehabil. Clin. N. Am. 14:261-286.
Simpson, D. et al. (2006). "Controlled Study of High-Concentration Capsaicin Patch for Painful HIV-Associated Distal Sensory Polyneuropathy," 13th Conference on Retroviruses and Opportunistic Infections, located at <http:--www.retroconference.org-2006-Abstracts-26135.html>, last visited on Jul. 28, 2006, one page, Abstract No. 79.
Skofitsch, G. et al. (1984). "Comparison of Nonivamide and Capsaicin with Regard to their Pharmacokinetics and Effects on Sensory Neurons," Arzneimittel Forschung 34(1):154-156.
Smart, D. et al. (2001). "Characterisation Using FLIPR of Human Vanilloid VR1 Receptor Pharmacology," Eur. J. Pharmacol. 417:51-58.
Smith, E.W. et al. (1995). "Percutaneous Penetration Enhancers: The Fundamentals" Chapter 1.1 in Percutaneous Penetration Enhancers, Smith, E.W. et al. eds., CRC Press: Boca Raton, FL, pp. 1-4.
Sterner, O. et al. (Nov. 1999). "Novel Natural Vanilloid Receptor Agonists: New Therapeutic Targets for Drug Development," Trends Pharmacol. Sci. 20(11):459-465.

Sullivan, E. et al. (1999). "Measurement of [Ca2+] Using the Fluorometric Imaging Plate Reader (FLIPR)," Chapter 7 In Methods in Molecular Biology Lambert, D.G. ed. Humana Press, Inc.: Totowa, NJ 114:125-133.
Supplementary European Search Report mailed on Jun. 24, 2011, for EP Patent Application No. 04750050.9, filed on Apr. 12, 2004, 4 pages.
Surh, Y-J. (2002). "Anti-Tumor Promoting Potential of Selected Spice Ingredients with Antioxidative and Anti-Inflammatory Activities: A Short Review," Food Chem. Toxicol. 40:1091-1097.
Surh, Y-J. (Sep. 4, 2002). "More Than Spice: Capsaicin in Hot Chili Peppers Makes Tumor Cells Commit Suicide," J. Nat. Cancer Inst. 94(17):1263-1265.
Szallasi, A. et al. (1999). "Vanilloid (Capsaicin) Receptors and Mechanisms," Pharmacological Reviews. 51(2):159-211.
Szallasi, A. (2001). "Vanilloid Receptor Ligands: Hopes and Realities for the Future," Drugs Aging 18(8):561-573.
Tayeb, M.T. et al. (2003). "CYP3A4 and VDR Gene Polymorphisms and the Risk of Prostate Cancer in Men with Benign Prostate Hyperplasia," Br. J. Cancer 88:928-932.
Tojo, K. (Jun. 1987). "Mathematical Modeling of Transdermal Drug Delivery," J. Chem. Eng. Jpn. 20(3):300-308.
Tojo, K. (1988). "Concentration Profile in Plasma After Transdermal Drug Delivery," Int. J. Pharm. 43:201-205.
Townshend, A. ed. (1995). "Turbidimetry and Nephelometry" In Encyclopedia of Analytical Science Academic Press Ltd., UK (Table of Contents Only.).
Tsai, Y-H. et al. (1994). "Percutaneous Absorption of Capsaicin and its Derivatives," Drug Devel. Industrial Pharm. 20(4):719-730.
Tympanidis, P. et al. (2004). "Increased Vanilloid Receptor VR1 Innervation in Vulvodynia," European Journal of Pain 8:129-133.
Van Der Aa, F. et al. (2003). "Interstitial Cells in the Human Prostate: A New Therapeutic Target?" The Prostate 56:250-255.
Vass, Z. et al. (2001). "Capsaicin Stimulation of the Cochlea and Electric Stimulation of the Trigeminal Ganglion Mediate Vascular Permeability in Cochlear and Vertebro-Basilar Arteries: A Potential Cause of Inner Ear Dysfunction in Headache," Neuroscience 103(1):189-201.
Venter, J.P. et al. (2001). "A Comparative Study of an in situ Adapted Diffusion Cell and an in vitro Franz Diffusion Cell Method for Transdermal Absorption of Doxylamine," Eur. J. Pharm. Sci. 13:169-177.
Wang, Y-Y. et al. (2001). "In vitro and in vivo Evaluations of Topically Applied Capsaicin and Nonivamide From Hydrogels," Int. J. Pharm. 224:89-104.
Witte, D.G. et al. (2002). "Use of a Fluorescent Imaging Plate Reader-Based Calcium Assay to Assess Pharmacological Differences Between the Human and Rat Vanilloid Receptor," J. Biomol. Screen 7(5):466-475.
Zahner, M.R. et al. (2003). "Cardiac Vanilloid Receptor 1-Expressing Afferent Nerves and Their Role in the Cardiogenic Sympathetic Reflex in Rats," J. Physiol. 551(2):515-523.
Zatz, J.L. (1983). "Scratching the Surface: Rationale and Approaches to Skin Permeation" Chapter 1 in Skin Permeation, Fundamentals and Application, Zatz, J.L. ed. Allured Publishing Corp., Wheaton, IL, pp. 11-31.
Zheng, J. et al. (Jul. 2003). "Vanilloid Receptors in Hearing: Altered Cochlear Sensitivity by Vanilloids and Expression of TRPV1 in the Organ of Corti," J. Neurophysiol. 90:444-455.

\* cited by examiner

METHODS AND COMPOSITIONS FOR ADMINISTRATION OF TRPV1 AGONISTS

CROSS-REFERENCE TO RELATED APPLICATIONS

This application is a continuation of U.S. patent application Ser. No. 13/585,692, filed on Aug. 14, 2012, which is a continuation of U.S. patent application Ser. No. 13/083,306, filed on Apr. 8, 2011, now U.S. Pat. No. 8,263,093, which is a continuation of U.S. patent application Ser. No. 10/823,426, filed on Apr. 12, 2004, now U.S. Pat. No. 7,943,166, all of which claim priority to U.S. Provisional Application Ser. Nos. 60/462,457 and 60/462,040, both filed on Apr. 10, 2003, and U.S. Provisional Application No. 60/499,062, filed on Aug. 29, 2003. The disclosure of each of these applications is hereby incorporated by reference in its entirety.

FIELD OF THE INVENTION

The invention provides compositions and methods for reducing the density of sensory nerve fibers in tissue and amelioration of capsaicin-responsive conditions, and finds application in the field of medicine.

BACKGROUND

The transient receptor potential vanilloid-1 (TRPV1) is a capsaicin-responsive ligand-gated cation channel selectively expressed on small, unmyelinated peripheral nerve fibers (cutaneous nociceptors). See Caterina and Julius, 2001, "The vanilloid receptor: a molecular gateway to the pain pathway," *Annu Rev Neurosci.* 24:487-517; and Montell et al., 2002, "A unified nomenclature for the superfamily of TRP cation channels," *Mol. Cell.* 9:229-31. When TRPV1 is activated by agonists such as capsaicin and other factors such as heat and acidosis, calcium enters the cell and pain signals are initiated. After disease or injury, cutaneous nociceptors may become persistently hyperactive, spontaneously transmitting excessive pain signals to the spinal cord in the absence of painful stimuli, resulting in various types of chronic pain. When TRPV1 is continuously activated through prolonged exposure to an agonist (e.g., capsaicin), excessive calcium enters the nerve fiber, initiating processes that result in long-term yet reversible impairment of nociceptor function. This is believed to be the mechanism by which application of capsaicin provides relief from pain.

Capsaicin may be effective for amelioration of conditions or diseases other than pain, as well. For example, capsaicin acts as an anti-inflammatory agent, counter-irritant, antipruritic, anti-psoriatic and anti-itch agent (for review, see Szallasi and Blumberg, 1999, "Vanilloid (Capsaicin) Receptors and Mechanisms," *Pharm Revs,* 51:159-211). In addition, capsaicin has been reported to cause apoptosis and/or inhibit proliferation of malignant cancer cells (for review, see Surh, 2002, "More Than Spice: Capsaicin in Hot Chili Peppers Makes Tumor Cells Commit Suicide," *J Nat Cancer Inst,* 94:1263-65), and to reduce sinonasal polyps (Baudoin et al., 2000, "Capsaicin significantly reduces sinonasal polyps" *Acta Otolaryngol* 120:307-11).

Low-concentration capsaicin creams have been used for years to treat painful neuropathies and musculoskeletal pain, but their use is limited because they are painful and inconvenient to apply, normally requiring multiple daily applications for only modest relief Recently, a high concentration capsaicin patch has been developed (NGX-4010; NeurogesX, Inc.) that is believed to provide effective and sustained relief from pain.

The present invention provides additional methods and compositions for administration of capsaicin and other TRPV1 agonists.

BRIEF SUMMARY OF THE INVENTION

The invention relates to methods, compositions, and devices for administration of TRPV1 agonists, such as capsaicin, to individuals in need of treatment.

In one aspect, the invention provides a method of reducing the density of functional nociceptive nerve fibers in a selected region of a subject by contacting the region with a composition that contains a TRPV1 agonist and a solvent system by one or more penetration enhancers, where said composition delivers at least about 3 nmoles agonist to skin as measured in a mouse skin absorption assay. In one embodiment, the composition is an immediate-release composition. In one embodiment, the contacting is under nonocclusive conditions. In one embodiment, the contacting is under nonadherent conditions. In one embodiment, at least about 5 μL of the composition is delivered to each $cm^2$ of the region in about 15 minutes. In an embodiment, a 15 minute application of the composition to skin of a mammal results in a decrease in the density of functional nociceptive nerve fibers by at least about 20%. In an embodiment, the density of functional nociceptive nerve fibers is decreased by at least about 50%. In an embodiment the mammal is a mouse. In an embodiment, the mammal is a human.

In one aspect, the invention provides a method of treating a capsaicin-responsive condition in a subject by administration of a composition that contains a TRPV1 agonist and at least one penetration enhancer, where said composition delivers at least about 3 nmoles agonist to skin as measured in a mouse skin absorption assay. In an embodiment, the composition is an immediate release composition. In an embodiment, the administration is non-occlusive and/or non-adherent. In one embodiment, the capsaicin-responsive condition is neuropathic pain, pain produced by mixed nociceptive and neuropathic etiologies, inflammatory hyperalgesia, vulvodynia, interstitial cystitis, overactive bladder, prostatic hyperplasia, rhinitis, rectal hypersensitivity, burning mouth syndrome, oral mucositis, herpes, prostatic hypertrophy, dermatitis, pruritis, itch, tinnitus, psoriasis, warts, skin cancers, headaches, or wrinkles. In some embodiments, the composition is applied to an area on the surface of skin or mucosa.

In a related aspect, the invention provides a method of treating a capsaicin-responsive condition in a subject, by administration of a composition that contains a TRPV1 agonist and at least two penetration enhancers, where said composition delivers at least about 3 nmoles agonist to skin as measured in a mouse skin absorption assay.

In various embodiments, the composition delivers at least about 6 nmoles agonist to skin, at least about 16 nmoles, at least about 32 nmoles, at least about 49 nmoles, or at least about 65 nmoles agonist to skin in a mouse skin absorption assay.

In an embodiment, the composition has a depot effect of less than about 0.25 as measured in a mouse skin absorption assay. In some embodiments the depot effect is less than about 0.1, less than about 0.02, or less than about 0.001.

In an embodiment, the composition contains the TRPV1 agonist and a solvent system, where penetration enhancer(s) make up at least 20% (v/v) of the solvent system. In other embodiments, penetration enhancer(s) make up at least 50% (v/v), at least 90%, at least 95% or substantially all of the solvent system. In an embodiment, the composition comprises the TRPV1 agonist (e.g., a vanilloid such as capsaicin) at a concentration of from 0.05% (w/v) to 60% (w/v).

In an embodiment the solvent system contains a penetration enhancer selected that is an ether, ester, alcohol, fatty acid, fatty acid ester, fatty alcohol, polyol, terpene, or amine. In one embodiment, the solvent system contains a penetration enhancer selected from 1-menthone, dimethyl isosorbide, caprylic alcohol, lauryl alcohol, oleyl alcohol, ethylene glycol, diethylene glycol, propylene glycol, triethylene glycol, butylene glycol, valeric acid, pelargonic acid, caproic acid, caprylic acid, lauric acid, oleic acid, isovaleric acid, isopropyl butyrate, isopropyl hexanoate, butyl acetate, methyl acetate, methyl valerate, ethyl oleate, poloxamer, d-piperitone, methylnonenoic acid, methylnonenoic alcohol, and d-pulegone.

The invention provides a pharmaceutical composition containing a therapeutically effective amount of a TRPV1 agonist and one or more penetration enhancers, and optionally one or more additional therapeutically active agents, where said composition delivers at least about 3 moles agonist to skin as measured in a mouse skin absorption assay. In an embodiment, the pharmaceutical composition is in a form suitable for administration to a subject. In an embodiment, the concentration of capsaicin is greater than 0.05% and less than 20%.

In one embodiment, the composition that comprises a TRPV1 agonist, and optionally one or more additional therapeutically active agents, in a solvent system by one or more penetration enhancers, where said one or more penetration enhancers, taken together, constitute at least about 50% (v/v), and up to 100%, of the solvent system. In an embodiment, the composition contains another therapeutically active agent, such as a local anesthetic.

In another aspect, the invention provides a system for treating a capsaicin-responsive condition, the system containing the TRPV1 agonist composition or microemulsion and a non-occlusive, non-adherent applicator device for applying the formulation to skin or a mucosal surface. In an embodiment, the applicator device is pre-filled with the composition. Alternatively, the composition is contained in a container separate from the device. In a related embodiment, a kit containing the composition or system and a cleaning composition for removal of agonist is provided.

In another aspect, the invention provides a microemulsion containing a TRPV1 agonist such as capsaicin, as well as methods of treatment using the microemulsion.

In another aspect, the invention provides a method for ranking two or more compositions according to their utility for therapeutic delivery of a TRPV1 agonist to a subject by determining for each composition the depot effect for a solution consisting of the composition and the TRPV1 agonist or a different TRPV1 agonist, comparing the values obtained for each composition, and ranking them compositions according to the values, where a composition with a lower value is ranked more suitable for therapeutic delivery of the TRPV1 agonist.

In another aspect, the invention provides a method of increasing the amount of a topically applied molecule that enters the epidermal and dermal layers by topically applying the molecule in a composition containing methylnonenoyl alcohol or methylnonenoic acid. In a related another aspect, the invention provides a pharmaceutical composition containing capsaicin and methylnonenoyl alcohol or methylnonenoic acid.

In another aspect, the invention provides a method of delivering a TRPV1 agonist to the epidermis and dermis underlying a 1 $cm^2$ area of a skin or mucosal surface of a mammal by contacting the area with a composition comprising the TRPV1 agonist and at least one penetration enhancer, where 15 or 30 minutes after contacting at least about 3 nmole of the TRPV1 agonist is retained in the epidermis and dermis. In certain embodiments, the density of functional nociceptive nerve fibers in the epidermis and dermis is decreased by at least about 20% when measured after the contacting step.

DETAILED DESCRIPTION

1. Introduction

Figure 1:
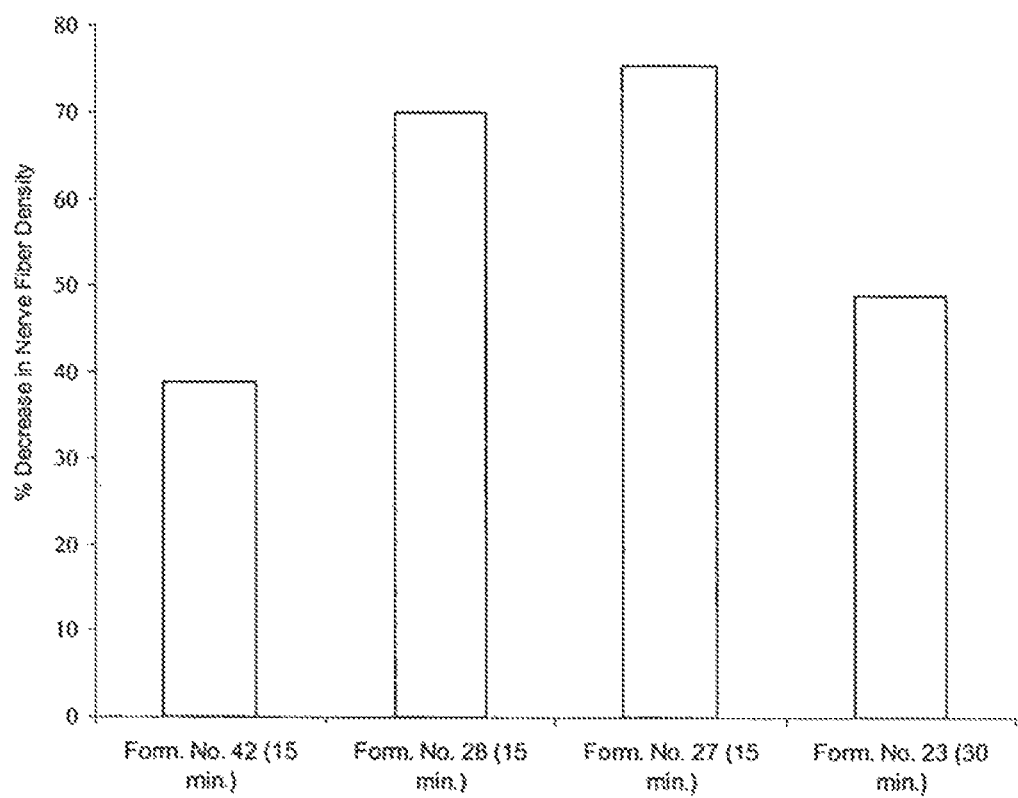
FIG. 1 shows reduction of nerve fiber density in skin (nude mouse) after administration of a TRPV1 agonist.

The present inventions relate, in part, to the discovery that administration of TRPV1 agonist under conditions in which a significant amount of agonist is rapidly and efficiently delivered to, and retained in, the skin provides surprising benefits. In particular, such delivery results in significant reduction in the density of functional cutaneous or mucosal nociceptor nerve fibers in a treated area following only a brief exposure to the agonist (see, e.g., Examples 1, 2 and 3, infra). Further, it is believed that the discomfort ordinarily associated with contact with TRPV1 agonists such as capsaicin is reduced when agonist is rapidly and efficiently delivered to, and retained in, the skin or mucosa (see, e.g., Examples 4 and 5, infra).

In a related aspect, the invention provides a method of treating a capsaicin-responsive condition in a subject by topical administration of a composition containing capsaicin or other TRPV1 agonist under conditions in which a significant amount of agonist is rapidly and efficiently delivered to, and retained in, the skin or mucosa.

In one aspect of the invention, a composition containing a TRPV1 agonist, optionally containing additional therapeutically active agent(s), containing a solvent system containing at least one penetration enhancer, and optionally containing other components as described below, is contacted with the target region of the subject's body (e.g., skin or mucosa). For clarity, this composition is sometimes referred to as the "administered composition." In some embodiments, the solvent system is characterized in that one or more penetration enhancers make up a high proportion of the solvent system.

2. Definitions and Conventions

The following definitions are provided to assist the reader in understanding the invention. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

"Therapeutically effective amount" or "Therapeutically effective dose" refers to the quantity or dose of an agent required to produce a clinically desired result such as a biological or chemical response (e.g., a reduction in density of functional cutaneous or mucosal nociceptor nerve fibers in a subject in need of such reduction), alleviation or amelioration of one or more symptoms of a disease or condition, diminishment of extent of disease, or stabilized state of disease.

"Treating" a condition or patient refers to taking steps to obtain beneficial or desired results, including clinical results. For purposes of this invention, beneficial or desired clinical results include, but are not limited to, alleviation or amelioration of one or more symptoms of diminishment of extent of disease, delay or slowing of disease progression, amelioration, palliation or stabilization of the disease state, and other beneficial results described below.

"Pharmaceutically acceptable salt" refers to an acidic or basic salt that is toxicologically safe for administration to a subject, including without limitation, phosphate, sulfate, lactate, napsylate, mesylate, hydrochloride, sodium, potassium, n-methylglucamine, and tromethamine salts.

"Local administration," "topical administration," "topically," and grammatical equivalents, refer to administration of a biologically active compound to a pre-defined or definite area of the body, such as to a defined or limited area of the skin surface, mucous membrane, a specified organ, a specified appendage or region (e.g., foot). Local or topical administration, as used herein, does not include administration by subdermal injection.

"Fully soluble" or "completely dissolved" or "fully in solution" refers to a visually clear homogenous solution with substantially no suspended or undissolved particles of therapeutically active agents. A quantitative determination of solution clarity can be made by measurements of turbidimetry, e.g. the reduction of transparency of a liquid caused by the presence of undissolved matter (see Lawler, 1995, Turbidimetry and Nephelometry Encyclopedia of Analytical Science, ed. P. Worsfold, Academic Press Ltd, UK). Instruments such as the Model 2100AN or 2100N turbidimeter (Hach Co., Loveland, Colo.) may be used. Usually the turbidity of a composition containing a therapeutically active agent is less than about 10 NTU (nephelometric turbidity unit), more usually less than about 5 NTU or less than about 3 NTU.

"Stratum corneum" refers to the outer layer of the skin that is the primary bather layer. The stratum corneum creates the rate-limiting barrier for diffusion of an active agent across the skin.

"Penetration enhancer" refers to an agent that improves the rate of percutaneous transport of an active agent across the skin for use and delivery of active agents to organisms such as mammals.

An "individual" or "subject" is a vertebrate, preferably a mammal, and often a human. Mammals include, but are not limited to, humans, non-human primates, experimental model animals (e.g., mice and rats), agriculturally important animals, and pets.

As used herein, manufactured or formulated "under GMP standards," when referring to a pharmaceutical composition means the composition is in full compliance with all Good Manufacturing Practice (GMP) regulations of the U.S. Food and Drug Administration.

"Nerve fiber functionality (NFF)" is a measure of the functional or structural inactivation of nociceptive (TRPV1-expressing) sensory nerve fibers. A change in NFF can be expressed as a change in the density of functional nerve fibers identified by immunostaining and morphology, as described below. Alternatively, a change in NFF can be expressed as a change in a sensitivity of the nerve fiber (e.g., to changes in temperature).

As used herein, the terms "deliver," "delivering" and grammatical equivalents (e.g., as in "delivery of agonist to epidermis and dermis") refers to taking action that results in transfer of an agent (e.g., TRPV1 agonist) to a target tissue (e.g., epidermis and dermis). For example, capsaicin can be delivered to dermis by applying a capsaicin-containing composition of the invention to the unbroken surface of skin overlying the dermis.

As used herein, the term "retained" (e.g., as in "agonist retained in skin") refers to the amount of an agent found in a specified tissue (e.g., epidermis and dermis) at a specified point in time (e.g., 15 minutes after application of an agonist-containing composition).

The following conventions and abbreviations are used in the description below: Unless otherwise indicated, temperatures are in degrees centigrade and all measurements are made at 1 atmosphere and at a temperature of 23° C. to 32° C. Abbreviations used in this disclosure include "μL" (microliter); "mL" (milliliter); "nmole" (nanomole); "PE" (penetration enhancer); "TAA" (therapeutically active agent); weight/volume (w/v); volume/volume (v/v). References to a specified time after administration of a TRPV1 agonist-containing composition (e.g., "15 minutes") refer the the time beginning with the initial first contact of the composition with the subject (e.g., the time of application). If not otherwise specified or apparent from context, assays can be conducted 15 or 30 minutes after administering a composition, and values normalized to administration to a 1 cm² area.

3. TRPV1 Agonists

TRPV1 agonists useful in the present invention include capsaicin, capsaicin analogs and derivatives, and other low molecular weight compounds (i.e., MW<1000) that agonize the TRPV1. Capsaicin can be considered the prototypical TRPV1 agonist. Capsaicin (also called 8-methyl-N-vanillyl-trans-6-nonenamide; (6E)-N-[(4-hydroxy-3-methoxyphenyl)methyl]-8-methylnon-6-enamide; N-[(4-hydroxy-3-methoxyphenyl)methyl]-8-methyl-(6E)-6-nonenamide; N-(3-methoxy-4-hydroxybenzyl)-8-methylnon tran-6-enamide; (E)-N-[(4-hydroxy-3-methoxyphenyl)methyl]-8-methyl-6-nonenamide) has the following chemical structure:

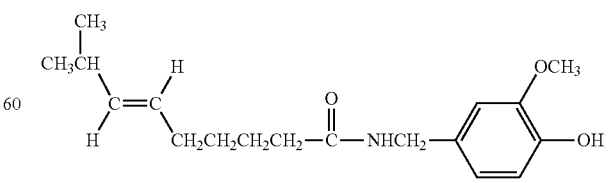

In addition to capsaicin, a variety of capsaicin analogs and derivatives, and other TRPV1 agonists may be administered. Vanilloids, such as capsaicinoids, are an example of useful TRPV1 agonists. Exemplary vanilloids for use according to the invention include N-vanillyl-alkanedienamides, N-vanillyl-alkanedienyls, N-vanillyl-cis-monounsaturated alkenamides, capsaicin, dihydrocapsaicin, norhydrocapsaicin, nordihydrocapsaicin, homocapsaicin, and homodihydrocapsaicin.

In another embodiment, the TRPV1 agonist is a compound lacking the vanillyl function, such as piperine or a dialdehyde sesquiterpene (for example warburganal, polygodial, or isovelleral). In another embodiment, the TRPV1 agonist is a triprenyl phenol, such as scutigeral. Additional exemplary TRPV1 agonists are described in U.S. Pat. Nos. 4,599,342; 5,962,532; 5,762,963; 5,221,692; 4,313,958; 4,532,139; 4,544,668; 4,564,633; 4,544,669; 4,493,848; 4,532,139; 4,564,633; and 4,544,668; and PCT publication WO 00/50387. Other useful TRPV1 agonists include pharmacolocally active gingerols, piperines, shogaols, and more specifically guaiacol, eugenol, zingerone, civamide, nonivamide, nuvanil, olvanil, NE-19550, NE-21610, and NE-28345 (see Dray et al., 1990, *Eur. J. Pharmacol* 181:289-93 and Brand et al., 1990, *Agents Actions* 31:329-40), resiniferatoxin, resiniferatoxin analogs, and resiniferatoxin derivatives (e.g., tinyatoxin). Any active geometric- or stereo-isomer of the forgoing agonists may be used.

Other TRPV1 agonists are vanilloids that have TRVP1 receptor-binding moieties such as mono-phenolic mono-substituted benzylamine amidated with an aliphatic cyclized, normal or branched substitution. Still other useful TRPV1 agonists for practicing the invention can be readily identified using standard methodology, such as that described in U.S. patent publication US20030104085. Useful assays for identification of TRPV1 agonists include, without limitation, receptor binding assays; functional assessments of stimulation of calcium influx or membrane potential in cells expressing the TRPV1 receptor, assays for the ability to induce cell death in such cells (e.g., selective ablation of C-fiber neurons), and other assays known in the art.

Mixtures of agonists and pharmaceutically acceptable salts of any of the foregoing may also be used. See Szallasi and Blumberg, 1999, *Pharmacological Reviews* 51:159-211, U.S. Pat. No. 5,879,696, and references therein.

4. Rapid and High Quantity Delivery of TRPV1 Agonists

The present invention relates, in part, to the discovery that administration of a TRPV1 agonist under conditions in which a significant amount of agonist is rapidly delivered to, and preferably retained in, the skin provides surprising benefits.

In one aspect, the invention provides a method for treating a capsaicin-responsive condition by administering a composition that contains a TRPV1 agonist and one or more penetration enhancers. In an embodiment, the composition delivers at least about 3 nmoles agonist to skin as measured in a mouse skin absorption assay. The mouse skin absorption assay is described in detail below. As discussed below, delivery of a specified molar amount of agonist to skin in a mouse skin absorption assay refers to the amount delivered per 1 $cm^2$ (as normalized from a 0.8 $cm^2$ area of skin used in the assay) in fifteen (15) minutes under the assay conditions.

In a related aspect, the invention provides a method of reducing the density of functional nociceptive nerve fibers in a selected tissue of a subject by contacting the tissue with a composition that contains a TRPV1 agonist and one or more penetration enhancers. In an embodiment, the composition delivers at least about 3 nmoles agonist to skin as measured in a mouse skin absorption assay.

In a related aspect, the invention provides a pharmaceutical composition containing a TRPV1 agonist and one or more penetration enhancers, where the composition delivers at least about 3 nmoles agonist to skin as measured in a mouse skin absorption assay.

In one embodiment of the invention, the TRPV1 agonist is capsaicin and the amount of agonist delivered is at least about 3 nmoles, at least about 6 nmoles, at least about 9 nmoles, at least about 16 nmoles, at least about 32 nmoles, at least about 49 nmoles, or at least about 65 nmoles as measured in a mouse skin absorption assay. In an embodiment, the TRPV1 agonist is capsaicin and the amount of agonist delivered is in the range of from about 3 nmoles to about 290 nmoles, such as a range bounded by a lower limit of 3 nmoles, 6 moles, 9 nmoles, 16 nmoles, 32 nmoles, or 49 nmoles, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles, where the upper limit is higher than the lower limit.

In a related embodiment of the invention, the TRPV1 agonist is an agonist other than capsaicin and the amount of agonist delivered as measured in a mouse skin absorption assay is at least about 3 nmoles, at least about 6 nmoles, at least about 9 nmoles, at least about 16 nmoles, at least about 32 nmoles, at least about 49 moles, or at least about 65 nmoles, or in the range of from about 3 nmoles to about 290 nmoles, such as a range bounded by a lower limit of 3 moles, 6 moles, 9 nmoles, 16 nmoles, 32 moles, or 49 nmoles, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles, where the upper limit is higher than the lower limit.

In a related embodiment of the invention, the TRPV1 agonist is an agonist other than capsaicin and the amount of agonist delivered as measured in a mouse skin absorption assay is the equivalent of at least about 3 nmoles capsaicin, at least about 6 nmoles capsaicin, at least about 9 nmoles capsaicin, at least about 16 nmoles capsaicin, at least about 32 nmoles capsaicin, at least about 49 nmoles capsaicin, or at least about 65 nmoles capsaicin, or in the range of from about 3 nmoles to about 290 moles capsaicin, such as a range bounded by a lower limit of 3 nmoles, 6 nmoles, 9 nmoles, 16 nmoles, 32 nmoles, or 49 nmoles capsaicin, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles capsaicin, where the upper limit is higher than the lower limit.

A molar amount of a TRPV1 agonist that is equivalent, as the term is used in this context, to a molar amount (e.g., 3 nmoles) of capsaicin can be determined using standard methodology. Since the potency and efficacy of TRPV1 agonists can vary, it is in some cases it is useful, upon determining an optimal delivery dose for capsaicin, to adjust the concentration or dosage of a TRPV1 agonist other than capsaicin. The number of moles of a non-capsaicin TRPV1 agonist which will produce the same degree of a biological effect (e.g., reduced nociceptive nerve fiber function) produced by 1 mole of capsaicin is referred to as the capsaicin equivalent ("CE"). The concept of CE is analogous to that of 'morphine equivalents' used to predict equivalent analgesic dose levels of various opioid analgesics (see, e.g., Kaiko, 1986, "Controversy in the management of chronic cancer pain: therapeutic equivalents of IM and PO morphine" *J Pain Symptom Manage.* 1:42-5; Hoskin et al., 1991, "Opioid agonist-antagonist drugs in acute and chronic pain states" *Drugs* 41:326-44). CE values are derived from both the potency and efficacy of the TRPV1 agonist, compared to capsaicin under identical assay conditions. One way to determine the relative potency and efficacy of TRPV1 agonists is to use a standardized in vitro assay, such as those based on Fluorometric Imaging Plate Reader (FLIPR) technology (Sullivan et al., 1999, "Measurement of [Ca2+] using the Fluorometric Imaging Plate Reader (FLIPR)" *Methods Mol Biol.* 114:125-33). FLIPR assays have been used widely to characterize and compare a large number of TRPV1 agonists (see, e.g., Smart et al., 2001, "Characterisation using FLIPR of human vanilloid VR1 receptor pharmacology." *Eur J Pharmacol.* 417:51-8; Witte et al., 2002, "Use of a fluorescent imaging plate reader-based calcium assay to assess pharmacological differences between the human and rat vanilloid receptor" *J Biomol Screen.* 7:466-475; and Behrendt et al., 2004, "Characterization of the mouse cold-menthol receptor TRPM8 and vanilloid receptor type-1 VR1 using a fluorometric imaging plate reader (FLIPR) assay" *Br J Pharmacol.* 141:737-45). One way to determine the CE value for a non-capsaicin TRPV1 agonist would be to combine the potency and efficacy of the compound by assigning values of 0.5 to both the potency and efficacy measured for capsaicin in a FLIPR assay (yielding a combined value of 1.0). Then the potency and efficacy values of another TRPV1 agonist is determined, and normalized to the 0.5 of capsaicin. The combined normalized value of another TRPV1 agonist is compared to the 1.0 of capsaicin to provide the approximate number of nmoles of the non-capsaicin TRPV1 agonist that is expected to produce the same effect as capsaicin on, for example, nerve fiber functionality (NFF) when applied.

In a further aspect of the invention, the composition delivers the TRPV1 agonist with a significant depot effect. As used herein, the "depot effect" refers to the retention of agonist in skin in a mouse skin assay, and is the ratio of the amount of agonist that passes out of skin to the amount retained in skin in the mouse skin absorption assay.

Thus, in an aspect the invention provides a method for treating a capsaicin-responsive condition by administering a composition that contains a TRPV1 agonist and one or more penetration enhancers, where the composition delivers 3 nmoles or more than 3 nmoles agonist to skin as measured in a mouse skin absorption assay, and where is significant proportion of the agonist is retained in the skin.

In a related aspect, the invention provides a method of reducing the density of functional nociceptive nerve fibers in a selected tissue of a subject by contacting the tissue with a composition that contains a TRPV1 agonist and one or more penetration enhancers where the composition delivers 3 nmoles or more than 3 nmoles agonist to skin as measured in a mouse skin absorption assay, and where a significant proportion of the agonist is retained in the skin.

In some embodiments, for example, the ratio of the amount of agonist that enters the receptor chamber in the mouse skin absorption assay to the amount retained in the skin is less than about 0.25, less than about 0.2, less than about 0.15, less than about 0.1, less than about 0.04, less than about 0.02, less than about 0.01, less than about 0.004, less than about 0.002, less than about 0.0015, or less than about 0.001. In some embodiments, the ratio of the amount of agonist that enters the receptor chamber in the mouse skin absorption assay to the amount retained in the skin at a specified time point is between about 0.0001 and about 0.25, often between about 0.0001 and about 0.2, sometimes between about 0.0001 and about 0.1, and sometimes between about 0.0001 and 0.04. In some embodiments, the ratio of the amount of agonist that enters the receptor chamber in the mouse skin absorption assay to the amount retained in the skin is between about 0.001 and about 0.25, often between about 0.01 and about 0.2, and sometimes between about 0.1 and about 0.25.

In one embodiment, the ratio of the amount of agonist in the dermis to the amount in the epidermis is in the range of 0.5 to 2, as measured in a mouse skin absorption assay. In some embodiments the ratio is in the range of 0.75 to 1.5.

In a related embodiment, the invention provides a method for treating a capsaicin-responsive condition by administering a composition that contains a TRPV1 agonist under conditions in which a significant amount of agonist is rapidly delivered to, and preferably retained in, a target tissue such as, but not limited to skin, mucosa, and endothelium). In another related embodiment, the invention provides a method for reducing the density of functional nociceptive nerve fibers in a selected tissue of a subject by contacting the tissue with a composition that contains a TRPV1 agonist under conditions in which a significant amount of agonist is rapidly delivered to, and preferably retained in, the target tissue. In an embodiment, "conditions in which a significant amount of agonist is rapidly delivered to the target tissue," refers to administration of a TRPV1 agonist under conditions that result in delivery of at least 3 nmoles agonist per cm$^2$ surface area of application (e.g., skin or mucosa surface area) within 30 minutes, more often within 15 minutes, and sometimes within 5 minutes.

In one embodiment, conditions in which a significant amount of agonist is rapidly delivered to the skin are defined as those measured in a human subject. In one embodiment the human subject is a subject in normal health. In one embodiment, the human subject is a subject in need of treatment for a capsaicin-responsive disease or condition. Thus, in one embodiment, the invention provides a method of reducing the density of functional nociceptive nerve fibers in a selected tissue region of a subject, by topically administering a significant amount of agonist to the region in less than about 30 minutes, optionally less than about 15 minutes, and optionally in less than about 10 minutes. A significant amount can be at least 3 nmoles, optionally at least 6 moles, at least about 9 nmoles, at least about 16 nmoles, at least about 32 nmoles, at least about 49 nmoles, or at least about 65 nmoles, or in the range of from about 3 nmoles to about 290 nmoles, such as a range bounded by a lower limit of 3 nmoles, 6 nmoles, 9 nmoles, 16 nmoles, 32 nmoles, or 49 nmoles, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles, where the upper limit is higher than the lower limit, per cm$^2$ of the surface of the region (e.g., skin, mucosa, and endothelium, e.g., bladder).

In an alternative embodiment, conditions in which a significant amount of agonist is rapidly delivered to the skin are defined as those measured in a mouse skin assay.

In one embodiment of the invention, the TRPV1 agonist is capsaicin and the amount of agonist delivered is at least about 3 nmoles, at least about 6 nmoles, at least about 9 nmoles, at least about 16 nmoles, at least about 32 nmoles, at least about 49 nmoles, or at least about 65 nmoles. In an embodiment, the TRPV1 agonist is capsaicin and the amount of agonist delivered is in the range of from about 3 nmoles to about 290 nmoles, such as a range bounded by a lower limit of 3 nmoles, 6 nmoles, 9 nmoles, 16 nmoles, 32 nmoles, or 49 nmoles, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles, where the upper limit is higher than the lower limit.

In a related embodiment of the invention, the TRPV1 agonist is an agonist other than capsaicin and the amount of agonist delivered is at least about 3 moles, at least about 6 nmoles, at least about 9 nmoles, at least about 16 nmoles, at least about 32 nmoles, at least about 49 nmoles, or at least about 65 nmoles, or in the range of from about 3 nmoles to about 290 nmoles, such as a range bounded by a lower limit of 3 nmoles, 6 nmoles, 9 nmoles, 16 nmoles, 32 nmoles, or 49 nmoles, and an independently selected upper limit of 6 nmoles, 9 nmoles, 16 nmoles, 32 nmoles, 49 nmoles, 65 nmoles, 75 nmoles, 90 moles, 120 moles, 200 nmoles and 290 nmoles, where the upper limit is higher than the lower limit.

In a related embodiment of the invention, the TRPV1 agonist is an agonist other than capsaicin and the amount of agonist delivered is the equivalent of at least about 3 nmoles capsaicin, at least about 6 nmoles capsaicin, at least about 9 nmoles capsaicin, at least about 16 nmoles capsaicin, at least about 32 nmoles capsaicin, at least about 49 nmoles capsaicin, or at least about 65 nmoles capsaicin, or in the range of from about 3 nmoles to about 290 nmoles capsaicin, such as a range bounded by a lower limit of 3 nmoles, 6 nmoles, 9 nmoles, 16 nmoles, 32 nmoles, or 49 nmoles capsaicin, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles capsaicin, where the upper limit is higher than the lower limit.

In a related embodiment, the invention provides a method for treating a capsaicin-responsive condition by administering a composition that contains a TRPV1 agonist under conditions in which a significant amount of agonist is delivered to and retained in the tissue. In another related embodiment, the invention provides a method for reducing the density of functional nociceptive nerve fibers in a selected tissue of a subject by contacting the tissue with a composition that contains a TRPV1 agonist under conditions in which a significant amount of agonist is delivered to and retained in skin. Systemic exposure to bolus doses of TRPV1 agonists poses safety risks for patients. This is because these receptors are expressed in nerve fibers which regulate the cardiovascular system (and other organ systems), so consequently a rapid activation of these nerves is expected to produce rapid changes in heart rate and blood pressure (Zahner et al., 2003, "Cardiac vanilloid receptor 1-expressing afferent nerves and their role in the cardiogenic sympathetic reflex in rats" *J Physiol.* 551:515-23). Such changes are problematic for elderly patients and those with pre-existing cardiovascular disease. Accordingly, the surprising discovery that high and rapid exposures of skin, mucous membranes, and other types of tissue to TRPV1 agonists could be attained as described here without an expectation of significant systemic drug delivery, allows topical application of TRPV1 agonist-containing formulations with relatively high safety margins. In one aspect the present invention provides a method of delivering a TRPV1 agonist to the epidermis and dermis underlying a 1 cm² area of a skin or mucosal surface of a mammal, by contacting the area with a composition comprising the TRPV1 agonist and at least one penetration enhancer, wherein 30 minutes after said contacting at least about 3 nmole of the TRPV1 agonist is retained in the epidermis and dermis. In a related embodiment, the invention provides a method of delivering a TRPV1 agonist to the epidermis and dermis underlying a 1 cm² area of a skin or mucosal surface of a mammal, by contacting the area with a composition comprising the TRPV1 agonist and at least one penetration enhancer, wherein 15 minutes after said contacting at least about 3 nmole of the TRPV1 agonist is retained in the epidermis and dermis. In various embodiments, the amount of TRPV1 agonist retained in the epidermis and dermis is at least about 3 nmoles, at least about 6 nmoles, at least about 9 nmoles, at least about 16 nmoles, at least about 32 nmoles, at least about 49 nmoles, or at least about 65 nmoles. In an embodiment, the TRPV1 agonist is capsaicin and the amount of agonist delivered is in the range of from about 3 nmoles to about 290 nmoles, such as a range bounded by a lower limit of 3 nmoles, 6 nmoles, 9 nmoles, 16 nmoles, 32 nmoles, or 49 nmoles, and an independently selected upper limit of 6 nmoles, 9 nmoles, 16 nmoles, 32 nmoles, 49 nmoles, 65 nmoles, 75 nmoles, 90 nmoles, 120 nmoles, 200 nmoles and 290 nmoles, where the upper limit is higher than the lower limit.

It will be understood that when measuring the agonist content of epidermis and dermis underlying a 1 cm² area, the actual cross section of tissue assayed can be less than (e.g., 0.8 cm²) or greater than 1 cm², and the measured agonist content can be normalized to an amount per cm².

In one embodiment, the agonist is contacted with the skin, mucosal or bladder surface in vitro (e.g., using a mouse skin absorption assay or similar assay). In another embodiment, the agonist is contacted with the skin, mucosal or bladder surface in vivo (e.g., by applying the composition to skin of a human or animal, such as mouse) and a tissue sample (e.g., of the skin surface and underlying dermis and epidermis) is obtained and agonist content determined. Tissue samples can be obtained using routine methods, such as punch biopsy or excision. Agonist content can be determined using quantiative methods such as HPLC-MS (see, Examples), as appropriate for the particular agonist used. Optionally, separate determinations can be made for the dermal and epidermal layers and the values combined.

In one embodiment the TRPV1 agonist is capsaicin.

In an embodiment, the mammal is a human subject. The human subject may be in normal health, or may suffer from a capsaicin-responsive condition.

In a further aspect, the amount of agonist delivered to the underlying tissue (dermis and epidermis) is sufficient to reduce the density of functional nociceptive nerve fibers in the epidermis and dermis (i.e., reduced nerve fiber function) by at least about 20% when measured 1, 2, 3, 4, 5, 6 or 7 days after said contacting step. In alternative embodiments the reduction is at least about 30%, at least about 40%, at least about 50%, at least about 60%, at least about 70%, or at least about 80% compared to an untreated region. It will be clear that when agonist concentration and NFF are determined in the same individual subject, the determinations are made using different tissues areas. More often, however, assays can be carried out in different subjects to establish that specified conditions of contacting (using a TRPV1 agonist in combination with compositions of the invention result in the specified delivery of agonist and/or reduction in NFF.

4.1 The "Mouse Skin Absorption Assay"

The "mouse skin absorption assay" is an in vitro Franz cell-based assay in which skin of Nu/Nu ("nude") mice is used to determine (1) the amount of agonist that enters the skin following administration of agonist to a 0.8 cm² area of skin surface for 15 minutes; (2) the proportion of agonist in the skin that is found in each of the epidermal and dermal layers; and (3) the amount of agonist that penetrates the skin (i.e., enters the receptor chamber of the Franz cell). This assay, which is described in detail in Example 1, infra, measures the amount of agonist that is retained in the dermis and epidermis fifteen (15) minutes after the surface of the skin is contacted with a composition containing the agonist. Consistent with reports that in vitro studies with nude mouse skin are predictive of the result obtained in living animals (Venter et al., 2001, "A comparative study of an in situ adapted diffusion cell and an in vitro Franz diffusion cell method for transdermal absorption of doxylamine" *Eur J Pharm Sci.* 13:169-77) delivery of TRPV1 agonist to skin in the mouse skin model correlates with reduction of nerve fiber functionality in vivo following administration of the agonist (see Examples, illustrating a relationship between delivery of a TRPV1 agonist into nude mouse skin in vitro and the pharmacological effects on cutaneous nerve fiber immunostaining in in vivo assays). In mammals, physical processes such as diffusion, partitioning and physical binding vary in a predictable manner (Franz et al., 1992, In: Treatise on Controlled Drug Delivery. Edited by A Kydonieus. Marcel Dekker, Inc. New York), and in vitro nude mouse skin studies are considered predictive of the penetration rates of drug substance and solvents in human skin (Durrheim et al., 1980, "Permeation of hairless mouse skin I: Experimental methods and comparison with human epidermal permeation by alkanols" *J. Pharm. Sci.* 69:781-6; see also Tojo, 1987, "Mathematical modeling of skin permeation of drugs" *J. Chem. Eng. Jpn.* 20:300-308; and Tojo, 1988, "Concentration profile in plasma after transdermal drug delivery" *Int. J. Pharm.* 43:201-205). Notably, the low density of hair follicles in hairless animal species such as the nude mouse brings these membranes closer in that respect to human skin (Katz, 1993, "Rationale and Approaches to Skin Permeation" In: Skin Permeation, Fundamentals and Application, Edited by J L. Zatz. Allured Publishing Corp. Wheaton, Ill.).

Using the mouse skin absorption assay, several values can be measured. The amounts of agonist that enter the epidermis ("E") and dermis ("D") can be measured. (In the values reported in the examples, the amount that enters the 0.8 $cm^2$ cross section of skin is normalized to 1 $cm^2$ by multiplying by 1.25). The ratio of these two values ("E/D"), referred to as the "distribution effect" is a measure of the relative distribution of agonist in the two skin layers, with equal distribution (on either a molar or mass basis, as specified) giving a ratio of 1. The sum of these two values (E plus D) is the total amount of agonist delivered to the skin ("S") under the assay conditions. The amount of agonist that passes through the skin and enters the receptor chamber of the Franz cell ("P") can also be measured. The ratio of the amount of agonist that passes through the skin to the amount that is retained in skin ("PIS") is referred to as the "depot effect" The units of E, D and S can be molar (e.g., nmole agonist) or weight (e.g., microgram agonist). E/D and P/S are unitless.

5. The Administered Composition

In one aspect of the invention, a TRPV1 agonist is administered as a composition ("the administered composition") containing at least one penetration enhancer. The applied composition of the invention can be described as having three components:
1. A solvent system in which the TRPV1 agonist is soluble, containing at least one penetration enhancer;
2. The TRPV1 agonist(s) and/or one or more additional therapeutically active agents;
3. Additional components that, if present, account for not more than 5% (w/v) of the composition.

In some embodiments of the invention the solvent system is characterized by having a high concentration of penetration enhancer(s).

5.1 Solvent System
5.1.1 Penetration Enhancers

A solvent system of the invention can contain a penetration enhancer or combination of penetration enhancers. Penetration enhancers are well known in the art, and are compositions that provide marked intradermal or percutaneous delivery of an agent (see Smith and Maibach, in *Percutaneous Penetration Enhancers*; CRC Press: Florida 1995; pp 1-8, e.g., Table 1; also see Barry, B. W. "Vehicle Effect: What Is an Enhancer?" In: TOPICAL DRUG BIOAVAILABILITY, BIOEQUIVALENCE, AND PENETRATION. Shah & Maibach. Eds. Plenum Press: New York, 1993; pp 261-76).

Without intending to be bound by a specific mechanism, penetration enhancers are believed to operate by several mechanisms, which include 'shunting' the drug substance through pores, sweat glands and hair follicles, and opening the intercellular spaces of the stratum corneum (Asbill et al., 2000, "Enhancement of transdermal drug delivery: chemical and physical approaches," *Crit Rev Ther Drug Carrier Syst.* 17:621-58). Regarding the latter, the proteinaceous intracellular matrices of the stratum corneum, together with the diverse biochemical environments of the intercellular domains in the stratum corneum, represent a formidable barrier to drugs before they can reach the deeper parts of epidermis (e.g., the stratum germinativum) and dermis. Once absorbed into the stratum corneum, effects of the penetration enhancer may include altering the solvent potential of the stratum corneum biochemical environment (i.e., the ability of stratum corneum to retain drug substances in a non-crystalline form), and disordering the ordered structure of the intercellular lipid region (for example, due to insertion of the enhancer molecule between the parallel carbon chains of the fatty acids). Exemplary penetration enhancers are listed, for illustration and not limitation, below (see, e.g., in Tables 1-3). Other penetration enhancers can be identified using routine assays, e.g., in vitro skin permeation studies on rat, pig or human skin using Franz diffusion cells (see Franz et al., "Transdermal Delivery" In: Treatise on Controlled Drug Delivery. A. Kydonieus. Ed. Marcell Dekker: New York, 1992; pp 341-421). Many other methods for evaluation of enhancers are known in the art, including the high throughput methods of Karande and Mitragotri, 2002, "High throughput screening of transdermal formulations" *Pharm Res* 19:655-60, and Karande and Mitragotri, 2004, "Discovery of transdermal penetration enhancers by high-throughput screening").

Penetration enhancers suitable for use in the present invention are pharmaceutically acceptable penetration enhancers. A pharmaceutically acceptable penetration enhancer can be applied to the skin of a human patient without detrimental effects (i.e., has low or acceptable toxicity at the levels used).

Penetration enhancers suitable for use in the present invention include, but are not limited to, enhancers from any of the following classes: fatty alcohols, fatty acids (linear or branched); terpenes (e.g., mono, di and sequiterpenes; hydrocarbons, alcohols, ketones); fatty acid esters, organic acids, ethers, amides, amines, hydrocarbons, alcohols, phenols, polyols, surfactants (anionic, cationic, nonionic, bile salts).

Penetration enhancers can be characterized by a variety of physical, as well as structural, properties. For example, in some embodiments of the present invention, a penetration enhancer component of the solvent system has a molecular weight not greater than 400, is liquid at room temperature, and has a vapor pressure less than 10 mm Hg at 32° C. Examples, for illustration and not limitation, of such compounds are provided in Table 1. (Tables 1-5 are provided at the end of the specification.)

In some embodiments of the present invention, a penetration enhancer component of the solvent system has a molecular weight not greater than 400, is liquid at room temperature, but which have a vapor pressure greater than 10 mm Hg. Penetration enhancers of this type usually constitute less than 100% (v/v) of the solvent system, more usually not more than 95% of the solvent system, even more usually not more than 75%, still more usually not more than 50% of the solvent system, and most usually these penetration enhancers contribute no more than about 30% (v/v) of the solvent system. Examples, for illustration and not limitation, of such compounds are provided in Table 2.

In some embodiments of the present invention, a penetration enhancer component of the solvent system is not liquid at room temperature (e.g., myristyl alcohol). Such "solid penetration enhancers" are not generally used as the sole component of the solvent system. However, a solvent system that contains a mixture of components can include a solid penetration enhancer(s), so long as the solid penetration enhancer itself is in a solution. For example, a solvent system containing 95% diethylene glycol monoethyl ether and 5% myristyl alcohol (where the myristyl alcohol is in solution) can be used. Penetration enhancers of this type usually constitute less than 100% (v/v) of the solvent system, more usually not more than 95% of the solvent system, even more usually not more than 75%, still more usually not more than 50% of the solvent system, and most usually these penetration enhancers contribute no more than about 30% (v/v) of the solvent system. Examples, for illustration and not limitation, of such compounds are provided in Table 3.

In some embodiments of the present invention, a penetration enhancer component of the solvent system has a molecular weight less than 50. Penetration enhancers of this type usually constitute less than 100% (v/v) of the solvent system, more usually not more than 95% of the solvent system, even more usually not more than 75%, still more usually not more than 50% of the solvent system, and most usually these penetration enhancers contribute no more than about 30% (v/v) of the solvent system.

In some embodiments of the present invention, a penetration enhancer component of the solvent system is a surfactant. In certain embodiments, the proportion of the solvent system that made up of surfactants is not more than 5% (v/v).

In some embodiments of the present invention, a penetration enhancer component of the solvent system is a urea. In certain embodiments, the proportion of the solvent system that made up of ureas is not more than 10% (v/v), or alternatively not more than 5% (v/v).

In one embodiment, the solvent system contains only one penetration enhancer. In a related embodiment, the solvent system contains two penetration enhancers, three penetration enhancers, four penetration enhancers, five penetration enhancers, or more than five penetration enhancers. Usually the solvent system contains one to four penetration enhancers.

Penetration enhancers particularly suited for use in the present invention include fatty alcohols and terpenes.

Examples of useful fatty alcohols useful as penetration enhancers include oleyl alcohol, elaidyl alcohol, linoleyl alcohol, elaidolinoleyl alcohol, linolenyl alcohol, elaidolinolenyl alcohol, cetyl-stearyl alcohol, lauryl-myristyl alcohol, octyl-decyl alcohol, octyl alcohol, decyl alcohol, myristyl alcohol, cetyl alcohol, stearyl alcohol, lauryl alcohol, 2-lauryl alcohol, ricinol alcohol, tallow alcohol, and caprylic alcohol.

Terpenes have molecular formulas $(C_nH_{2n-4})$, and are classified according to the number of isoprene units. Terpenes can occur theoretically in the following four configurations: (1) Three double bonds and no cycle (e.g., ocimene and myrecene), (2) Two double bonds and one cycle (e.g., limonene and Carveol), One double bond and two cycle (e.g., α-pinene or β-pinene and Limonene oxide). Sesquiterpenes have formula $(C_nH_{2n-6})$ and can theoretically occur in variety of configurations. Given the diverse nature of Terpenes and lack of strict definition of classification of terpenes, the foregoing description of terpenes and sesquiterpenes is not intended to restrict the invention in any manner.

Other examples include monoterpenes (2 isoprene units), sesquiterpenes (3 isoprene units), diterpenes (4, isoprene units), triterpenes (6 isoprene units) and tetraterpenes (8 isoprene units). Examples of monoterpenes are: nerol, citral, camphor, menthol. Examples of sesquiterpenes are: nerolidol, farnesol. Examples of diterpenes are: phytol, vitamin A1. Squalene is an example of a triterpene, and carotene (provitamin A1) is a tetraterpene. Examples, for illustration and not limitation, of terpenes useful as penetration enhancers include methylnoneonoic acid and methylnoneonoyl alcohol, oxide, cyclopentene oxide D-limonene, β-carene, α-terpineol, terpinen-4-ol, carvone, pulegone, piperitone, menthone, and 1,8-cineole. In one embodiment, terpenes used in the practice of the invention have a molecular weight less than 600. In one embodiment, terpenes used in the practice of the invention have a molecular weight greater than 100. In one aspect, the present invention provides a method of increasing the amount of a topically applied TRPV1 agonist that enters the epidermal and dermal layers by topically applying the molecule in a composition comprising a terpene. In an embodiment, the invention provides a pharmaceutical composition comprising a terpene and a TRPV1 agonist. in an embodiment, the TRPV1 agonist is capsaicin. In an embodiment, the terpene is methylnonenoic acid or methylnonenoyl alcohol. In another embodiment, the terpene is selected from the group consisting of α-pinene oxide, limonene oxide, cyclopentene oxide $_D$-limonene, α-pinene, β-carene, α-terpineol, teminen-4-ol, carvol, carvone, pulegone, piperitone, menthone, and 1,8-cineole.

One useful penetration enhancer of the solvent system is menthone. In some versions of the invention, the solvent system contains at least about 50%, at least about 70%, at least about 80%, at least about 90%, at least about 95%, or about 100% menthone.

Another useful penetration enhancer of the solvent system is methylnonenoic acid. In some versions of the invention, the solvent system contains at least about 50% (v/v), at least about 70%, at least about 80%, or at least about 90% methylnonenoic acid. In one aspect, the invention provides a pharmaceutical composition containing a TRPV1 agonist (e.g., capsaicin) and methylnonenoic acid.

Another useful penetration enhancer of the solvent system is methylnonenoyl alcohol. In some versions of the invention, the solvent system contains at least about 50% (v/v), at least about 70%, at least about 80%, or at least about 90% methylnonenoyl alcohol. In one aspect, the invention provides a pharmaceutical composition containing a TRPV1 agonist (e.g., capsaicin) and methylnonenoyl alcohol. In another aspect, the invention provides a method for increasing delivery of a TRPV1 agonist to a tissue (e.g., epidermis and/or dermis) by administering a composition containing the agonist and methylnonenoyl alcohol.

The use of methylnonenoyl alcohol and methylnonenoic acid to enhance dermal penetration of therapeutically active agents such as capsaicin has not previously been described. In one aspect, the present invention provides a method of increasing the amount of a topically applied molecule that enters the epidermal and dermal layers by topically applying the molecule in a composition comprising methylnonenoyl alcohol or methylnonenoic acid. In an embodiment, the molecule is a therapeutically active agent. In an embodiment, the molecule is a TRPV1 agonist.

Another useful penetration enhancer of the solvent system is cetyl alcohol. In some versions of the invention, the solvent system contains at least about 10% (v/v), at least about 20%, at least about 30%, or at least about 40% cetyl alcohol.

Another useful penetration enhancer of the solvent system is oleyl alcohol. In some versions of the invention, the solvent system contains at least about 50% (v/v), at least about 70%, at least about 80%, or at least about 90% oleyl alcohol.

Another useful penetration enhancer of the solvent system is propylene glycol. In some versions of the invention, the solvent system contains at least about 50% (v/v), at least about 70%, at least about 80%, or at least about 90% propylene glycol.

Another useful penetration enhancer of the solvent system is diethylene glycol monoethyl ether (DGME), which is commercially available as Transcutol® (Gattefossé Corp., Paramus, N.J.). In some versions of the invention, the solvent system contains at least about 70% (v/v), at least about 80%, at least about 90%, at least about 95%, or at least about 99% diethylene glycol monoethyl ether. In some embodiments of the invention, the solvent system does not contain DGME or DGME constitutes not more than 95% of the solvent system, alternatively not more than 75% of the solvent system, alternatively not more than 50% of the solvent system, and alternatively not more than about 30% (v/v) of the solvent system.

In some embodiments, the solvent system contains one, or two or more of the following penetration enhancers: menthone, methylnonenoic alcohol, methylnonenoic acid, oleyl alcohol, isopropyl myristate, dimethyl isosorbide, and propylene glycol.

Exemplary solvent systems contain the following combinations of penetration enhancers, with zero, or optionally one, two, three or more than three additional penetration enhancers: d-pipertone and oleic acid; 1-menthone and oleic acid; 1-menthone and ethyl oleate; 1-menthone and benzyl alcohol; ethylene glycol and 1-menthone; benzyl alcohol and oleyl alcoholic; 1-menthone and cetyl alcohol; 1,3-butandiol and oleic acid; diethylene glycol monoethyl ether and 1-menthone; ethelyne glycol and oleic acid; isopropyl myristate; oleyl alcohol and 1-3, butandiol; 1-menthone and isopropyl butyrate; 1-menthone and 1,3-butanediol; n-hexane and oleic acid; menthone and methanol; methylnonenoic acid and n-hexane; oleyl alcohol and propylene glycol; methylnonenoic alcohol and dimethylacetamide and Brij.

Exemplary solvent systems are (i) menthone 90% (v/v) plus methanol 10% (v/v); (ii) methylnonenoic acid 95% plus n-hexane 5%; (iii) oleyl alcohol 20% plus propylene glycol 80%; (iv) methylnonenoic alcohol 94% plus dimethylacetamide 5% plus Brij-35 1%. Capsaicin is expected to be stable for extended periods in these formulations, which are highly lipophilic and absorb little water. Additional exemplary solvent systems, for illustration and not limitation, are shown in Table 6.

When the solvent system contains more than one penetration enhancer, it is sometimes the case that one of the penetration enhancers predominates in the mixture. For example, in embodiments of the invention, the ratio of the predominant penetration enhancer to the sum of the other penetration enhancers in the solvent system is at least about 2:1, at least about 3:1; at least about 5:1, at least about 8:1, at least about 9:1 (v/v) or at least about 20:1. In one embodiment, the predominant penetration enhancer is diethylene glycol monoethyl ether. In one embodiment, the predominant penetration enhancer is menthone.

Exemplary penetration enhancers include stearyl alcohol, oleyl alcohol, linoleyl alcohol, linolenyl alcohol, caprylic alcohol, decyl alcohol, lauryl alcohol, Propylene glycol, polyethylene glycol, ethylene glycol, diethylene glycol, triethylene glycol, ethoxy digkycol, dipropylene glycol, glycerol, propanediol, butanediol, pentanediol, hexanetriol 2-lauryl alcohol, myristyl alcohol, cetyl alcohol, capric acid, lauric acid, myristic acid, stearic acid, oleic acid, caprylic acid, valeric acid, heptanoic acid, pelagonic acid, caproic acid, isovaleric acid, neopentanoic acid, trimethyl hexanoic acid, neodecanoic acid, isostearic acid, neoheptanoic acid, neononanoic acid, isopropyl n-decanoate, isopropyl palmitate, octyldodecyl myristate, ethyl acetate, butyl acetate, methyl acetate, isopropyl n-butyrate, ethylvalerate, methylpropionate, diethyl sebacate, ethyl oleate, isopropyl n-hexanoate, isopropyl myristate, urea, dimethylacetamide, diethyltoluamide, dimethylformamide, dimethyloctamide, dimethyldecamide, 1-hexyl-4-methoxycarbonyl-2-pyrrolidone, 1-lauryl-4-carboxy-2-pyrrolidone, 1-methyl-4-carboxy-2-pyrrolidone, 1-alkyl-4-imidazolin-2-one, 1-methyl-2-pyrrolidone, 2-pyrrolidone, 1-lauryl-2-pyrrolidone, 1-hexyl-4-carboxy-2-pyrrolidone, 1-methyl-4-methoxycarbonyl-2-pyrrolidone, 1-lauryl-4-methoxycarbonyl-2-pyrrolidone, dimethylsulfoxide, decylmethylsulfoxide, N-cocoalkypyrrolidone, N-dimethylaminopropylpyrrolidone, N-tallowalkylpyrrolidone, N-cyclohexylpyrrolidone, 1-famesylazacycloheptan-2-one, 1-geranylgeranylazacycloheptan-2-one, fatty acid esters of -(2-hydroxyethyl)-2-pyrrolidone, 1-geranylazacycloheptan-2-one, 1-dodecylazacycloheptane-2-one (Atone), 1-(3,7-dimethyloctyl) azacycloheptan-2-one, 1-geranylazacyclohexane-2-one, 1-(3,7,11-trimethyldodecyl)azacyclohaptan-2-one, 1-geranylazacyclopentan-2,5-dione, 1-famesylazacyclopentan-2-one, benzyl alcohol, butanol, pentanol, hexanol, octanol, nonanol, decanol, ethanol, 2-butanol, 2-pentanol, propanol, diethanolamine, triethanolamine; hexamethylenelauramide and its derivatives, benzalkonium chloride, sodium laurate, sodium lauryl sulfate; cetylpyridinium chloride, citric acid, succinic acid, salicylic acid. sylicylate Cetyltrimethyl ammonium bromide, tetradecyltrimethylammonium bromide; octadecyltrimethylammonium chloride; dodecyltrimethylammonium chloride, hexadecyltrimethylammonium chloride, Span 20, Span 40, Span 60, Span 80, Span 85, Poloxamer231, Poloxamer182, Poloxamer184), Brij 30, Brij 35, Brij 93, Brij 96, Span 99, Myrj45, Myrj51, Myrj52, Miglyol 840, glycholic, sodium salts of taurocholic, lecithin, sodium cholate, desoxycholic acids, D-limonene, α-pinene, β-carene, α-terpineol, terpinen-4-ol, carvol, carvone, pulegone, piperitone, Ylang ylang, menthone, anise, chenopodium, eucalyptus, limonene oxide, α-pinene oxide, cyclopentene oxide, 1,8-cineole, cyclohexene oxide, N-heptane, N-octane, N-nonane, N-decane, N-undecane, N-dodecane, N-tridecane, N-tetradecane, N-hexadecane, and essential oils (e.g., tea tree oils).

As discussed below, in some embodiments the solvent system may contain elements other than the penetration enhancer(s), such as water or other excipient. In some embodiments, the penetration enhancer (if the solvent system contains only one penetration enhancer) or penetration enhancers together (if the solvent system contains more than one penetration enhancer) account for at least about 20% of the volume of the solvent system. Often the penetration enhancer(s) account for at least about 40% of the volume of the solvent system, often at least about 50% of the volume of the solvent system, often at least about 75% of the volume of the solvent system, often at least about 80% of the volume of the solvent system, often at least about 90% of the volume of the solvent system, often at least about 95% of the volume of the solvent system, often at least about 98% of the volume of the solvent system, sometimes at least about 99% of the volume of the solvent system, sometimes at least about 99.5% of the volume of the solvent system, and sometimes 100% of the volume of the solvent system.

5.1.2 Other Components of the Solvent System

In some embodiments of the invention, the solvent system contains liquid components (water, saline, etc.) in addition to a penetration enhancer or combination of penetration enhancers. In some embodiments of the invention, the solvent system is biphasic and the TRPV1 agonist is soluble in at least one phase. In an embodiment solvent system is monophasic.

5.2 TRPV1 Agonist and/or Other Therapeutically Active Agents 5.2.1 Administration of TRPV1 Agonists Exemplary TRPV1 agonists are described above (Section 3). In some embodiments of the invention the administered composition also contains one or more additional therapeutically active agents that are co-administered with the TRPV1 agonist(s).

Using the methods and compositions disclosed herein, therapeutically effective amounts of TRPV1 agonists such as capsaicin can be administered (e.g., topically) to a subject much more rapidly than is possible using conventional formulations. Capsaicin-mediated therapeutic benefits (including reduction of the density of cutaneous or mucosal nociceptors and amelioration of capsaicin-responsive conditions and/or their characteristic symptoms) can be achieved by administration of capsaicin at a lower concentration and/or for a shorter period than heretofore believed or demonstrated. For some applications it will be desirable to use a relatively high concentration for a short time, while in other cases there will be advantages to using a lower concentration. The concentration of TRPV1 agonist in the composition can range from 0.05 to 60% w/v, depending on the specific TRPV1 agonist, solvent system used, and desired outcome.

In some embodiments, the concentration of TRPV1 agonist in the composition of the invention is in the range about 1% (w/v) to about 40%, about 5% to about 25%, about 10% to about 20%, or about 15%.

In one embodiment, the concentration of TRPV1 agonist is less than about 3% (w/v). In some embodiments, the concentration of TRPV1 agonist in the composition of the invention is in the range about 0.001% to about 20%, about 0.05% to about 20%, about 0.1% to about 10%, or about 0.1% to about 5%. In one embodiment, the concentration of TRPV1 agonist is less than about 3%. Other exemplary ranges are from about 0.001% to about 0.09%, about 0.001% to about 0.05%, about 0.001% to about 0.5%, from about 0.01% to about 1%, about 1% to about 5%, about 1% to about 10%, about 2% to about 7%, and about 2% to about 5%. In various embodiments, the TRPV1 agonist is present at a concentration in a range bounded by a lower limit of 0.001%, 0.010%, 0.05%, 0.1%, 0.5%, 0.75%, 1%, 2%, 3%, 4%, 5%, 6%, 7%, 7.5%, or 10% and an independently selected upper limit of 0.010%, 0.05%, 0.5%, 1% 2%, 3%, 4%, 5%, 6%, 7%, 7.5%, 10%, 20%, 30%, 40%, 50% or 60% (where the upper limit is greater than the lower limit).

In one embodiment, capsaicin (or a capsaicin analog) at a concentration of less than 5% (w/v), less than about 3%, less than about 2%, less than about 1%, or less than about 0.5%.

Usually, the concentration of TRPV1 agonist is such that a therapeutically effective dose of the TRPV1 agonist can be delivered in a volume that is conveniently applied to the skin of the subject (e.g., usually a volume of from about 5 µL to 50 µL per 1 cm$^2$, often a volume of about 50 µL per 1 cm$^2$, often about 25 µL per 1 cm$^2$, often about 10 µL per 1 cm$^2$, often between about 5 µL and 25 µL per 1 cm$^2$ or about 5 µL and 10 µL per 1 cm$^2$).

In one embodiment, a composition of the invention contains more than one TRPV1 agonist (e.g., two, three, four, or more TRPV1 agonists). In one embodiment, the composition contains capsaicin and another TRPV1 agonist. Usually the combined concentration of TRPV1 agonists in the composition is 0.05 to 60% w/v, more often 0.05% to 10%, frequently 0.1% to 15%, 0.1% to 10%, or 1% to 10%. In one embodiment, the composition of the invention contains a single TRPV1 agonist. In one embodiment, the TRPV1 agonist is capsaicin.

5.3 Therapeutically Active Agents Other than TRPV1 Agonists

In some embodiments, the administered composition includes one or more additional therapeutically active agents ("TAA") that are co-administered with the TRPV1 agonist(s). As used herein, the term therapeutically active agent refers to an agent, other than a TRPV1 agonist, with a biologically desirable activity that can be administered to a subject by topical application to the skin, eyes, or to oral or nasal mucosa. Typically, the TAA has a molecular weight less than 1000, often less than 500. It will be understood that penetration enhancers, vehicles, solvents and the like are not examples of TAAs.

In one embodiment an additional therapeutically active agent co-administered with the TRPV1 agonist(s) is a local anesthetic. Exemplary local anesthetics include, without limitation, acetamidoeugenol, alfadolone acetate, alfaxalone, amucaine, amolanone, amylocaine, benoxinate, benzocaine, betoxycaine, biphenamine, bupivacaine, burethamine, butacaine, butaben, butanilicaine, buthalital, butoxycaine, carticaine, 2-chloroprocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, ketamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, and zolamine, and combinations thereof.

In other embodiments, the additional therapeutically active agent(s) co-administered with the TRPV1 agonist(s) are other than a local anesthetic. For example and not limitation, the TAA can be a steroid, a non-steroidal anti-inflammatory drug (e.g., ibuprofen, ketoprofen, flurbiprofen, naproxen, ketorolac and diclofenac), opioid analgesic (e.g., fentanyl and buprenorphine), antineoplastic agent (e.g., 5-flurouracil), or any of a variety of other drugs. Generally, the TAA is an agent for which local (e.g., dermal) administration is desired.

The concentration of the TAA in the composition can range from 0.05 to 60% w/v, depending on the specific TAA and the solvent system used. The concentration of TAA in the composition is usually in the range about 0.05% to about 10%, often in the range about 0.1% to about 10%, and most often in the range about 0.1% to about 5%. Usually, the concentration is such that a therapeutically effective dose of the TAA can be delivered in a volume that is conveniently applied to the skin of the subject (e.g., usually a volume of between about 0.05 mL and 10 mL, more often between about 0.1 mL and 5 mL, even more often between about 0.25 mL and 1 mL.)

In various embodiments, the TRPV1 agonist is at a concentration in a range bounded by a lower limit of 0.001% (w/v), 0.010%, 0.05%, 0.1%, 0.5%, 1%, 2%, 3%, 4%, 5%, 6%, 7%, 7.5%, or 10% and an independently selected upper limit of 0.001%, 0.010%, 0.05%, 0.1%, 0.5%, 1%, 2%, 3%, 4%, 5%, 6%, 7%, 7.5%, 10%, 20%, 30%, 40%, 50% or 60% (where the upper limit is greater than the lower limit) and the local anesthetic is at a concentration in a range bounded by a lower limit of 0.1%, 0.5%, 1%, or 2% and an independently selected upper limit of 0.5%, 1%, 2%, 5% or 10% (where the upper limit is greater than the lower limit). In an embodiment, the local anesthetic is tetracaine. Usually, the combined concentration of TRPV1 agonist and other TAA(s) is in the range 0.05 to 60% w/v, more often 0.05% to 10%, and frequently 0.1% to 10%.

5.4 Administration of Therapeutically Active Agents Other than TRPV1 Agonists

In a related aspect of the invention, a therapeutically active agent other than a TRPV1 agonist is administered as a composition that includes a solvent system as described elsewhere herein with respect to administered compositions of the invention. Thus, the TAA composition has the following:

1. A solvent system in which the TAA is soluble, containing at least one penetration enhancer;
2. One or more TAAs;
3. Additional components that, if present, account for not more than 5% (w/v) of the composition.

In preferred embodiments, the solvent system is characterized by having a high concentration of penetration enhancer(s), such as at least about 50%, at least about 75%, at least about 85%, at least about 90%, at least about 95%, at least about 99%, at least about 99.5%, or 100%.

Exemplary TAAs that can be administered using the compositions include those listed in Section 5.2, supra, and are typically agents for which local (e.g., dermal) administration is desired and are often drugs that act at a site very close to the site of administration (e.g., local anesthetics).

5.5 Other Components of the Administered Composition

The composition may also contain stabilizers, pH modifiers, colorants and fragrance or other compounds. These components account for less than about 5% (w/v) of the composition, more often less than about 2%, and often less than about 1% or even about 0.5% of the composition.

Stabilizers useful in the compositions include materials that aid in ensuring a stable composition (e.g., maintenance of viscosity over time, maintenance of pH over time, or maintenance of purity, appearance, homogeneity, and/or color over time) and/or prevent growth of bacteria or other microorganisms and/or to maintain the chemical stability of the agonist or other therapeutically active agent against hydrolysis, oxidation, thermal or photolytic degradation. Exemplary stabilizers include antioxidants, chelators, preservatives (e.g., disodium edetate, beta-carotene, tocopherols, beta-tocopherols, tocopherol acetate, octyl gallate, ascorbyl palmitate, butylated hydroxyanisole, butylated hydroxytoluene); antimicrobial agents (i.e., include any compound effective in reducing or preventing build up of microbial load in the formulation, e.g., parabens, methylparaben, propylparaben, butylparaben, methyl salicylate, phenethyl alcohol, and resorcinol); and other agents (see, e.g., U.S. Pat. Nos. 6,013,270 and 6,390,291).

5.6 Optional Agents not Generally Required and Sometimes Omitted or Present in Only Small Amounts Topically administered agents are often administered in moderate to high viscosity forms (e.g., as a gel, lotion or cream) or via a topical or transdermal patch. In some embodiments of the invention, a composition of the invention is an "immediate-release composition" in which all or most (i.e., entire dose) of the therapeutic agent is available at the site of administration (e.g., skin, mucosa or epithelial surface) rather than administered over a sustained period. In some embodiments, the composition is a low viscosity composition (i.e., TRPV1 agonists are delivered in a low viscosity composition). As used in this context, a low viscosity composition is one having a viscosity less than about 5000 centipoise (cps), sometimes less than about 1000 cps, less than about 500 cps, less than about 100 cps, less than about 50 cps, less than about 40 cps, less than about 20 cps, or less than about 10 cps when measured before application to the skin, or alternatively, when measured at 32° C. (skin temperature). Viscosity can be measured using standard methods, e.g., by cone-and-plate viscometer or coaxial-cylinder viscometer. Transdermal patches (e.g., reservoir, matrix and micro reservoir patches) are widely used for drug delivery, and are generally occlusive and/or adherent devices. In addition, compositions delivered by patches are by nature "delayed release" compositions. Administration of a therapeutic agent without the use of an occlusive patch device is referred to as "non-occlusive" administration or contacting. Administration of a therapeutic agent without the use of a skin-adherent device is referred to as "non-adherent" administration or contacting. A therapeutic agent administered without the use of a delayed release mechanism is referred to as an "immediate release" composition. In certain embodiments of the present invention, TRPV1 agonists are delivered without the use of a transdermal patch device and/or without the use of any occlusive and/or without the use of adhesive and/or as immediate delivery compositions." In an embodiment, the TRPV1 agonist of the administered composition enters tissue passively (i.e., without the use of an occlusive material to increase speed of entry).

Thus, in some embodiments of the invention, the administered composition is free from agents generally added to compositions for topical administration to increase viscosity or otherwise maintain contact of a topically administered agent to the skin surface for an extended period and/or added to modify flow characteristics to facilitate application to a defined area, or, if present, such agents are present at only very low amounts (e.g., less than about 3% (w/v), less than about 1%, usually less than about 0.5%, and most usually less than 0.1%). For example, in some embodiments, ethyl cellulose can be included, if at all, at a concentration of less than 1%, more usually less than 0.5%, most usually less than 0.1% or less than 0.05%.

Thus, in some embodiments, the administered composition has very low viscosity and is free, or substantially free (which, in this context, means less then 0.1% w/v) of thickeners and gelling agents such as alkene copolymers (e.g., butylene-ethylene-styrene copolymer or ethylene-propylene-styrene copolymer), cross-linked polyacrylate polymers, carboxylic acid polymers, polyacrylamide polymers, acrylic acid/ethyl acrylate copolymers, carboxyvinyl polymers, Carbopol™ resins (colloidally water-soluble polyalkenyl polyether crosslinked polymer of acrylic acid cross-linked with a cross-linking agent such as polyallyl sucrose or polyallyl pentaerythritol), acacia, agar, alginic acid, aluminum, monostearate, attapulgite (activated or colloidal activated), bentonite, purified bentonite, bentonite magma, carboxymethylcellulose calcium, carboxymethylcellulose sodium, carboxymethylcellulose sodium 12, carrageenan, microcrystalline cellulose, carboxymethylcellulose sodium, dextrin, gelatin, guar gum, hyaluronic acid, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, viscous silicone oil (>5000 cps), silicone-based gels, sodium alginate, tragacanth, xanthan gum, and aluminum silicates.

5.7 The Form of the Administered Composition

In some embodiments of the invention, the administered composition is form suitable for administration to a subject (e.g., human patient). In one embodiment, the composition is provided in a unit dosage form or multiunit dosage form. As used herein, a unit dosage form means an amount of the administered composition suitable for a single administration to a single subject in need of treatment, and multiunit dosage form means an amount of the administered composition suitable for a multiple administrations (e.g., usually from 2 to 10 administrations, more usually from 2 to 5 administrations, even more usually from 2 to 4 administrations and most usually 2 or 3 administrations). The unit dosage form and multiunit dosage form may be in the form of a liquid solution in one or more vials or similar containers. Typically the content of each vial will be between 0.1 mL and 100 mLs, more often from 0.5 to 50 mL, more often from 1 to 10 mL. In some embodiments, the unit dosage or multiunit dosage is contained in a syringe, a dropper, a pipette or other liquid delivery device. In some embodiments, the unit dosage or multiunit dosage is contained in a spray or aerosol delivery device. In some embodiments, the unit dosage or multiunit dosage is contained in a syringe. In some embodiments the unit dosage or multiunit dosage is in the form of a towelette or other absorbent material impregnated with the administered composition. In one embodiment, each unit dosage or multiunit dosage is individually packaged in a package suitable for storage and/or shipping.

6. Properties of Administered Composition and Solvent System

This section describes additional properties of certain administered compositions that may be used in the practice of the invention. These properties may be used in selecting combinations of penetration enhancer(s) and other composition components for optimized use with a particular type and concentration of agonist. However, the useful compositions of the invention are not limited to compositions having all of the exemplary properties described below.

6.1 The Administered Composition and Solvent System May be Liquid Solutions in which the TRPV1 Agonist(s) are Soluble As noted above, the TRPV1 agonist is dissolved in the solvent system in an amount and at a concentration that will vary according to the particular agonist, other TAAs present, the purpose of the composition, and the desired dose. In a preferred embodiment, will be appreciated, however, that in the present invention, the TRPV1 agonist is fully in solution in the solvent system (e.g., present in an amount that is lower than the saturation limit of the TRPV1 agonist in the solvent system). Shaking, heating, sonication and the like may be used to drive an agonist into solution, so long as the agonist remains in solution at room or skin temperature after preparation.

The compositions of the present invention may be homogenous solutions with substantially all of the TRPV1 agonist dissolved in the composition (and often dissolved in the solvent system component of the composition), and substantially no suspended or undissolved particles of agonist. While the present invention is not limited to compositions displaying only particular maximum level of turbidity, those of skill in the art will understand that generally, turbidity is minimal.

6.2 The Composition May be Applied as a Thin Film

Some compositions of the invention can be applied as a thin homogeneous film, which does not require occlusion, bioadhesives, or other additives or devices to effect pharmacological action. The formulation may be applied through physical mechanical means including swab, applicator pad, syringe spreader, or like devices intended to apply liquids in a thin film. Since the administered compositions of the invention are typically applied to skin at a dose of about 10 µL per cm$^2$, sometimes ranging up to 20 or 30 µL per cm$^2$, these applications result in a composition film thickness of about 100-300 µm.

Generally, the compositions of the invention are applied in a liquid volume of at least about 5 µl/cm$^2$ application area (e.g., skin or mucosal surface), often at least about 7.5 µl/cm$^2$ application area, at least about 10 µl/cm$^2$ application.

The compositions result in a thin layer of a low viscosity homogeneous liquid adsorbed to micro skin-surface irregularities and flowing with body shape. The coverage, wetting and intrinsic contouring given by liquid topical applications, allows for maximum surface exposure due to rheological and thermodynamic properties of a low viscosity fluid. The compositions demonstrate expected behaviors such as an initial wetting sheen followed by gradual dissipation. Application as a thin film may contribute to the ability of the formulations to depot in skin in very short application durations.

6.3 The Composition May Disappear Rapidly Following Application

Some compositions of the invention are characterized by rapid and substantially complete disappearance from the surface of the skin following application. In one embodiment, for example, the composition substantially disappears (e.g., is absorbed and/or is evaporated) within about 30 minutes (and more usually within 15 minutes, 10 minutes, often within about 5 minutes, often within about 2 minutes, and sometimes even within 1 minute) after application of about 5 µL or 10 µL to skin (e.g., forearm) per cm² skin area (e.g., 250 µL per 25 cm²). By "substantially disappears" is meant that the majority (usually at least about 75%, at least about 90% or at least about 95%) of the composition applied topically has dispersed by absorption through the stratum corneum into the epidermis or dermis of the skin and/or by evaporative processes (e.g., as assessed by disappearance from the surface site of application, e.g., the skin surface is dry to the touch or as assessed by other quantitative or qualitative methods). In one embodiment the disappearance is primarily or completely due to absorption (e.g., the majority, or even at least about 75%, of the composition applied topically has dispersed by absorption). In another embodiment, the disappearance is primarily or completely due to absorption. In an embodiment, at least about 5 µL of the composition is delivered to (absorbed into) each cm² of the skin or other treated region within about 15 minutes.

6.4 the Penetration Rate of the Composition May be Greater than the Evaporation Rate Some compositions of the invention are characterized by having a penetration rate that is greater than its evaporation rate. As used herein, the term "penetration rate" refers to the rate at which the composition penetrates the barrier of the stratum corneum and is absorbed into the skin. As used herein, the term "evaporation rate" refers to the rate at which the components of the formulation undergo a phase change from liquid to gaseous form. When the composition evaporation rate is greater than its penetration rate, it is especially likely that significant agonist will remain on the skin surface. Stated differently, when the vapor pressure of the composition is high, and hence its evaporation rate exceeds percutaneous penetration, a significant residue of therapeutic agent may remain as a residual deposit on the skin surface.

The relative penetration and evaporation rates of a composition may be determined by a variety of methods including those described by B. W. Kemppainen and W. G. Reifeinrath in METHODS FOR SKIN ABSORPTION, CRC Publication 1990. Evaporation/permeation analysis systems are available from Laboratory Glass Apparatus, Inc. Berkeley, Calif.

7. Methods of Making Compositions

The compositions of the invention can be made using conventional techniques. Materials can be combined in any order. Illustrative preparation methods for certain forms of the composition are described hereinbelow.

In one embodiment, the components are manufactured or formulated in full compliance with all Good Manufacturing Practice (GMP) regulations of the U.S. Food and Drug Administration using materials suitable for administration to human subjects.

8. High Flux Rate Application

In another aspect, the invention provides a method of treating a capsaicin-responsive condition in a subject by topical administration of a composition containing a TRPV1 agonist under conditions in which the agonist penetrates the stratum corneum at a high flux rate. When administered at a high flux rate, the rapid exposure of nerve fibers to capsaicin and/or rapid accumulation of capsaicin in the epidermis or dermis results in a substantial reduction in density of functional cutaneous nociceptors.

Flux rate refers to the movement of a compound (e.g., TRPV1 agonist) across a barrier (e.g., stratum corneum) and has units of weight/area/unit time (e.g., µg/cm²/10 minutes).

As used in this context, "a high flux rate" means a flux rate of at least about 10 µg/cm²/15 minutes, preferably at least about 10 µg/cm²/10 minutes, even more preferably 20 µg/cm²/15 minutes, or even at least about 35 µg/cm²/15 minutes or at least about 35 µg/cm²/10 minutes, and sometimes even at least about 50 µg/cm²/15 minutes, at least about 75 µg/cm²/15 minutes, or at least about 100 µg/cm²/15 minutes. A "high flux rate" also means a flux rate of at least about 1 µg/cm²/minute, preferably at least about 2 µg/cm²/minute, at least about 3.5 µg/cm²/minutes, at least about 5 µg/cm²/minute, at least about 7.5 µg/cm²/minute, or at least about 10 µg/cm²/minute.

In one embodiment, the invention provides a method of treating a capsaicin-responsive condition in a subject by topical administration of a composition containing TRPV1 agonist at a concentration of less than 5% (w/v), usually less than about 3%, often not more than about 1%, often less than about 1%, often less than about 0.5%, and sometimes less than about 0.1 or 0.05% under conditions in which the agonist penetrates the stratum corneum at a high flux rate.

In one embodiment, the invention provides a method of treating a capsaicin-responsive condition in a subject by topically administering a composition containing a TRPV1 agonist at a high flux rate, wherein said administering is for less than about 45 minutes, preferably less than about 30 minutes, often about less than about 15 minutes, sometimes about 10 minutes or less, or even less than about 5 minutes. In an embodiment, the composition administered contains capsaicin at a concentration of less than 5% (w/v), usually less than about 3%, often not more than about 1%, often less than about 1%, often less than about 0.5%, and sometimes less than about 0.1 or 0.05%.

In one embodiment, the invention provides a method of substantially reducing the density of functional cutaneous nociceptors in a topical area of a subject by topically administering a composition containing a TRPV1 agonist at a high flux rate where administration is for less than about 45 minutes, preferably less than about 30 minutes, often about less than about 15 minutes, sometimes about 10 minutes or less, or even less than about 5 minutes. In an embodiment, the composition administered contains TRPV1 agonist at a concentration of less than 5% (w/v), usually less than about 3%, often not more than about 1%, often less than about 1%, often less than about 0.5%, sometimes less than about 0.1, and sometimes less than about 0.05%.

9. Administration of Composition 9.1 Duration of Administration

Depending on the purpose of administration and/or the condition being addressed, administration of the compositions of the invention can have a variety of beneficial effects, including a reduction in nerve fiber functionality, a change in skin sensitivity, relief from pain, and other beneficial effects. Unexpectedly, these beneficial effects usually can be accomplished by a relatively short exposure to the composition. For example, the duration of administration sufficient to result in beneficial effect is usually less than one hour, more often less than 30 minutes, sometimes less than about 15 minutes, and sometimes less than about 10 minutes, sometimes about 5 minutes or less, and sometimes less than about 2 minutes. Using the methods and compositions disclosed herein, therapeutically effective amounts of TRPV1 agonists such as capsaicin can be topically administered to a subject much more rapidly and is greater amounts than is possible using conventional formulations.

In one embodiment, the invention provides a method of reducing chronic pain in a subject by topical administration of a TRPV1 agonist-containing composition of the invention for less than about 45 minutes, usually less than about 30 minutes, often about less than about 15 minutes, sometimes about 10 minutes or less, or even less than about 5 minutes. Generally one or two administrations are sufficient to provide persistent relief.

As used herein, the duration of administration can refer to the time elapsed between first application of the composition to the subject (e.g., by spraying onto skin, by immersion, or the like, and either (1) ending contact (e.g., removing an immersed body part from a bath, removing an applicator device from the skin, and the like; (2) cleaning the region contacted with the composition to remove any residual agonist (e.g., using a cleaning solution as described below in Section 10); or (3) the point at which the composition has entirely disappeared from the site of application (e.g., by absorption into the skin, evaporation, or a combination of both).

9.2 Administration to Skin

The compositions of the invention may be applied to the skin (or, alternatively, to mucous membrane) using a large variety of methods and devices. For example and not illustration, compositions may be administered using a sponge, aerosol, spray, brush, swab, or other applicator. In one embodiment, the applicator provides either a fixed or variable metered dose application such as a metered dose aerosol, a stored-energy metered dose pump or a manual metered dose pump. In an embodiment, the applicator device has measuring marks for assisting a user in determining the amount of the composition in the applicator device.

In one embodiment, the applicator is non-occlusive. In one embodiment, the applicator does not adhere to the skin and/or is not adhesive. In one embodiment, the applicator is not a patch device. In one embodiment, the applicator is a patch device and does not contain a penetration enhancer selected from the group butanediols, dipropylene glycol, tetrahydrofurfuryl alcohol, diethylene glycol dimethyl ether, diethylene glycol monoethyl ether, diethylene glycol monobutyl ether, propylene glycol, dipropylene glycol, carboxylic acid esters of tri- and diethylene glycol, polyethoxylated fatty alcohols of 6-18 C atoms, 2,2-dimethyl-4-hydroxymethyl-1,3-dioxolane, dipropylene glycol, 1,3-butanediol, diethylene glycol monoethyl ether or 2,2-dimethyl-4-hydroxymethyl-1,3-dioxolane.

In one aspect, the invention provides a system for treating a capsaicin-responsive condition and having (1) an administered composition as described herein (2) an applicator device for applying the formulation to skin or a mucosal surface. In one embodiment, the applicator device is pre-filled with the composition. In one embodiment, the administered composition is contained in a container separate from the device.

9.3 Instillation

In one embodiment, the administered composition is administered by instillation. As used in this context, instillation means introducing the composition into a part of the body other than the skin, by a method other than injection. Examples of instillation are introduction into the bladder via catheter, introduction into the nasal cavity by spray, instillation into the urethra; and instillation into surgical wounds (e.g., to treat or prevent pain).

9.4 Administration by Injection

In some embodiments of the invention, formulations described herein are administered by injection. For example, injection methods may be used to deliver TRPV1 agonist to specific nerve trunks, tissues, or other sites in a subject. Advantageously, the administered compositions of the invention deliver a large quantity of a TRPV1 agonist in a small dose volume; small dose volumes entail reduced pain and tissue injury, and convenience for health care providers. Further, in view of the substantial depot effect seen in skin for some administered compositions of the invention, it is expected that the compositions, when injected, will depot in the area of injection, resulting in a low level of systemic exposure while providing a high local concentration of a TRPV1 agonist. Injection of TRPV1 agonists into nerve trunks can be used to block the incoming afferent pain signals from distal nociceptive nerve fibers, thereby providing benefit for patients with neuropathic pain syndromes (see, Pertovaara, 1988, "Collateral sprouting of nociceptive C-fibers after cut or capsaicin treatment of the sciatic nerve in adult rats" *Neurosci Lett.* 90:248-53). In other example, injection of TRPV1 agonist into prostate tissue can be used to control prostate cancer by selectively killing cancers cells of prostatic origin (see, e.g., Morre et al., 1997, "NADH oxidase activity from sera altered by capsaicin is widely distributed among cancer patients" *Arch Biochem Biophys.* 342:224-30; Szallasi et al., 2001, "Vanilloid receptor ligands: hopes and realities for the future" *Drugs Aging.* 18:561-73; Surh, 2002, "Anti-tumor promoting potential of selected spice ingredients with antioxidative and anti-inflammatory activities: a short review" *Food Chem Toxicol.* 40:1091-7; Van der Aa et al., 2003, "Interstitial cells in the human prostate: a new therapeutic target? *Prostate* 56:250-5).

9.5 Administration as a Microemulsion

In one embodiment, the administered composition is applied or instilled in the form of a microemulsion. In one embodiment, the microemulsion is instilled (introduced into) the bladder.

9.6 Other Administration Forms

It will be apparent to those of ordinary skill in the art that other methods of administration are known. All suitable methods are contemplated and encompassed by the invention. Other administration forms include administration using fluid-filled microspheres (see, e.g., U.S. Pat. Nos. 5,716,643; 6,264,988), liposomes, other hollow vesicles, cyclodextrins, micellular, or bioerodible gels.

10. Removal of Residual TRPV1 Agonist

In one aspect, the invention provides method of contacting a surface (e.g., skin) with a TRPV1 agonist to reduce nerve fiber functionality and/or treat capsaicin-responsive condition followed by the subsequent step of removing any residual agonist from the surface. In an embodiment, the residual agonist is removed by rinsing. In a different embodiment, the residual agonist removed by applying a cleaning composition in which the agonist is soluble and removing the cleaning composition. For illustration and not limitation, a suitable compound may be a polyethylene glycol (PEG)-based composition, such as aqueous gel containing 60 to about 99 percent w/w polyethylene glycol. In an embodiment, the cleaning agent is consists of PEG-300 (89.08%), polyacrylate thickening agent such as Carbopol 1382™ (1.0%), butylated hydroxyanisole (0.02%), disodium edetate (0.1%), balance water; gel is at a pH of about 6.5. See, e.g., PCT publication WO04021990A2 "Compositions and kits for the removal of irritating compounds from bodily surfaces."

If desired, the amount of agonist remaining as a residue on a skin surface can be determined using any of a variety of assays. For example, the residue can be removed from the skin by rinsing with a solvent in which the TRPV1 agonist is soluble, or wiping the application site with a swab, and the TRPV1 agonist weight, concentration or bioactivity in the solvent or swab can be determined. Suitable procedures for this determination will be apparent to those skilled in the art and with reference to the scientific literature. See, for example, Wang et al., 2001, *Int J Pharm* 14:89-104. In most assays, collection of samples of the residual amounts of drug on skin surface is conducted. One way of sampling is by wiping the application site using a surgical grade gauze sponge lightly soaked with a solvent suitable for that particular drug substance. The wiping is performed such that each surface of sponge is exposed only once during single longitudinal stroke. The gauze sponge is then placed on a sintered glass funnel and washed with an adequate known amount of same solvent (the same known quantity is used to soak the gauze initially). The resulting wash is analyzed by a method (chromatography, UV spectroscopy or mass spectrum analysis) suitable for quantitative determination of drug substance in question. See, e.g., M. J. Shifflet and M. Shapiro *Development of Analytical Methods to Accurately and Precisely Determine Residual Active Pharmaceutical Ingredients and Cleaning Agents on Pharmaceutical Surfaces*, American Pharmaceutical Review; Summer 2002. An alternative method of sampling is described by Nanji A. et. al. 1987, *J Toxicol. Gin Toxicol.* 25:501-15 (describing use of a suction probe to collect samples which were subsequently loaded directly into a mass spectrometer by thermal desorption).

11. Kits and Devices

In an aspect, the present invention provides a kit including (1) an administered composition of the invention and materials for removing residual agonist from the application surface (e.g., skin surface). In an embodiment, the kit contains a PEG-based cleaning gel such as those described in PCT publication WO04021990A2.

Additionally, a kit of the invention may include an anesthetic, chemical-resistant disposal bags, applicators for applying the cleansing composition, towels or towelettes for removing the cleansing gel, gloves, eye protection, scissors, marking pens, and additional bodily surface-cleansing agents such as alcohol swabs. In one embodiment, the anesthetic is lidocaine.

In an aspect, the invention provides a kit including (1) an administered composition of the invention and (2) a material or device for delivering the composition. In an embodiment, the composition is contained in a container separate from the device. in one embodiment, the applicator device is a sponge, brush, or swab.

12. Exemplary Effects

Application of the TRPV1 agonists of the invention results in a variety of beneficial physiological and/or therapeutic effects, some of which examples are described below.

12.1 Reducing the Density of Functional Nociceptive Nerve Fibers

As noted, in one aspect the invention provides a method of reducing the density of functional nociceptive nerve fibers (i.e., a reduction in nerve fiber functionality, NFF) in a selected region of a subject by contacting the region with a composition that contains a TRPV1 agonist and a solvent system containing one or more penetration enhancers, i.e., an administered composition as described herein.

In some embodiments of the invention, contacting the area with the administered composition for a specified period of time results in a substantial reduction in density. A "substantial reduction" in density or number of functional nociceptive nerve fibers means a reduction of at least about 20%, at least about 25%, at least about 28%, at least about 30%, at least about 40%, at least about 50%, at least about 60%, at least about 75%, and sometimes at least about 80% compared to an untreated (control) region or subject. See Examples 2 and 3, infra. In some embodiments, the specified period of time not more than about 10, 15, 20, 30, or 45 minutes.

The density or number of functional nociceptive nerve fibers can be determined by a variety of methods. A particularly useful method is immunostaining for protein gene product 9.5 ("PGP 9.5") as described by Nolano et al., 1999, *J Neuroscience* 81:135-45. Also see Kennedy et al., 1996, "Quantitation of epidermal nerves in diabetic neuropathy" *Neurology* 47:1042-48. A reduction in PGP 9.5 staining is indicative of a reduction in NFF. Other methods for measuring functional or structural inactivation of nerve fibers include substance P immunostaining, calcitonin-related-gene-product immunostaining, S100 immunostaining, immunostaining for neurofilament proteins and immunostaining for TRPV1 receptors, e.g., using anti-TRPV1 receptor antibodies. Analysis of immunostaining is usually conducted between 2 and 7 days following administration of the TRPV1 agonist. In various embodiments nerve fiber density is measured 2, 3, 4, 5, 6 or 7 days after administration of the composition. In one embodiment, the density of functional nociceptive nerve fibers is measured 7 days after administration of the TRPV1 agonist. Alternatively, methods other than immunostaining can be used to assess the density of cutaneous nociceptors.

Examples 2 and 3 illustrate assays for NFF following topical application of capsaicin or resiniferatoxin. Exposure to a TRPV1 agonist may lead to either a frank reduction in the number of countable nerve fibers in the epidermis and dermis or to changes in the appearance of those nerve fibers. When PGP 9.5 immunoassays are used to monitor NFF, only PGP 9.5-positive nerve fibers with normal morphological appearance are counted. Areas of skin affected by peripheral neuropathies are characterized by atypical swelling, varicosities or segmentation of small diameter nerve fibers (nociceptors) (see, e.g., McArthur et al., 1998, "Epidermal nerve fiber density: normative reference range and diagnostic efficiency" *Arch Neurol.* 55:1513-20; Herrmann et al., 2004, "Epidermal nerve fiber density, axonal swellings and QST as predictors of HIV distal sensory neuropathy" *Muscle Nerve.* 29:420-7) and similar changes in nociceptor morphology are believed to occur following exposure of skin to topical capsaicin. In counting the number of nerve fibers per mm of skin, only nerve fibers with normal morphological appearance are counted. Further, if a substantial number of nerve fibers in any skin section are swollen or have varicosities, such that it is not possible to count fibers with normal appearance, and the section is assigned a value of 0 nerve fibers.

12.2 Sustained Reduction of Neuropathic Pain

In one aspect the invention provides a method, application of the administered composition to a subject with neuropathic pain results in a sustained or persistent diminution of symptoms (e.g., pain). In some cases, one or two administrations are sufficient to provide persistent relief (i.e., relief for at least about four weeks, preferably at least about 8 weeks).

12.3 Reduction of Skin Sensitivity Following Administration of TRPV1 Agonists (QST Assay)

Nociceptive nerve fibers normally respond to warm and cold thermal stimuli. Hence, changes in thermal thresholds are indicative of reduced nociceptor function and can be used to measure NFF. A "substantial reduction" in NFF can be detected as a change in thermal threshold. Quantitative sensory testing (QST) can be used to detect changes in thermal thresholds, due either to diseases or exposure to TRPV1 agonists (Bjerring et al., 1989, "Use of a new argon laser technique to evaluate changes in sensory and pain thresholds in human skin following topical capsaicin treatment" *Skin Pharmacol.* 2:162-67). Methods of QST are well established in the scientific literature and known widely to those skilled in the art (Siao et al., 2003, "Quantitative sensory testing" *Phys Med Rehabil Clin N Am.* 14:261-86.) For example, a decreased ability to detect the cold sensation produced by a metal roller (Therrell device, Somedic Production A13, Sollentuna, Sweden) pre-cooled to 12° C. can be measured. In various embodiments, the change in thermal threshold is at least about 10%, at least about 20%, at least about 25%, at least about 28%, at least about 30%, at least about 40%, and sometimes at least about 50% compared to an untreated (control) region or subject.

12.4 Administration of TRPV1 Agonists with Reduced Discomfort

It is generally known that administration of capsaicin produces an intense burning pain. Application of even relatively low concentrations of capsaicin results in pain that is intolerable to many patients. For this reason, capsaicin may be administered following, or concurrently with, administration of anesthetic.

Surprisingly, it has been discovered that rapid administration of TRPV1 agonists using the methods and compositions of the invention results in less pain or discomfort than administration of conventional capsaicin formulations containing much lower concentrations of capsaicin. Example 4 shows that, surprisingly, 10% w/v capsaicin liquid formulation produced statistically significant (p≤0.1) less pain response than Zostrix® cream when applied to rat vulva (Zostrix® cream is a commercially available 0.075% capsaicin formulation). Similarly, Example 5 suggests that topical application of a 10% capsaicin liquid formulation in diethylene glycol monoethyl ether produced less nocifensive behavior over a 90-minute observation period than did topical application of a commercially available over-the-counter low-concentration (0.1%) capsaicin cream.

It is contemplated that, using the methods of the present invention, moderate (>1%), and high (>3%) even a very high dose of capsaicin can be administered to a patient without the requirement for pretreatment with, or coadministration of, anesthetic. Moreover, when anesthesia is used before, during or after exposure to a TRPV1 agonist, less anesthetic or shorter exposure to anesthetic will be required to achieve the same effect on discomfort. Thus, in one aspect, the invention provides methods for administration of a TRPV1 agonist such as capsaicin, at a concentration of greater than 1% (w/v), greater than 2%, greater than 3%, greater than 4%, greater than 5%, or greater than 6%, without the need for anesthetic, using the compositions of the invention.

13. Therapeutic Uses of TRPV1 Agonist-Containing Compositions

This section describes use of the compositions of the invention. However, it will be understood that the examples in this section are provided for illustration and not limitation. As noted above, capsaicin application has numerous therapeutic benefits, each of which can be effectively treated using the methods of the invention. Conditions for which TRPV1 agonist treatment may be indicated include neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, low back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritis, itch, tinnitus, psoriasis, warts, cancers (especially skin cancers), headaches, and wrinkles. Generally, the TRPV1 agonist-containing compositions can be used to treat any condition for which topical administration of a TRPV1 agonist (e.g., capsaicin) is beneficial.

13.1 Neuropathic Pain

Neuropathic pain, such as that associated with diabetic neuropathy or postherpetic neuralgia, has proven particularly refractory to treatment. However, capsaicin has been demonstrated efficacious in treatment of neuropathic pain. For example, inactivation of cutaneous nociceptors in the epidermis and dermis induced by an 8% w/w capsaicin dermal patch has demonstrated clinical efficacy against postherpetic neuralgia, a prototypic neuropathic pain condition (see Backonja et al., "A Single One Hour Application of High-Concentration Capsaicin Patches Leads to Four Weeks of Pain Relief in Postherpetic Neuralgia Patients" American Academy of Neurology, 2003 (meeting abstract)). The compositions of the present invention are effective for treating such neuropathic pain.

The efficacy of specific compositions with respect to the ability to render cutaneous nociceptors persistently non-functional can be determined by immunohistochemical evaluation of the density of skin markers for cutaneous nociceptors, such as protein gene product 9.5 (PGP 9.5). Standard methods can be utilized to quantify changes in PGP 9.5 staining densities (see Nolano et al., 1999, *J Neuroscience* 81:135-45). Analysis can be made of punch biopsies taken 3 to 7 days following treatment with a formulation. Compositions of the present invention that produce loss of PGP 9.5 staining comparable or superior to the capsaicin dermal patch (see Backonja et al., 2003) are expected to produce similar or superior analgesic activities.

A single administration of a TRPV1 agonist-containing (e.g., capsaicin containing) composition of the invention can be used to provide significant and long lasting relief from chronic pain conditions, particularly neuropathic pain and inflammatory pain. As used in this context, significant pain relief means a reduction of at least 15%, and sometimes at least 50%, relative to the pain that the patient initially reported. Pain can be measured using routine techniques, such as application of the Likert pain scale (see Guyatt et al., 1987, "A comparison of Likert and visual analogue scales for measuring change in function" *J Chronic Dis.* 40:1129-33). As used in this context, long lasting pain relief means relief for at least two weeks, usually at least 1 month, and often relief for 3-6 months after administration. It is expected that application of a composition comprising 1-10% (w/v) capsaicin for 2 to 60 minutes will provide significant relief. Usually, application for 30 minutes or less, such as 15 minutes or less, or even 10 minutes or less will provide significant relief.

13.2 Inflammatory or Nociceptive Pain

The TRPV1 agonist are useful for amelioration of inflammatory or nociceptive pain, particularly that due to such conditions as osteoarthritis, rheumatoid arthritis, joint pain, surgery, trauma, bruises, abrasions, lower back pain, acute herpes zoster or cancers.

13.3 Cancers

TRPV1 agonist compositions of the invention are particularly valuable for treatment of various types of cancers, e.g., skin cancers. Capsaicin has been shown to prevent cancer cell growth and/or induce cancer cell apoptosis in vitro assays, using a variety of cancer cell lines (for review, see Y-J Surh, 2002, "More Than Spice: Capsaicin in Hot Chili Peppers Makes Tumor Cells Commit Suicide", *J Nat Cancer Inst*, 94:1263-65). According to the invention, the capsaicin or TRPV1 agonist compositions of the invention are delivered directly to cancerous tissues or cells, or to pre-cancerous cells (e.g., cells responsible for prostatic hyperplasia or uterine abnormalities). For treatment of skin cancers, for example, the composition can be applied by topical application or, alternatively, by injection or instillation. Because capsaicin enhances the percutaneous absorption of other compounds, the delivery of a combination of capsaicin with anti-cancer compounds (e.g., 5-fluouracil) would be expected to be efficacious.

13.4 Oral Mucositis

TRPV1 agonist compositions of the invention are also used for treatment of oral mucositis. Oral mucositis is a significant problem in patients receiving chemotherapy or radiation therapy. Estimates of oral mucositis in cancer therapy range from 40% receiving standard chemotherapy to 76% in bone marrow transplant patients. The efficacy of capsaicin for treating oral mucositis has been described (Berger et al., 1995, *J Pain Symptom Manage* 10:243-8). However, the pain relief provided by previous formulations was not complete for most patients and was of limited duration. This may have been due to the nature of previous formulations, either their ability to induce pain or inability to precisely deliver high concentrations of capsaicin to the site of oral mucositis.

Administration of the compositions of the invention to lesions of oral mucosa would provide rapid and convenient delivery of capsaicin, or other TRPV1 agonists. Application of compositions could be achieved by means of a swab, spray, roller, syringe or other device.

13.5 Bladder Disorders

Instillation of capsaicin-containing solutions into the bladder has been used to treat a variety of bladder disorders, including neurogenic bladder, interstitial cystitis, detrusor hyperreflexia and overactive bladder (for review, see Fowler et al., 2002, "Voiding and the Sacral Reflex Arc: Lessons from Capsaicin Instillation," *Scand J Urol Nephrol Supple* 210:46-50.). Although generally efficacious, these procedures require at least 20 minutes of drug solution exposure, and produce significant pain and discomfort for patients. See Chancellor et al., 1999, *J Urol* 162:3-11. The compositions of the present invention can be used to treat such bladder disorders. In one embodiment, the composition is administered in the form of a microemulsion such as is described infra in Section 13 instilled into the bladder. In another embodiment, the agonist-containing composition described herein is miscible with water due to the co-solvency of the penetration enhancer. An amphiphilic solvent system, such as capsaicin dissolved in diethyleneglycol monoethyl ether, may impart sufficient solubility of capsaicin in water to allow direct instillation of the resulting monophasic mixture.

13.6 Prostatic Hyperplasia

Prostatic hyperplasia is a condition affliction many millions of males around the world. Notably, hyperpoliferative prostate cells share many features of cancer cells (which, as described supra, apoptose in response to capsaicin). See Tayeb et al., 2003, *Br J Cancer* 88:928-32. This condition can be treated by administration of the compositions of the invention. In one embodiment, the composition is administered in the form of a microemulsion such as is described infra in Section 13 instilled into the urethra, would be of particular value to treat (and perhaps reverse) prostatic hyperplasia. In addition to treatment of hyperplasia, instillation of a composition of the invention should also reduce the discomfort of urination symptom characteristic of prostatic hyperplasia. Injecting capsaicin directly into the prostate would affect the pacemaker and hyperplastic cells that express TRPV1. See Exintaris et al., 2002, *J. Urol.* 168: 315-22.

13.7 Psoriasis, Dermatitis, Pruritis and Itch

The efficacy of capsaicin against psoriasis, dermatitis, pruritis and itch has been documented in well-controlled clinical trials (e.g., see Bernstein et al., 1986, "Effects of Topically Applied Capsaicin on Moderate and Severe Psoriasis Vulgari," *J Am Acad Dermatol* 15:504-507; Ellis et al., 1993, "A Double-Blind Evaluation of Topical Capsaicin in Pruritic Psoriasis," *J Am Acad Dermatol* 29:438-42). Such treatment requires application of low concentration creams many times per day for many weeks. In accordance with the present invention, the compositions described herein are applied topically to sites of psoriasis, dermatitis, pruritis or itch. It is expected that this treatment will provide superior and longer lasting relief than presently available methods.

13.8 Warts

The common wart, or *Verruca vulgaris*, occurs in between 5 percent and 10 percent of children and in a smaller percentage of adults. The standard treatment is freezing with drops of liquid nitrogen, or cryotherapy. This procedure can be effective, but it can require months of repeated, painful applications that are scary to many children and can sometimes lead to blisters and infections. Also, cryotherapy has been reported to be of limited efficacy. The capsaicin-containing compositions of this invention find use in the treatment of common warts. It is expected that this treatment will provide superior and longer lasting relief than presently available methods.

13.9 Migraine and Headache

Migraine (including migraine with aura) and headache (e.g., cluster headache) are characterized by disabling pain and hyperactivation of the trigeminal nervous system. Evidence exists that topical application of TRPV1 agonists onto nasal mucosa can prevent or reverse headache. See, e.g., Saper et al., 2002, *Arch Neurol* 59:990-4; and Vass et al., 2001, *Neuroscience* 103:189-201. As the trigeminal nervous system innervates that skin of the face and head, as well as the mucosa of the nasal cavity. According to the invention, topical application of the compositions of the invention to trigeminal nervous system (e.g., application to the forehead or other parts of the face or head or into nasal passages) is used to prevent or reduce the symptoms of headache.

13.10 Wrinkles

Many wrinkles are caused by tonic activation of muscles underlying the skin. A reflex arch involving sensory nervous system hyperactivity is likely to be involved. Application of compositions of the present invention is used to reduce the depth or extent of wrinkles, or prevent the formation of wrinkles.

13.11 Tinnitus

There are many similarities between the symptoms and signs of severe tinnitus and chronic pain, e.g., some individuals with severe tinnitus perceive sounds to be unpleasant or painful and some of the same drugs are used to treat both conditions (Moller, 2000, "Similarities between severe tinnitus and chronic pain" *J Am Acad Audiol.* 11:115-24). Little is known about the anatomic location of the changes that causes tinnitus, but it may be the inferior colliculus, as well as other structures. TRPV1 are found in hair cells and supporting cells of the organ of Corti and the spiral ganglion cells of the cochlea. Animal studies indicate that the main action of capsaicin is on outer hair cells and suggest that TRPV1 in the cochlea play a role in cochlear homeostasis (Zheng et al., 2003, "Vanilloid receptors in hearing: altered cochlear sensitivity by vanilloids and expression of TRPV1 in the organ of cord" *J Neurophysiol.* 90:444-55). Moreover, activation of TRPV1 by endogenous ligands may contribute to hypersensitivity of the eighth nerve to hair cell inputs in a variety of pathologic conditions, such as tinnitus, Meniere's disease and migraine (Balaban et al., 2003, "Type 1 vanilloid receptor expression by mammalian inner ear ganglion cells" *Hear Res.* 175:165-70). It is expected that compositions of the present invention may be effective for treatment of tinnitus.

14. Screening Methods

In one aspect, the invention provides a method for identifying a composition as useful for therapeutic delivery of a TRPV1 agonist to a subject by determining the depot effect for a solution consisting of the composition and the TRPV1 agonist or a different TRPV1 agonist, where a depot effect less than 0.25 indicates composition is useful for therapeutic delivery of a TRPV1 agonist. In alternative embodiments, a depot effect less than 02, 0.1, 0.05, 0.01, 0.005 or 0.001 indicates composition is useful for therapeutic delivery of a TRPV1 agonist. In one embodiment, there is a further step of determining the amount of agonist delivered to skin epidermis and dermis after a specified time when the composition is applied to the skin surface.

In a related aspect, the invention provides a method for ranking two or more compositions according to their utility for therapeutic delivery of a TRPV1 agonist to a subject by determining for each composition the depot effect for a solution consisting of the composition and the TRPV1 agonist or a different TRPV1 agonist, comparing the values obtained for each composition, and ranking them compositions according to the values, where a composition with a lower value is ranked more suitable for therapeutic delivery of the TRPV1 agonist. In one embodiment, there is a further step of determining, for each composition, the amount of agonist delivered to skin epidermis and dermis after a specified time when the composition is applied to the skin surface, where a composition with a higher value is ranked more suitable for therapeutic delivery of the TRPV1 agonist.

In various embodiments of these methods: (i) the composition contains one or more penetration enhancers; (ii) the composition is a composition of the present invention; (iii) the TRPV1 agonist is capsaicin; (iv) the depot effect is determined in vitro; (v) the depot effect is determined using mouse skin; or (v) the depot effect is determined using mouse skin assay of the present invention.

15. Preparation and Administration of Microemulsion

Compositions of the invention can be administered in the form of a microemulsion. Methods for making microemulsions are generally known in the art. See, e.g., Prince, 1970 "Microemulsions" *J. Soc. Cosmet. Chem.* 21:193-204; Prince L. M. in MICROEMULSIONS—THEORY AND PRACTICE, Academic, New York 1977; Belloq A. M. et al; *Adv Colloid Interface Sci* 20: 167, 1984 and Bourrel M., Schechter R. S. in MICROEMULSIONS AND RELATED SYSTEMS, Dekker, New York, 1988.

In one version, a microemulsion comprising three components is prepared. The three components are an internal phase, an external phase, and one or more emulsifiers.

The Internal Phase

The content of the internal phase depends on the nature of the TRPV1-agonist-containing composition used to make the microemulsion. When the composition is not miscible in water, the composition serves as the internal phase (although it can be optionally combined with an oil in which the composition is miscible). When the composition (i.e., comprising a TRPV1-agonist and a solvent system, e.g., 5% (w/v) capsaicin in diethylene glycol monoethyl ether) is either amphiphilic or hydrophilic, the composition is mixed with an oil in which it is miscible. Examples of such oils include, for illustration and not limitation, mineral oil, mink oil, linseed oil, tung oil, pine oil, and vegetable oils. The internal phase is dispersed as microdroplets (e.g., having a diameter of about 10 to about 200 nm, usually about 10 to about 60 nm).

The External Phase

The external phase is an aqueous liquid, such as water, saline, buffer, or the like. The external phase is the medium in which the microdroplets are dispersed.

The Emulsifier(s)

Examples of suitable emulsifiers (for illustration and not limitation) include mineral oil, Pluronic (BASF), polyethoxylated fatty acids, PEG diester fatty acids, PEG fatty acid mixtures of mono- and di-esters, polyglycerized fatty acids, mono- and diglycerides, sterols and sterol derivatives, sugar esters, polyoxyethylene-polyoxypropylene block copolymers, sorbitan fatty acid esters, lower alcohol fatty acid esters, ionic surfactants, and non-ionic surfactants, and combinations thereof.

Optional Components

In addition, the microemulsion may include other components such as stability enhancing components (e.g., antimicrobials, antioxidants, and the like) pH adjusting agents and the like, stabilizing agents, and the like). However, usually these components are present in small amounts (e.g., less than about 5% (w/v), most often less than about 1%).

Preparation of Microemulsion

A microemulsion may be prepared by adding at least one emulsifier (e.g. polyglyceryl-6 dioleate) to the internal phase (e.g., 5% capsaicin solution in diethylene glycol monoethyl ether mixed with oil). The mixture is then added to an external phase (e.g., water). The resulting mixture is vigorously stirred, sonicated or otherwise agitated with or without the application of heat until stable microdroplets are formed and a homogeneous distribution results. The pH can be adjusted to improve the stability and/or physiological tolerance of the microemulsion.

Concentrated formulations of a TRPV1 agonist can be prepared containing co-solvents, surfactants, emulsifiers, and thickeners in concentrations higher than the expected final administered composition. (See Example 6.) These formulations are "preconcentrates," not intended for direct administration but require further dilution in a suitable vehicle to obtain the desired administration concentration.

Use of Microemulsion

The microemulsion is contacted with a tissue to which the TRPV1 agonist is intended to be delivered. Without intending to be bound by a particular mechanism, it is believed that the microdroplets will fuse rapidly with the target tissue (i.e., tissue with which the microemulsion is in contact) and deliver the TRPV1 agonist and any other therapeutically active agents to the tissue.

Examples of treatments for which microemulsion administration is useful include, without limitation, (1) treatment of peripheral neuropathy, arthritis, psoriasis and frostbite (administration via bath); (2) treatment of neurogenic bladder, interstitial cystitis or similar conditions (instillation into the bladder); (3) treatment of prostate cancer or prostatic hyperplasia (instillation into the urethra); and (4) instillation into surgical wounds to treat or prevent pain.

The method of contacting of the tissue and microemulsion will vary depending on the nature of the tissue and condition to be treated. One example of a method for administration is via a water-bath type device (i.e., a container of the microemulsion in which a target tissue, such as a hand or foot, can be immersed).

For example, the present invention provides methods and devices for administering a TRPV1 agonist composition (either a microemulsion or another other TRPV1 agonist-containing composition, such as those described hereinabove) using a bath type device. In one version, the bath device includes a basin for containing the TRPV1 agonist microemulsion and for receiving an affected area of tissue. For example, a hand, foot, elbow, or any other affected area may be immersed into the bath for treatment. This type of device has certain advantages.

First, a bath type device provides a convenient way to help ensure that the entirety of the affected area is treated, because entire body parts may easily be immersed into the bath for treatment. A therapeutic bath is especially suitable for patients suffering from certain types of neuropathy, such as, diabetic peripheral neuropathy, which typically affects and produces pain within the lower extremities first, i.e., the feet. A therapeutic bath can also be used for the treatment of musculoskeletal pain. Patients suffering from diabetic peripheral neuropathy can immerse their feet into the bath device described herein for treatment using the methods described herein. Similarly, neuropathic pain within the upper extremities typically starts within the fingertips, before moving up the hands and arms. Therefore, a therapeutic bath is also especially useful for the treatment of the fingers and hands.

Second, use of a bath type device is helpful in controlling and enhancing drug delivery. This is because the environmental conditions affecting drug delivery can be closely regulated and modified. For example, temperature, hydration, salt content, and drug concentration have all been shown to have an affect on absorption of a drug through the skin. Therefore, regulation of these properties can help control or enhance drug delivery.

In its simplest form, the bath device provides a container to house a treatment fluid. The container is of sufficient size such that an affected area may be immersed therein. The device may, for example, take the form of a bath for the feet. However, it should be understood that the bath can be of any number of shapes and sizes, and therefore be suitable for immersion of any number of affected body parts. In one embodiment, the bath comprises a basin for containing the TRPV1 agonist microemulsion and receiving a body part therein. The basin has a bottom surface and a wall structure extending upwardly therefrom.

When the bath is a foot-bath type of device, the basin has a length and width sufficient to accommodate the feet of an average sized adult user. Similarly, the basin size can be selected so as to provide enough space to permit the user to easily insert and remove the feet therefrom. In addition, the bath may include certain anatomically designed features. For example the bath device can include separate foot rests, optional supports for the arches, or other contoured shapes designed for the feet. The bath can be made of any appropriate material.

In some embodiments, the bath includes heating or cooling elements designed to regulate the temperature of the basin or the microemulsion contained therein. Increased temperatures may help facilitate penetration of the TRPV1 agonist through the skin. Conversely, decreased temperatures may help improve tolerability to any discomfort resulting from exposure to certain TRPV1 agonists. The heating or cooling elements can be electrically controlled or can be battery operated. In some embodiments, the heating element provides the capability of focusing heat on a specific region of the foot of the user, for example, by using infrared rays. However, any type of suitable heating element may be used. The bath may also include an ultrasound or a sonication element to emit waves through the TRPV1 agonist microemulsion. Without wishing to be bound by any particular theory, it is thought that the use of such waves helps facilitate penetration of the TRPV1 agonist through the skin.

The bath may also have a lid or seal to entrap fumes and prevent accidental spillage. The lid may be entirely removable, or it may not be. For example, the lid can be configured to snap fit over the basin surface, or may be attached to the basin using any other suitable attachment device (e.g., hinges). In some embodiments, the lid is designed to cover the entire basin surface and form a seal around the affected area while the affected area is receiving treatment.

A control panel may be used to control the heating, cooling, and sonication elements. The control panel may be powered by any suitable power supply, for example; a power cord that plugs into a 110 V AC outlet, or even a battery. Having the bath powered by a battery helps facilitate the portability of the device. In addition, the control panel may have a timer device to keep track of treatment time and to notify the user when the treatment is complete. Any number of additional modifications or controls may be added to the control panel as desired.

As noted above, one aspect of the invention provides a method of administering a TRPV1 agonist microemulsion using a bath device. In operation, the TRPV1 agonist microemulsion is added to the basin of the device. Then the affected body part is immersed within the microemulsion for a predetermined period of treatment time. Treatment times will vary depending upon the chosen agonist. In one embodiment, capsaicin is the VR1 receptor antagonist. In one embodiment, the capsaicin can be added to the basin as an microemulsion (e.g., as described above), or the capsaicin microemulsion may be formed in the bath itself (e.g., by providing the capsaicin in a suitable solvent system, adding an emulsifying agent, and then mixing with water).

In another aspect, the invention provides methods and devices for administering the TRPV1 agonist in an article of clothing or garment. The garments may for example, be gloves, socks, or finger or toe booties, designed to be worn on the extremities of those affected by neuropathy. It is desirable that the garments are made of a close-fitting and stretchable material that allows the microemulsion to be coated thereon or impregnated therein. The material may be made of any number of natural or synthetic fibers. The thickness and the elasticity of the garments will vary depending on the type of microemulsion used and the type of garment desired. The garments may be of any length, and may be disposable or may be reusable. In some embodiments the garments are multi-layered. The layers can include an outer layer that is moisture and vapor impermeable.

16. Examples

Example 1

Determination of TRPV1 Agonist Content Using the Mouse Skin Absorption Assay and Demonstration of Rapid and Efficient Delivery of TRPV1 Agonists to Mammalian Skin This example shows delivery of TRPV1 agonists using various compositions, and described the "mouse skin absorption assay." The mouse skin absorption assay is an in vitro assay for measuring the delivery and retention of a TRPV1 agonist. The assay is generally as described by Kemppainen and Reifeinrath, 1990, in METHODS FOR SKIN ABSORPTION, CRC Publication (hereinafter, "Kemppainen"), with the following modifications: Tissue that was not used on the day of animal sacrifice was stored at less than −70° C., rather than at less than −60° C., until the day of the experiment; and $^3H_2O$ with a specific activity of ~0.5 µCi/mL (rather than ~0.3 µCi/mL) was used, and the receptor solution was collected and analyzed at 30 minutes, rather than 20 minutes as described in Kemppainen.

Skin Preparation

Mouse trunk skin (Nu/Nu) without obvious signs of skin disease, obtained within 2 hours of death, was used in this study. When obtained it was cleared of subcutaneous tissue, sealed in a water-impermeable plastic bag, and, if not used on the day of arrival, stored at <−70° C. until the day of the experiment. Prior to use it was thawed by placing the bag in ~37° C. water, and then rinsed in tap water to remove any adherent blood or other material from the surface.

Skin from a single donor was first cleared of all subcutaneous tissue and approximately 50% of the dermis by manual scalpel technique, and then cut into multiple smaller sections large enough to fit onto 0.8 cm² Franz diffusion cells (Crown Glass Co., Somerville, N.J.). The dermal chamber (receptor side) was filled to capacity with a receptor solution of phosphate-buffered isotonic saline (PBS), pH 7.4±0.1, and the epidermal chamber (donor side) was left open to the ambient laboratory environment. The cells were then placed in a diffusion apparatus in which the dermal receptor solution is stirred magnetically at ~600 RPM and which is maintained to achieve a skin surface temperature of 33.0±1.0° C. Skin surface temperature from representative chambers were measured and recorded.

To assure the integrity of each skin section, its permeability to tritiated water was determined before application of the test products (Franz et al., 1990, "The use of water permeability as a means of validation for skin integrity in in vitro percutaneous absorption studies" Abst. *J. Invest. Dermatol.*, 94:525). Following a brief (0.5 to 1 hour) equilibrium period, $^3H_2O$ (NEN, Boston, Mass., sp. Act. ~0.5 µCi/mL) was layered across the top of the skin by dropper so that the entire exposed surface was covered (approximately 100-150 µL). After 5 minutes the $^3H_2O$ aqueous layer was removed. At 30 minutes the receptor solution was collected and analyzed for radioactive content by liquid scintillation counting, and skin integrity confirmed based on quantification of penetration. Typical skin specimens in which absorption of $^3H_2O$ was less than 1.75 µL-equ were considered acceptable.

Prior to administration of the topical test formulations to the skin sections, the receptor solution was replaced with fresh 1:10 PBS solution prior to dosing. Prior to dosing the dosing chamber half-cell was removed to provide full access to the skin surface. All formulations were then applied to the skin sections using a calibrated positive displacement pipette, with a target dosing volume of 10 µL/0.8 cm². The formulation was spread throughout the surface of the skin using the Teflon tip of the pipette. One to five minutes after application the donor half-cell of the Franz chamber was replaced to re-seal and to secure the skin in the chamber.

At a pre-selected time after dosing (15 minutes) the receptor solution was removed in its entirety, and a 4 mL volume freeze dried (Savant SpeedVac) and saved for subsequent analysis.

Each skin section was surface washed with 0.5 mL of methanol twice to remove any residual TRPV1 agonist. Skin sections were removed from the chambered, scored along the circumference edge of the 0 ring indentation with a scalpel, and the epidermis was gently teased from the dermis with fine-tipped forceps. The skin sections were then separated into epidermis and dermis. Each separate epidermis and dermis was mixed with 1 mL methanol and allowed to extract for approximately 24 hours at room temperature on a horizontal shaker.

Quantification of capsaicin was by High Performance Liquid Chromatography with Mass Spectrometry detection (HPLC-MS). Briefly, HPLC-MS was conducted on a Hewlett-Packard 1100 Series HPLC system with a 1100 Series API-ES LC/MSD in positive ion mode. A solvent system consisting of 70% Acetonitrile+0.1% TEA, 30% water+ 0.1% Formic acid was run through a C18 Luna column (4.6×100 mm, 3 µm, Phenominex Inc.) at a flow rate of 0.5 mL/min (6.5 minute run duration). Twenty microliters of sample were injected. Peak areas were quantified to concentration using an external standard curve prepared using pure synthetic capsaicin standard and quantified by external standard methods.

The results are summarized in Tables 4 and 5.

Example 2

Reduction of Nerve Fiber Functionality in Nude Mouse Skin

This example shows a reduction of nerve fiber functionality (NFF) as demonstrated by PGP 9.5 immunostaining following application of capsaicin to mouse skin. The experiments were performed on 8-12 week old nude mice (Nu/Nu) (Charles River). The mice were acclimated and arbitrarily divided into either 2 dose groups (for Experiment 1) of 12 mice per group (6 male and 6 female) or 4 dose groups (for Experiment 2) of 20 mice per group (10 male and 10 female).

In Experiment 1, On Day 0, 15 µL of 10% (w/v) capsaicin in 100% diethylene glycol monoethyl ether (DGME) and 0.1% (w/v) ethyl cellulose (i.e., Formulation No. 23 containing 0.1% ethyl cellulose) was applied to a 1 cm×1 cm area on the back of anesthetized mice of one group, while the control group received DOME dispersed in an adhesive matrix. In Experiment 2, On Day 0, 15 µL of either 15% (w/v) capsaicin in 15% oleic acid, 10% isopropyl myristate, 10% cetyl alcohol, 55% DGME and 10% methanol and 0.1% ethyl cellulose (i.e. Formulation No. 42 containing 0.1% ethyl cellulose) or 15% capsaicin (w/v) in 20% oleyl alcohol and 80% propylene glycol plus containing 0.1% ethyl cellulose (i.e., Formulation No 28 containing 0.1% ethyl cellulose) or 15% capsaicin (w/v) in 90% 1 menthone and 10% methanol plus 0.1% ethyl cellulose (i.e., Formulation No. 27 containing 0.1% ethyl cellulose) was applied to a 1 cm×1 cm area on the back of anesthetized mice of three groups, while the control group did not receive any treatment. In both experiments, mice were maintained under general anesthesia during the 30-minute treatment period and until the test articles were removed. After removal of the test article, the skin area was cleaned with a cleansing gel (89.08% PEG 300, 1.0% Carbopol 1382™, 0.02% butylated hydroxyanisole, 0.01% disodium edentate, pH 6.5). On Day 7, the mice were sacrificed and the tissue from the application site was collected and split into two equivalent sections. One section of skin was placed on a piece of cardboard, fixed in 10% neutral buffered formalin and processed to a hematoxylin-eosin stained slide for evaluation of inflammation and any other abnormalities. Another skin section was prepared as a frozen block for immunohistochemistry with an antibody PGP 9.5. This tissue was stained with an antibody for PGP 9.5 which identifies the skin sensory nerve fibers. Processed tissues were evaluated by a board certified veterinary pathologist for (1) any and all lesions, with particular attention to inflammation and any microvascular changes, and (2) the presence, absence and any abnormalities in the architecture of the skin sensory nerve fibers. For each specimen, nerve fiber density was determined by counting the number of normal-appearing nerve fibers observed in at least four microscopical fields (each circular microscopical field had a radius of 90 µm) and then averaged. If the morphology of nerve fibers in a field was changed, i.e., there was swelling, blebbing or varicosities, and the majority of nerve fibers appeared to exhibit morphological changes, then that field was assigned a value of no normal nerve fibers. The reported data are the decrease in average of number of nerve fibers per microscopical field per animal, compared to the respective controls. Average nerve fiber densities between groups were compared in order to determine what if any effects the various treatments had on nerve fiber density.

The results of the study in this example show that in Experiment 1, a 10% capsaicin (w/v) in DGME and 0.1% ethyl cellulose (Form. No. 23) caused approximately a 49% decrease in nerve fiber density, compared to DGME dispersed in an adhesive matrix. This decrease is statistically significant ($p \le 0.01$). In Experiment 2, 15% capsaicin (w/v) in 15% oleic acid, 10% isopropyl myristate, 10% cetyl alcohol, 55% DGME, 10% methanol, and 0.1% ethyl cellulose (Form. No. 42) caused approximately a 39% decrease in nerve fiber density, 15% capsaicin (w/v) in 20% oleyl alcohol, 80% propylene glycol and 0.1% ethyl cellulose (Form. No. 28) caused approximately 70% decrease in nerve fiber density, while 15% capsaicin (w/v) in 90% 1 menthone, 10% methanol, and 0.1% ethyl cellulose (Form. No. 27) caused approximately 75% decrease in nerve fiber density, compared to the untreated control. All decreases in nerve fiber density observed in this experiment were statistically significant ($p \le 0.01$).

Example 3

Reduction of Nerve Fiber Functionality in Rat Vulva

This example shows the effect of local application of TRPV1 agonist formulations to rat vulva.

Sixty female retired breeder Sprague-Dawley rats were divided into 6 groups. On day 0, rats were anesthetized with isoflurane anesthetic gas and then LMX5® anesthetic cream was applied to the entire vulvar area of each rat at least 30 minutes. The test formulations were applied using a micropipette to dispense 33 µL of each formulation. The formulations applied were diethylene glycol monoethyl ether (DGME) alone; 0.01% capsaicin (w/v) in DGME; 0.1% capsaicin (w/v) in DGME; 1% resiniferatoxin (w/v) in DGME; 3% capsaicin (w/v) in 90% (v/v) DGME and 10% (v/v) DMSO, a 10% capsaicin (w/v) in DGME. The formulations were left on for 20 minutes with the exception of 10% capsaicin (w/v) in DGME which was left on for 5 minutes. The remaining formulation was removed using a cleansing gel (89.08% PEG 300, 1.0% Carbopol 1382™, 0.02% butylated hydroxyanisole, 0.01% disodium edentate, pH 6.5). The gel was left on for approximately 3-5 minutes and then removed using Kim wipes and genital swabs. On Day 7, the rats were sacrificed and a 1 mm punch biopsy of the vulva was collected in ice cold Phosphate Buffered Saline for preparation as a frozen block for immunohistochemistry. Frozen sections made from this tissue were stained with anti-PGP 9.5 antibody, which stains the terminal sensory nerve fibers. The tissues were evaluated by a board certified veterinary pathologist for (1) any and all lesions, with particular attention to inflammation and any microvascular changes, and (2) the presence, absence and any abnormalities in the architecture of the terminal nerve sensory nerve fibers. For each specimen, nerve fiber functionality was determined by counting the number of nerve fibers observed in at least four microscopical fields (each circular microscopical field has a radius of 90 µm) and then averaged. If the morphology of nerve fibers in a field was changed, i.e., there was swelling, blebbing or varicosities, and the majority of nerve fibers appeared to exhibit morphological changes, then that field was assigned a value of no normal nerve fibers. The reported data are the average of number of nerve fibers per microscopical field per animal. The findings between groups were compared in order to determine what if any effects the various treatments have on nerve fibers.

Figure 2:
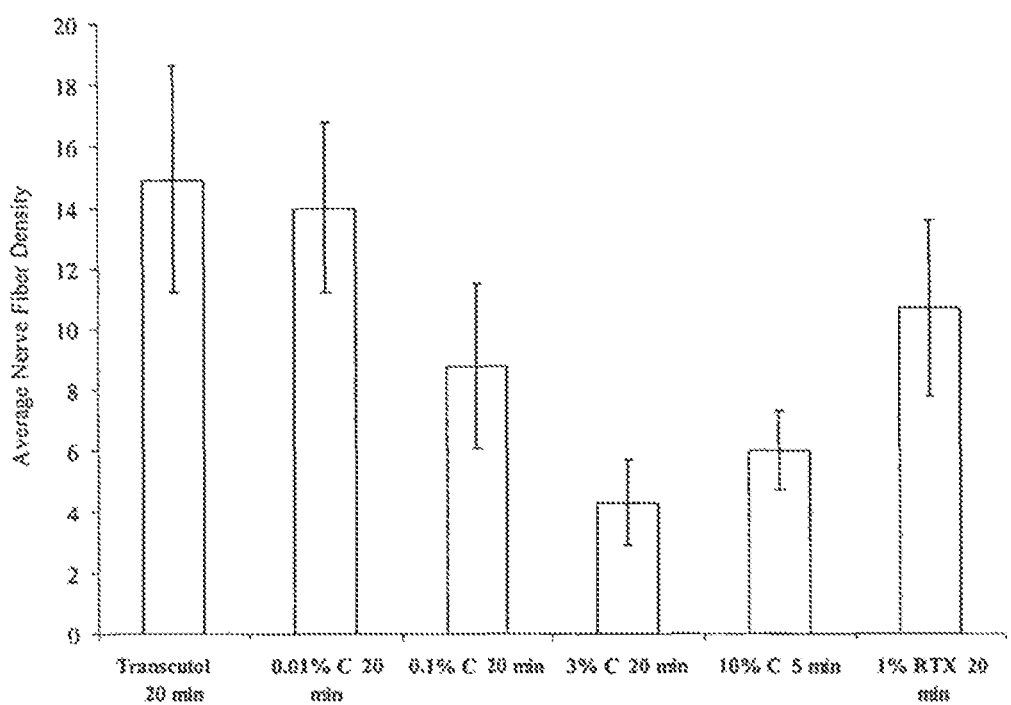
FIG. 2 shows reduction of nerve fiber density in vulva (rat) after administration of TRPV1 agonists. Transcutol® is diethylene glycol monoethyl ether (DGME).

The results of this study are shown in FIG. 2. These results indicated that three capsaicin-containing formulations with capsaicin concentrations greater than 0.01% (w/v) and higher caused a statistically significant ($p \le 0.1$) decrease in nerve fiber density as demonstrated by PGP 9.5 immunostaining following application periods of 5 or 20 minutes. A 1% (w/v) liquid formulation of another TRPV1 agonist resiniferatoxin (RTX) when applied for 20 minutes produced a 28% decrease in nerve fiber density in this experiment; however, additional experiments are needed to establish statistical significance of the observed decrease.

Example 4

Pain Behavior Following Treatment of Vulva

This example shows the amount of nocifensive behaviors produced by applications of 10% capsaicin (w/v) in diethylene glycol monoethyl ether, 3% capsaicin (w/v) in diethylene glycol monoethyl ether, diethylene glycol monoethyl ether alone, and Zostrix®, a commercially available 0.075% (w/v) capsaicin cream formulation, when applied to vulva of retired Sprague-Dawley breeder rats.

Treatment Groups

| Dose Group | Application Vol. (µL) | Duration of Application (min.) | N |
|---|---|---|---|
| diethylene glycol monoethyl ether (DGME) | 33 | 20 | 6 |
| Zostrix ® | 50 | 20 | 6 |
| 3% Capsaicin (w/v) in 100% DGME | 33 | 20 | 6 |
| 10% Capsaicin (w/v) in 100% DGME | 33 | 5 | 6 |

The rats were monitored for 0.5 minutes for a baseline pain behavior. The test article was applied. After the indicated application time, residual capsaicin was removed from vulva with a cleansing gel (89.08% PEG-300, 1.0% Carbopol 1382™, 0.02% butylated hydroxyanisole, 0.01% disodium edentate, pH 6.5). Following application of the test article, pain behavior was monitored for 60 minutes. The following behaviors were considered as pain responses: licking or grooming the vulva area, looking down at the vulva, sniffing the vulva, licking and chewing motion with mouth, standing on hind legs and lifting tail, running around the cage, crawling along the bottom of the cage, sitting up and pointing nose towards abdomen, excessive or frantic grooming, stretching hind legs, lifting tail, digging at the bottom of the cage, and stretching posture.

Figure 3:
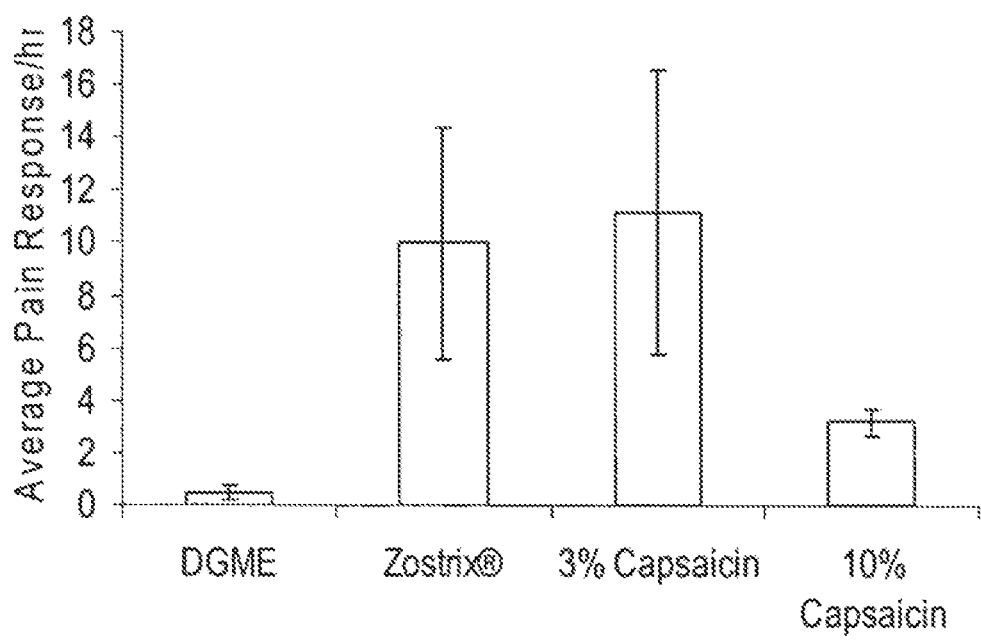
FIG. 3 shows pain behavior after application of TRPV1 agonist to vulva (rat).
Figure 4:
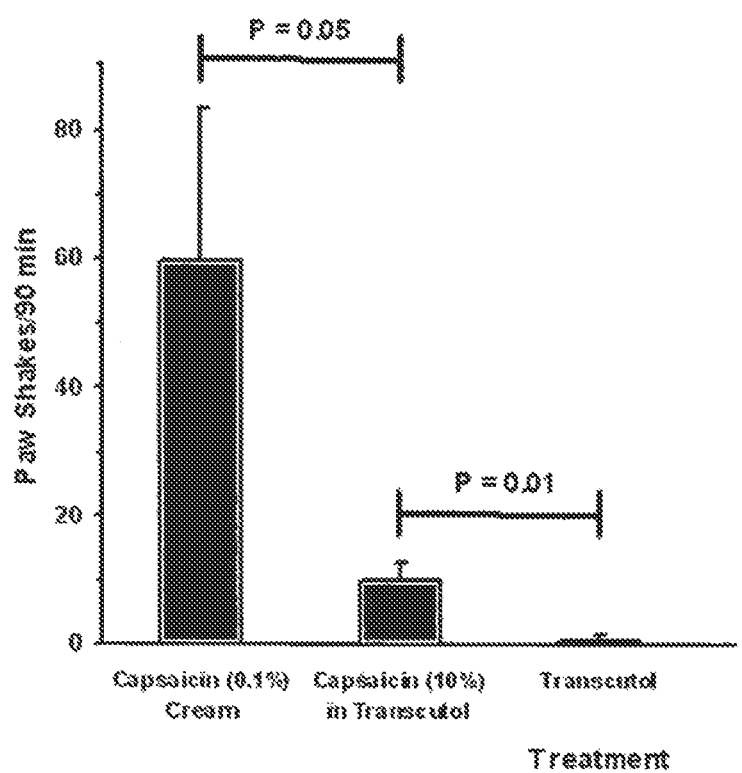
FIG. 4 shows pain behavior after application of TRPV1 agonist to skin (rat dorsal paw).

FIG. 3 shows the results of the experiment. Capsaicin containing (3% and 10% w/v) liquid formulations and over-the-counter capsaicin containing (0.075%) cream (Zostrix®) produced greater pain response than diethylene glycol monoethyl ether alone, when applied to rat vulva for either 5 minutes or 20 minutes. However, there was no statistically significant difference in pain responses among 3% w/v capsaicin liquid formulation and Zostrix®. Surprisingly, a 10% w/v capsaicin liquid formulation produced statistically significant (p≤0.1) less pain response than the Zostrix® cream containing 0.075% capsaicin.

Example 5

Pain Behavior Following Treatment of Skin

This example shows the amount of nocifensive behaviors in rats following a single topical application of capsaicin (10% w/v) in diethylene glycol monoethyl ether (Transcutol™) compared to a commercial concentration capsaicin cream (0.1% w/w; Capzasin-HP® capsaicin cream) or diethylene glycol monoethyl ether alone.

Materials and Methods

Adult, male, Sprague-Dawley rats (250-300 g, N=19) were placed in a chamber and anesthetized with 2-3% halothane in air. Once each rat exhibited a sufficient depth of anesthesia, as indicated by a lack of withdrawal response to pinching of the tail, the rat was removed from the chamber and fitted with a facemask delivering 1-2% halothane. The rat was placed on a warming blanket and positioned on its left side with both hind limbs extended. The dorsum of the each hind paw was cleaned of debris and wiped with an isopropyl (rubbing) alcohol wipe. A chemical depilatory agent was applied to the dorsum of each hind paw. Ten-minutes later, the depilatory agent was removed with gauze then the dorsum of each hind paw was wiped with an isopropyl alcohol wipe. The dorsum of both hind paws was inspected to ensure that no visible hair remained. The halothane was discontinued and rats were allowed to recover in their cages.

Once rats were ambulating normally, they were placed on an elevated plastic mesh and covered with a plastic container. Rats were allowed to acclimate on the mesh for at least 30 minutes. Next, the number of times that a rat shook its right hind paw over a 5-minute period was recorded. A hind paw shake was recorded only if the rat clearly elevated its right hind paw and shook it while it was not ambulating. After this baseline evaluation, each rat was removed from the mesh and wrapped gently in a cloth towel. The dorsum of the right hind paw was wiped with an isopropyl wipe. Immediately after the alcohol evaporated, one of the following treatments was applied to the dorsum of the right hind paw.

i) Capzasin-HP® 0.1% capsaicin cream (~0.15 g);
ii) 50 µl DGME containing 10% (w/v) capsaicin;
iii) 50 µl DGME.

A cotton-tipped applicator was used to apply the capsaicin cream and the cream was rubbed into the dorsum of the hind paw for 10 sec. The capsaicin liquid formulation and DGME were applied to the dorsum of the right hind paw with a pipetter and the rat was kept immobile for 10 sec. After application of each treatment, rats were placed back onto the mesh and covered with the plastic container. The number of times that each rat shook its right hind paw was recorded for consecutive 5-minute periods for a total of 90 minutes.

Statistical Analyses

The number of times that rats shook their right hind paw is presented as the mean (±sem) for each treatment group. One-tailed t-tests were used to determine if there were significant differences between treatment groups in the number of hind paw shakes during each 5 minute period and over the entire 90 minute period. For all analyses, a probability (P-value) of less than or equal to 0.05 was considered significant.

Results

During the baseline 5-minute period, rats did not shake their right hind paw. As shown in FIG. 1, application of capsaicin (0.1%) cream evoked 59.4±23.7 shakes over the 90-minute observation period. Application of the capsaicin liquid formulation (10% capsaicin (w/v) in DGME) produced significantly less hind paw shakes (10.2±2.4 shakes, P≤0.05). In contrast, application of DGME alone produced almost no nocifensive behavior (0.7±0.7 shakes) in the 90-minute period, which was significantly fewer hind paw shakes than that produced by 10% capsaicin in DGME (P≤0.01).

Discussion

The results of this example suggest that topical application of the 10% capsaicin liquid formulation produced less nocifensive behavior (i.e., hind paw shakes) over a 90-minute observation period than did topical application of a commercially available over-the-counter low-concentration (0.1%) capsaicin cream. Application of the capsaicin liquid formulation did evoke more hind paw shakes than did diethylene glycol monoethyl ether alone.

Example 6

Preparation of Microemulsion Containing 0.1% Capsaicin (w/v)

A microemulsion is produced by preparing a first composition containing capsaicin and diethylene glycol monoethyl ether. The first composition is made by dissolving 10 g of capsaicin in 100 mL diethylene glycol monoethyl ether (DGME) to form the internal phase. A microemulsion is prepared by adding the first composition to 1 L (one liter) of mineral oil, followed by addition of 10 to 30% (w/w) caprylocaproyl macrogol-8 glycerides (emulsifier), stirring until the caprylocaproyl macrogol-8 glycerides are dissolved, to produce a second composition ("oil phase").

Prior to use or administration, 100 mL of the oil phase is added to 1 L of water or saline (external phase), followed by thorough mixing until a stable microemulsion is formed. The resulting microemulsion contains 0.1% capsaicin (w/v).

Example 7

Preparation of an Oil in Water Microemulsion

The following example shows an oil in water microemulsion formulation.

| Excipient | % w/w |
|---|---|
| Tetrahydrofurfuryl alcohol (Glycofurol ®) | 40 |
| Vitamin E TPGS | 20 |
| Propylene glycol | 10 |
| Isopropyl myristate | 10 |
| Span 80 | 5 |
| Tween 80 | 5 |
| Deionised water | 10 |

All the excipients were weighed into a vial and heated on a water bath at 60° C. until a uniform solution was formed. The solution was allowed to cool down to room temperature. A cloudy dispersion of o/w emulsion was obtained. In order to incorporate the drug into the formulation, capsaicin was weighed along with the rest of the excipients and heated on the water bath and allowed to cool down to form an o/w emulsion.

Example 8

Preparation of a Liposome Microemulsion

This example shows a liposome microemulsion formulation.

| Excipient | % w/w |
|---|---|
| Lipoid S-100-3 | 9 |
| Lipoid S-PG-3 | 1 |
| Propylene Glycol | 65 |
| PBS | 25 |

All the ingredients were weighed directly into a vial and heated on a water bath at 70° C. until all the lipids were solubilized. To incorporate capsaicin, the drug was be weighed along with the main excipients of the formulation and heated on the water bath until a uniform single phased solution was obtained. This solution was then homogenised until it naturally cooled down to the room temperature. A smooth white cream was obtained. Formation of liposomes was checked under the microscope. A 1 in 10 and a 1 in 100 dilution of the liposome formulation in deionised water did not alter the physical characteristics of the liposomes as observed under a microscope.

Example 9

Preparation of a Cosolvent Composition

This example shows a co-solvent composition.

The co-solvent pre-concentrates essentially consist of a surfactant (Poloxamer) solubilized in alcohol. The following example of the solvent systems was formulated to contain 10% w/v concentration of capsaicin. A dilution of the formulation in an aqueous medium resulted in a clear solution.

In order to incorporate the drug into the formulation, the desired amount of capsaicin was weighed into the vial followed by the addition of ethanol to solubilize the drug. This was followed by the addition of Poloxamer 407, which was solubilized, and the rest of the ingredients were weighed into the bottle directly. The formulation was mixed on a vortex mixer to form a clear liquid.

| Co-solvent pre-concentrate | |
|---|---|
| Excipient | % w/w |
| Poloxamer 407 | 20 |
| Ethanol | 40 |
| Tetrahydrofurfuryl alcohol (Glycofurol ®) | 5 |
| Deionised Water | 35 |

Although the foregoing invention has been described in some detail by way of illustration and examples for purposes of clarity of understanding, it will be apparent to those skilled in the art that certain changes and modifications may be practiced without departing from the spirit and scope of the invention. All publications, patents and patent applications cited herein are hereby incorporated by reference in their entirety for all purposes to the same extent as if each individual publication, patent or patent application were specifically and individually indicated to be so incorporated by reference.

TABLE 1

| Penetration Enhancer | Chemical Class |
|---|---|
| Diethylene glycol monoethyl ether | Ether |
| Benzyl alcohol | Alcohol |
| Isopropyl myristate | Fatty acid ester |
| 1-Menthone | Terpene (ketone) |
| Dimethyl isosorbide | Ureas |
| Caprylic alcohol | Fatty Alcohol |
| Lauryl alcohol | Fatty Alcohol |
| Oleyl alcohol | Fatty Alcohol |
| Ethylene glycol | Polyol |
| Diethylene glycol | Polyol |
| Triethylene glycol | Polyol |
| Butylene glycol | Polyol |
| Valeric acid | Fatty acid |
| Pelargonic acid | Fatty acid |
| Caproic acid | Fatty acid (linear) |
| Caprylic acid | Fatty acid (linear) |
| Laurie acid | Fatty acid (linear) |
| Oleic acid | Fatty acid (linear) |
| Isovaleric acid | Fatty acid (branched) |
| Methyl nonenoic acid | Fatty acid (branched) |
| Isopropyl butyrate | Fatty acid ester |
| Isopropyl hexanoate | Fatty acid ester |
| Butyl acetate | Fatty acid ester |
| Methyl acetate | Fatty acid ester |
| Methyl valerate | Fatty acid ester |
| Ethyl oleate | Fatty acid ester |
| Poloxamer | Surfactant |
| d-Piperitone | Terpene (ketone) |

TABLE 1-continued

| Penetration Enhancer | Chemical Class |
|---|---|
| d-Pulegone | Terpene (ketone) |
| Dimethylsolfoxide | Sulfoxides |
| n-Hexane | Alkanes |
| Citric acid | Organic acid |

TABLE 2

| Penetration Enhancer | Chemical Class |
|---|---|
| Ethanol | Alcohol |
| Propanol | Alcohol |
| Isopropanol | Alcohol |
| Ethyl acetate | Ester |
| Methyl propionate | Fatty acid ester |
| Methanol | Alcohol |
| Butanol | Alcohol |
| Tert-butanol | Alcohol |
| Octanol | Alcohol |

TABLE 3

| Penetration Enhancer | Chemical Class |
|---|---|
| Myristyl alcohol | Fatty Alcohol |
| Methyl nonenoyl alcohol | Fatty Alcohol |
| Cetyl alcohol | Fatty Alcohol |
| Cetearyl alcohol | Fatty Alcohol |
| Stearyl alcohol | Fatty Alcohol |
| Myristic acid | Fatty Acid |
| Stearic acid | Fatty Acid |
| Isopropyl palmitate | Fatty acid ester |
| Sodium lauryl sulfate | Surfactant (anionic) |
| Benzalkonium chloride | Surfactant (cationic) |
| Brij 35 | Surfactant (nonionic) |
| Tween 80 | Surfactant (nonionic) |
| Citric acid | Organic Acid |
| Salicylic acid | Organic Acid |

TABLE 4

| Form. No. | Agonist Conc.* (% w/v) | Component 1 (v/v %) | Component 2 (v/v %) | Component 3 (v/v %) | Component 4 (v/v %) | Component 5 (v/v %) |
|---|---|---|---|---|---|---|
| 1 | 15 | 1,3-Butanediol (50) | Oleic acid (40) | Benzyl alcohol (10) | — | — |
| 2 | 15 | Diethylene glycol mono ethyl ether (50) | Oleic acid (40) | Benzyl alcohol (10) | — | — |
| 3 | 15 | Diethylene glycol mono ethyl ether (50) | Ethyl oleate (30) | Oleic Acid (10) | Isopropyl myristate (10) | — |
| 4 | 15 | 1,3-Butanediol (50) | n-Caproic acid (20) | Myristic acid (10) | Diethylene glycol mono ethyl ether (20) | — |
| 5 | 15 | Diethylene glycol (60) | Diethylene glycol mono ethyl ether (15) | 1,3-Butanediol (15) | Benzyl alcohol (10) | — |
| 6 | 15 | d-Piperitone (30) | Diethylene glycol mono ethyl ether (20) | Oleic Acid (20) | Ethyl oleate (30) | — |
| 7 | 15 | d-Pipertone (30) | Benzyl alcohol (20) | Oleic acid (20) | Ethyl oleate (30) | — |
| 8 | 15 | l-Menthone (30) | Benzyl alcohol (20) | Oleic acid (20) | Ethyl oleate (30) | — |
| 9 | 15 | Diethylene glycol mono ethyl ether (70) | Phosphate buffer (10) | Benzyl alcohol (20) | — | — |
| 10 | 15 | Diethylene glycol mono ethyl ether (55) | Oleic acid (30) | Benzyl alcohol (10) | Dimethyl isosorbide (5) | — |
| 11 | 15 | Isopropyl butyrate (65) | Diethylene glycol mono ethyl ether (20) | Benzyl alcohol (10) | Cetyl alcohol (5) | — |
| 12 | 15 | Diethylene glycol mono ethyl ether (49.05) | Oleic acid (40) | Benzyl alcohol (10) | Sodium lauryl sulfate (0.05) | — |
| 13 | 15 | Diethylene glycol mono ethyl ether (60) | Oleic acid (40) | — | — | — |
| 14 | 15 | Ethylene glycol (60) | Diethylene glycol mono ethyl ether (20) | 1,3-Butanediol (20) | — | — |
| 15 | 15 | Oleyl alcohol (65) | Isoproply butyrate (20) | Benzyl alcohol (10) | l-Menthone (5) | — |

TABLE 4-continued

| Form. No. | Agonist Conc.* (% w/v) | Component 1 (v/v %) | Component 2 (v/v %) | Component 3 (v/v %) | Component 4 (v/v %) | Component 5 (v/v %) |
|---|---|---|---|---|---|---|
| 16 | 15 | Diethylene glycol mono ethyl ether (50) | Oleic acid (40) | Benzyl alcohol (10) | — | — |
| 17 | 15 | 1,3-Butanediol (60) | Oleic acid (40) | — | — | — |
| 18 | 15 | 1,3-Butanediol (70) | Benzyl alcohol (20) | Phosphate buffer (10) | — | — |
| 19 | 15 | Isopropanol (100) | — | — | — | — |
| 20 | 15 | Methyl propionate (100) | — | — | — | — |
| 21 | 15 | Dimethylacetamide (5) | Brij35 (1) | Methylnonenoic alcohol (94) | — | — |
| 22 | 15 | n-Hexane (10) | Methylnonenoic acid (90) | — | — | — |
| 23 | 10 | Diethylene glycol mono ethyl ether (100) | — | — | — | — |
| 24 | 1 | Diethylene glycol mono ethyl ether (100) | — | — | — | — |
| 25 | 10 | Oleic acid (15) | Isopropyl myristate (5) | Cetyl alcohol (5) | Diethylene glycol mono ethyl ether (75) | |
| 26 | 10 Olvanil | Diethylene glycol mono ethyl ether (90) | DMSO (10) | | | |
| 27 | 15 or 2 | Menthone (90) | Methanol (10) | — | — | — |
| 28 | 15 | Oleyl alcohol (20) | Propylene glycol (80) | — | — | — |
| 29 | 5.12 | Oleyl alcohol (20) | Propylene glycol (80) | — | — | — |
| 30 | 5.12 | 1,3-Butanediol (60) | Oleic acid (40) | — | — | — |
| 31 | 5.12 | Menthone (90) | Methanol (10) | — | — | — |
| 32 | 1 | Oleic acid (15) | Isopropyl myristate (5) | Cetyl alcohol (5) | Diethylene glycol mono ethyl ether (75) | |
| 33 | 1 | Diethylene glycol mono ethyl ether (90) | DMSO (10) | — | | |
| 34 | 1 | Diethylene glycol mono ethyl ether (5) | Propylene Glycol (40) | Phosphate Buffer (10) | | |
| 35 | 1 | Methanol (100) | — | — | — | — |
| 36 | 1 | Diethylene glycol mono ethyl ether (100) | — | — | — | — |
| 37 | 0.1 | Diethylene glycol mono ethyl ether (100) | — | — | — | — |
| 38 | 0.3 | Diethylene glycol mono ethyl ether 100 | — | — | — | — |
| 39 | 1 | Diethylene glycol mono ethyl ether (100) | — | — | — | — |
| 40 | 3 | Diethylene glycol mono ethyl ether 100 | — | — | — | — |
| 41 | 10 | Diethylene glycol mono ethyl ether 100 | — | — | — | — |

TABLE 4-continued

| Form. No. | Agonist Conc.* (% w/v) | Component 1 (v/v %) | Component 2 (v/v %) | Component 3 (v/v %) | Component 4 (v/v %) | Component 5 (v/v %) |
|---|---|---|---|---|---|---|
| 42 | 15 | Oleic acid (15) | Isopropyl myristate (10) | Cetyl alcohol (10) | Diethylene glycol mono ethyl ether (55) | Methanol (10) |

*Capsaicin, except where noted.

TABLE 5

| Form. No. | Capsaicin % w/v | Application Time | P = Amount in receptor fluid (nmol) | D = Amount in dermis (nmol) | E = Amount in epidermis (nmol) | S = Amount in skin (nmol) | P/S | D/E |
|---|---|---|---|---|---|---|---|---|
| 1 | 15 | 15 | 0.39 | 8.8 | 16.1 | 24.9 | 0.0157 | 0.546 |
| 2 | 15 | 15 | 0.28 | 13.26 | 21.19 | 34.45 | 0.0081 | 0.626 |
| 3 | 15 | 15 | 0.41 | 10.03 | 22.46 | 32.49 | 0.0126 | 0.447 |
| 4 | 15 | 15 | 0.36 | 13.83 | 16.47 | 30.3 | 0.0119 | 0.84 |
| 5 | 15 | 15 | 0.04 | 3.45 | 6.48 | 9.93 | 0.004 | 0.533 |
| 6 | 15 | 15 | 0.08 | 9.44 | 22.38 | 31.83 | 0.0025 | 0.422 |
| 7 | 15 | 15 | 0.66 | 9.02 | 14.16 | 23.18 | 0.0285 | 0.637 |
| 8 | 15 | 15 | 0.11 | 7.69 | 21.01 | 28.7 | 0.0038 | 0.366 |
| 9 | 15 | 15 | 0.19 | 7.73 | 15.05 | 22.79 | 0.0083 | 0.513 |
| 10 | 15 | 15 | 0.69 | 8.76 | 23.82 | 32.59 | 0.0212 | 0.368 |
| 11 | 15 | 15 | 0.45 | 16.04 | 25.98 | 42.02 | 0.0107 | 0.617 |
| 12 | 15 | 15 | 0.28 | 12.03 | 13.24 | 25.27 | 0.0111 | 0.909 |
| 13 | 15 | 15 | 0.54 | 19.2 | 18.26 | 37.46 | 0.0144 | 1.052 |
| 14 | 15 | 15 | 1.41 | 12.16 | 16.89 | 29.06 | 0.0485 | 0.72 |
| 15 | 15 | 15 | 0.19 | 12.48 | 35.91 | 48.4 | 0.0039 | 0.348 |
| 16 | 15 | 15 | 0.75 | 9.47 | 19.73 | 29.21 | 0.0257 | 0.48 |
| 17 | 15 | 15 | 0.09 | 16.51 | 17.39 | 33.89 | 0.0027 | 0.95 |
| 18 | 15 | 15 | 0.36 | 9.22 | 9.34 | 18.56 | 0.0194 | 0.987 |
| 19 | 15 | 15 | 0.88 | 11.24 | 19.14 | 30.39 | 0.029 | 0.587 |
| 20 | 15 | 15 | 0.2 | 22.99 | 31.09 | 54.08 | 0.0037 | 0.74 |
| 21 | 15 | 15 | 5.11 | 33.55 | 33.01 | 66.56 | 0.0768 | 1.017 |
| 22 | 15 | 15 | 2.9 | 44.32 | 31.7 | 76.02 | 0.0381 | 1.398 |
| 23 | 10 | 30 | 3.61 | 14.75 | 9.57 | 24.31 | 0.1485 | 1.541 |
| 23 | 10 | 15 | 1.97 | 21.87 | 14.63 | 36.49 | 0.054 | 1.495 |
| 23 | 10 | 5 | 1.73 | 11.27 | 6.11 | 17.37 | 0.0996 | 1.845 |
| 24 | 1 | 15 | 0.44 | 3.7 | 1.08 | 4.78 | 0.0921 | 3.411 |
| 25 | 10 | 10 | 1.23 | 12.73 | 9.8 | 22.52 | 0.0546 | 1.299 |
| 27 | 15 | 15 | 0.06 | 24.26 | 62.96 | 87.22 | 0.0007 | 0.385 |
| 27 | 15 | 2 | 0.11 | 6.33 | 22.33 | 28.66 | 0.0038 | 0.283 |
| 28 | 15 | 15 | 0.1 | 29.87 | 47.42 | 77.29 | 0.0013 | 0.63 |
| 28 | 15 | 2 | 1.31 | 6.61 | 13.21 | 19.83 | 0.0661 | 0.5 |
| 32 | 5.12 | 15 | 0.01 | nd | nd | 6.53 | 0.0015 | — |
| 35 | 5.12 | 15 | 0.01 | nd | nd | 7.1 | 0.0014 | — |
| 36 | 5.12 | 15 | 0.01 | nd | nd | 4.04 | 0.0025 | — |
| 42 | 15 | 15 | 0.02 | 28.1 | 27.71 | 55.81 | 0.0004 | 1.014 |

TABLE 6

EXEMPLARY SOLVENT SYSTEMS (v/v)

1. Oleyl alcohol 100%
2. Methylnonenoyl alcohol 100%
3. Methylnonenoic acid 100%
4. Menthone 95%, Methanol 5%
5. Menthone 85% Methanol 15%
6. Menthone 80% Methanol 20%
7. Menthone 75% Methanol 25%
8. Menthone 70% Methanol 30%
9. Oleyl alcohol 10% Propylene glycol 90%
10. Oleyl alcohol 25% Propylene glycol 75%
11. Oleyl alcohol 30% Propylene glycol 70%
12. Oleyl alcohol 35% Propylene glycol 65%
13. Oleyl alcohol 40% Propylene glycol 60%
14. Oleyl alcohol 45% Propylene glycol 55%
15. Oleyl alcohol 50% Propylene glycol 50%
16. Oleyl alcohol 60% Propylene glycol 40%

TABLE 6-continued

EXEMPLARY SOLVENT SYSTEMS (v/v)

17. Oleyl alcohol 70% Propylene glycol 30%
18. Oleyl alcohol 80% Propylene glycol 20%
19. Methylnonenoyl alcohol 95% 1-Menthone 5%
20. Methylnonenoyl alcohol 90% 1-Menthone 10%
21. Methylnonenoyl alcohol 80% 1-Menthone 20%
22. Methylnonenoyl alcohol 60% 1-Menthone 40%
23. Methylnonenoyl alcohol 40% 1-Menthone 60%
24. Methylnonenoyl alcohol 30% 1-Menthone 70%
25. Methylnonenoyl alcohol 20% 1-Menthone 80%
26. Methylnonenoyl alcohol 10% 1-Menthone 90%
27. Methylnonenoyl acid 5% 1-Menthone 95%
28. Methylnonenoyl acid 95% 1-Menthone 5%
29. Methylnonenoic acid 90% 1-Menthone 10%
30. Methylnonenoic acid 80% 1-Menthone 20%
31. Methylnonenoic acid 60% 1-Menthone 40%
32. Methylnonenoic acid 40% 1-Menthone 60%
33. Methylnonenoic acid 30% 1-Menthone 70%
34. Methylnonenoic acid 20% 1-Menthone 80%
35. Methylnonenoic acid 10% 1-Menthone 90%
36. Methylnonenoic acid 5% 1-Menthone 95%
37. Methylnonenoyl alcohol 95% oleic acid 5%
38. Methylnonenoyl alcohol 90% oleic acid 10%
39. Methylnonenoyl alcohol 80% oleic acid 20%
40. Methylnonenoyl alcohol 70% oleic acid 30%
41. Methylnonenoyl alcohol 95% Dimethylacetamide 5%
42. Methylnonenoyl alcohol 90% Dimethylacetamide 10%
43. Methylnonenoyl alcohol 80% Dimethylacetamide 20%
44. Methylnonenoyl alcohol 50% Methylnonenoic acid 50%
45. Methylnonenoyl alcohol 70% Methylnonenoic acid 30%
46. Methylnonenoyl alcohol 80% Methylnonenoic acid 20%
47. Methylnonenoyl alcohol 90% Methylnonenoic acid 10%
48. Methylnonenoyl alcohol 40% Methylnonenoic acid 60%
49. Methylnonenoyl alcohol 30% Methylnonenoic acid 70%
50. Methylnonenoyl alcohol 20% Methylnonenoic acid 80%
51. Methylnonenoyl alcohol 10% Methylnonenoic acid 90%
52. Methylnonenoyl alcohol 90% Oleyl alcohol 10%
53. Methylnonenoyl alcohol 80% Oleyl alcohol 20%
54. Methylnonenoyl alcohol 70% Oleyl alcohol 30%
55. Methylnonenoyl alcohol 60% Oleyl alcohol 40%
56. Methylnonenoic alcohol 50% Oleyl alcohol 50%
57. Methylnonenoyl alcohol 40% Oleyl alcohol 60%
58. Methylnonenoyl alcohol 30% Oleyl alcohol 70%
59. Methylnonenoyl alcohol 20% Oleyl alcohol 80%
60. Methylnonenoyl alcohol 10% Oleyl alcohol 90%
61. Methylnonenoyl alcohol 90% Propylene glycol 10%
62. Methylnonenoyl alcohol 80% Propylene glycol20%
63. Methylnonenoyl alcohol 70% Propylene glycol30%
64. Methylnonenoyl alcohol 60% Propylene glycol40%
65. Methylnonenoic alcohol 50% Propylene glycol50%
66. Methylnonenoyl alcohol 40% Propylene glycol60%
67. Methylnonenoyl alcohol 30% Propylene glycol70%
68. Methylnonenoyl alcohol 20% Propylene glycol80%
69. Methylnonenoyl alcohol 10% Propylene glycol90%
70. Methylnonenoic acid 90% Oleyl alcohol 10%
71. Methylnonenoic acid 80% Oleyl alcohol 20%
72. Methylnonenoic acid 70% Oleyl alcohol 30%
73. Methylnonenoic acid 60% Oleyl alcohol 40%
74. Methylnonenoic acid 50% Oleyl alcohol 50%
75. Methylnonenoic acid 40% Oleyl alcohol 60%
76. Methylnonenoic acid 30% Oleyl alcohol 70%
77. Methylnonenoic acid 20% Oleyl alcohol 80%
78. Methylnonenoic acid 10% Oleyl alcohol 90%
79. Methylnonenoic acid 90% Propylene glycol 10%
80. Methylnonenoic acid 80% Propylene glycol20%
81. Methylnonenoic acid 70% Propylene glycol30%
82. Methylnonenoic acid 60% Propylene glycol40%
83. Methylnonenoic acid 50% Propylene glycol50%
84. Methylnonenoic acid 40% Propylene glycol60%
85. Methylnonenoic acid 30% Propylene glycol70%
86. Methylnonenoic acid 20% Propylene glycol80%
87. Methylnonenoic acid 10% Propylene glycol90%
88. Methylnonenoyl alcohol 99% Brij35 1%
89. Methylnonenoyl alcohol 94.5% Dimethylacetamide 5% Brij35 0.5%
90. Methylnonenoyl alcohol 95.9% Dimethylacetamide 5% Brij35 0.1%
91. Oleic acid 15% Isopropyl myristate 15% DGME 60% Methanol 10%
92. Oleic acid 20% Isopropyl myristate 15% DGME 55% Methanol 10%
93. Oleic acid 15% Isopropyl myristate 15% DGME 60% Cetyl alcohol 10%
94. Oleic acid 20% Isopropyl myristate 15% DGME 55% Cetyl alcohol 10%

TABLE 6-continued

EXEMPLARY SOLVENT SYSTEMS (v/v)

95. Oleic acid 10% Isopropyl myristate 10% Cetyl alcohol 10% DGME 60% Methanol 10%
96. Oleic acid 20% Isopropyl myristate 10% Cetyl alcohol 10% DGME 50% Methanol 10%
97. Oleic acid 30% Isopropyl myristate 10% Cetyl alcohol 10% DGME 40% Methanol 10%
98. Oleic acid 40% Isopropyl myristate 10% Cetyl alcohol 10% DGME 30% Methanol 10%
99. Oleic acid 15% Isopropyl myristate 5% Cetyl alcohol 10% DGME 60% Methanol 10%
100. Oleic acid 15% Isopropyl myristate 10% Cetyl alcohol 5% DGME 60% Methanol 10%
101. Oleic acid 15% Isopropyl myristate 10% Cetyl alcohol 10% DGME 60% Methanol 5%
102. Oleic acid 10% Isopropyl myristate 10% Cetyl alcohol 10% Methylnonenoyl alcohol 60% Methanol 10%
103. Oleic acid 20% Isopropyl myristate 10% Cetyl alcohol 10% Methylnonenoyl alcohol 50% Methanol 10%
104. Oleic acid 30% Isopropyl myristate 10% Cetyl alcohol 10% Methylnonenoyl alcohol 40% Methanol 10%
105. Oleic acid 40% Isopropyl myristate 10% Cetyl alcohol 10% Methylnonenoyl alcohol 30% Methanol 10%
106. Oleic acid 15% Isopropyl myristate 5% Cetyl alcohol 10% Methylnonenoyl alcohol 60% Methanol 10%
107. Oleic acid 15% Isopropyl myristate 10% Cetyl alcohol 5% Methylnonenoyl alcohol 60% Methanol 10%
108. Oleic acid 15% Isopropyl myristate 10% Cetyl alcohol 10% Methylnonenoyl alcohol 60% Methanol 5%
109. Oleic acid 15% Isopropyl myristate 15% Methylnonenoyl alcohol 60% Methanol 10%
110. Oleic acid 20% Isopropyl myristate 15% Methylnonenoyl alcohol 55% Methanol 10%
111. Oleic acid 15% Isopropyl myristate 15% Methylnonenoyl alcohol 60% Cetyl alcohol 10%
112. Oleic acid 20% Isopropyl myristate 15% Methylnonenoyl alcohol 55% Cetyl alcohol 10%

We claim:

1. A method of delivering a TRPV1 agonist to the epidermis and dermis underlying a 1 cm$^2$ area of a skin or mucosal surface of a mammal, comprising non-occlusively or non-adherently contacting the area with a composition comprising the TRPV1 agonist and at least one penetration enhancer, wherein 30 minutes after said contacting at least about 3 nmoles of the TRPV1 agonist is retained in the epidermis and dermis.

2. The method of claim 1 wherein 15 minutes after said contacting at least about 3 nmoles of the TRPV1 agonist is retained in the epidermis and dermis.

3. The method of claim 2 wherein at least about 32 nmoles of the TRPV1 agonist is retained in the epidermis and dermis.

4. The method of claim 3 wherein at least about 49 nmoles of the TRPV1 agonist is retained in the epidermis and dermis.

5. The method of claim 4 wherein at least about 65 nmoles of the TRPV1 agonist is retained in the epidermis and dermis.

6. The method of claim 2 wherein at least about 16 nmoles of the TRPV1 agonist is retained in the epidermis and dermis.

7. The method of claim 2 wherein the TRPV1 agonist is capsaicin.

8. The method of claim 2 wherein the area contacted is skin.

9. The method of claim 8 wherein the mammal is a human.

10. The method of claim 9 wherein the human suffers from a capsaicin responsive condition.

11. The method of claim 2 wherein the density of functional nociceptive nerve fibers in the epidermis and dermis is decreased by at least about 20% when measured from 2 to 7 days after said contacting step.

12. The method of claim 2 wherein the composition delivers at least about 3 nmoles of the TRPV1 agonist to skin as measured in a mouse skin absorption assay.

13. The method of claim 2 wherein the at least one penetration enhancer is selected from the group consisting of ethers, esters, alcohols, fatty acids, fatty acid esters, fatty alcohols, polyols, terpenes, and amines.

14. A method of reducing the density of functional nociceptive nerve fibers in a selected region of a subject, comprising non-occlusively or non-adherently contacting the selected region with an immediate-release composition that comprises a TRPV1 agonist and one or more penetration enhancers, wherein said composition delivers at least about 3 nmoles of the TRPV1 agonist to skin as measured in a mouse skin absorption assay.

15. A method of reducing the density of functional nociceptive nerve fibers in a selected region of a subject, comprising non-occlusively or non-adherently contacting the selected region with a composition that comprises a TRPV1 agonist and a solvent system comprising one or more penetration enhancers, wherein said composition delivers at least about 3 nmoles of the TRPV1 agonist to skin as measured in a mouse skin absorption assay, and wherein at least about 5 µl of the composition is delivered to each cm$^2$ of the selected region in about 15 minutes.

16. The method of claim 14 wherein the selected region is on the surface of skin or mucosa.

17. The method of claim 14 wherein said composition delivers at least about 6 nmoles of the TRPV1 agonist to skin.

18. The method of claim 17 wherein said composition delivers at least about 16 nmoles of the TRPV1 agonist to skin.

19. The method of claim 18 wherein said composition delivers at least about 32 nmoles of the TRPV1 agonist to skin.

20. The method of claim 19 wherein said composition delivers at least about 49 nmoles of the TRPV1 agonist to skin.

21. The method of claim 20 wherein said composition delivers at least about 65 nmoles of the TRPV1 agonist to skin.

22. The method of claim 14 wherein said composition delivers from about 5 nmoles to about 290 moles of the TRPV1 agonist to skin.

23. The method of claim 14 wherein the depot effect of said contacting is less than about 0.25 as measured in a mouse skin absorption assay.

24. The method of claim 23 wherein the depot effect is less than about 0.1.

25. The method of claim 24 wherein the depot effect is less than about 0.02.

26. The method of claim 25 wherein the depot effect is less than about 0.001.

27. The method of claim 14 wherein the depot effect is in a range of about 0.001 to about 0.25.

28. The method of claim 14 wherein the distribution effect of said contacting is in the range of 0.5 to 2, as measured in a mouse skin absorption assay.

29. The method of claim 14 wherein the composition comprises the TRPV1 agonist and a solvent system, wherein penetration enhancer(s) make up at least 20% (v/v) of the solvent system.

30. The method of claim 29 wherein penetration enhancer (s) make up at least 50% (v/v) of the solvent system.

31. The method of claim 30 wherein penetration enhancer (s) make up at least 90% (v/v) of the solvent system.

32. The method of claim 31 wherein penetration enhancer (s) make up at least 95% (v/v) of the solvent system.

33. The method of claim 14 wherein the one or more penetration enhancers is selected from the group consisting of ethers, esters, alcohols, fatty acids, fatty acid esters, fatty alcohols, polyols, terpenes, and amines.

34. The method of claim 14 wherein the one or more penetration enhancers is selected from the group consisting of fatty alcohols and terpenes.

35. The method of claim 14 wherein the one or more penetration enhancers is selected from the group consisting of 1-menthone, dimethyl isosorbide, caprylic alcohol, lauryl alcohol, oleyl alcohol, ethylene glycol, diethylene glycol, triethylene glycol, butylene glycol, valeric acid, pelargonic acid, caproic acid, caprylic acid, lauric acid, oleic acid, isovaleric acid, isopropyl butyrate, isopropyl hexanoate, butyl acetate, methyl acetate, methyl valerate, ethyl oleate, poloxamer, d-piperitone, methylnonenoic acid, methylnonenoic alcohol, and d-pulegone.

36. The method of claim 14 wherein said composition comprises said TRPV1 agonist at a concentration of from 0.05% (w/v) to 60% (w/v).

37. The method of claim 36 wherein the TRPV1 agonist is a vanilloid.

38. The method of claim 37 wherein the TRPV1 agonist is capsaicin.

39. The method of claim 36 wherein said composition comprises said TRPV1 agonist at a concentration of from 1% (w/v) to 20% (w/v).

40. The method of claim 14 wherein the subject is a human.

41. The method of claim 14 wherein said contacting is by topical application or instillation.

42. The method of claim 14 wherein a 15 minute application of the composition to skin of a mammal results in a decrease in the density of functional nociceptive nerve fibers by at least about 50%, wherein the mammal is selected from the group consisting of a mouse and a human.

43. The method of claim 40 wherein the subject suffers from a capsaicin-responsive condition.

44. The method of claim 43 wherein the capsaicin-responsive condition is neuropathic pain, pain produced by mixed nociceptive and neuropathic etiologies, inflammatory hyperalgesia, vulvodynia, interstitial cystitis, overactive bladder, prostatic hyperplasia, rhinitis, rectal hypersensitivity, burning mouth syndrome, oral mucositis, herpes, prostatic hypertrophy, dermatitis, pruritis, itch, tinnitus, psoriasis, warts, skin cancers, headaches, or wrinkles.

45. A method of treating a capsaicin-responsive condition in a subject, comprising non-occlusive or non-adherent administration of a composition that comprises a TRPV1 agonist and at least one penetration enhancer, wherein said composition delivers at least about 3 nmoles of the TRPV1 agonist to skin as measured in a mouse skin absorption assay.

46. The method of claim 45 wherein the composition comprises at least two penetration enhancers.

47. The method of claim 45 wherein the composition is applied to an area on the surface of skin, mucosa, or endothelium.

48. The method of claim 45 wherein said composition delivers at least about 6 nmoles of the TRPV1 agonist to skin.

49. The method of claim 48 wherein said composition delivers at least about 16 nmoles of the TRPV1 agonist to skin.

50. The method of claim 49 wherein said composition delivers at least about 32 nmoles of the TRPV1 agonist to skin.

51. The method of claim 50 wherein said composition delivers at least about 49 nmoles of the TRPV1 agonist to skin.

52. The method of claim 51 wherein said composition delivers at least about 65 nmoles of the TRPV1 agonist to skin.

53. The method of claim 45 wherein said composition delivers from about 5 nmoles to about 290 nmoles of the TRPV1 agonist to skin.

54. The method of claim 45 wherein the depot effect of said contacting is less than about 0.25 as measured in a mouse skin absorption assay.

55. The method of claim 54 wherein the depot effect is less than about 0.1.

56. The method of claim 55 wherein the depot effect is less than about 0.02.

57. The method of claim 56 wherein the depot effect is less than about 0.001.

58. The method of claim 54 wherein the depot effect is in a range of about 0.001 to about 0.25.

59. The method of claim 45 wherein the distribution effect of said administration is in the range of 0.5 to 2 as measured in a mouse skin absorption assay.

60. The method of claim 45 wherein the composition comprises the TRPV1 agonist and a solvent system, and wherein the at least one penetration enhancer makes up at least 20% (v/v) of the solvent system.

61. The method of claim 60 wherein the at least one penetration enhancer makes up at least 50% (v/v) of the solvent system.

62. The method of claim 61 wherein the at least one penetration enhancer makes up at least 90% (v/v) of the solvent system.

63. The method of claim 62 wherein the at least one penetration enhancer makes up at least 95% (v/v) of the solvent system.

64. The method of claim 60 wherein the solvent system comprises a penetration enhancer selected from the group consisting of ethers, esters, alcohols, fatty acids, fatty acid esters, fatty alcohols, polyols, terpenes, and amines.

65. The method of claim 64 wherein the solvent system comprises a penetration enhancer selected from the group consisting of fatty alcohols and terpenes.

66. The method of claim 65 wherein said solvent system comprises a penetration enhancer selected from the group consisting of 1-menthone, dimethyl isosorbide, caprylic alcohol, lauryl alcohol, oleyl alcohol, ethylene glycol, diethylene glycol, triethylene glycol, butylene glycol, valeric acid, pelargonic acid, caproic acid, caprylic acid, lauric acid, oleic acid, isovaleric acid, isopropyl butyrate, isopropyl hexanoate, butyl acetate, methyl acetate, methyl valerate, ethyl oleate, poloxamer, d-piperitone, methylnonenoic acid, methylnonenoic alcohol, and d-pulegone.

67. The method of claim 45 wherein said composition comprises said TRPV1 agonist at a concentration of from 0.05% (w/v) to 60% (w/v).

68. The method of claim 67 wherein the TRPV1 agonist is a vanilloid.

69. The method of claim 68 wherein the TRPV1 agonist is capsaicin.

70. The method of claim 69 wherein said composition comprises said TRPV1 agonist at a concentration of from 1% (w/v) to 20% (w/v).

71. The method of claim 70 wherein a 15 minute application of the composition to skin of a mammal results in a decrease in the density of functional nociceptive nerve fibers by at least about 20% when measured 2 to 7 days after said administration step.

72. The method of claim 71 wherein a 15 minute application of the composition to skin of a mammal results in a decrease in the density of functional nociceptive nerve fibers by at least about 50% when measured 7 days after said administration step.

73. The method of claim 14 wherein the density of functional nociceptive nerve fibers in the epidermis and dermis underlying said region is decreased by at least about 20% when measured 7 days after said administration step.

74. The method of claim 45 wherein the composition is administered topically.

75. The method of claim 74 wherein the composition is administered by instillation.

76. The method of claim 45 wherein the composition is administered by injection.

77. The method of claim 45 wherein the composition is administered in the form of a microemulsion.

78. The method of claim 45 wherein the capsaicin-responsive condition is neuropathic pain, pain produced by mixed nociceptive and neuropathic etiologies, inflammatory hyperalgesia, vulvodynia, interstitial cystitis, overactive bladder, prostatic hyperplasia, rhinitis, rectal hypersensitivity, burning mouth syndrome, oral mucositis, herpes, prostatic hypertrophy, dermatitis, pruritus, itch, tinnitus, psoriasis, warts, skin cancers, headaches, or wrinkles.

79. The method of claim 78 wherein the neuropathic pain is associated with diabetic neuropathy, postherpetic neuralgia, HIV/AIDS, traumatic injury, complex regional pain syndrome, trigeminal neuralgia, erythromelalgia or phantom pain.

80. The method claim 79 wherein one or two applications of the composition provide persistent relief.

81. The method claim 80 wherein one application of the composition provides persistent relief.

82. The method of claim 45 wherein the composition is administered to an area on the surface of the skin and subsequent to administration the area is cleaned to remove any residual TRPV1 agonist.

83. The method of claim 82 wherein the area is cleaned using a composition containing at least 60% (w/w) polyethylene glycol.

84. The method of claim 45 wherein the composition further comprises one or more additional therapeutically active agents.

* * * * *